(12) United States Patent
Hezi-Yamit et al.

(10) Patent No.: US 9,510,777 B2
(45) Date of Patent: Dec. 6, 2016

(54) MONITORING OF NEUROMODULATION USING BIOMARKERS

(71) Applicant: Medtronic Ardian Luxembourg S.a.r.l., Luxembourg (LU)

(72) Inventors: Ayala Hezi-Yamit, Santa Rosa, CA (US); Rudy Beasley, Santa Rosa, CA (US); Susan Thornton Edwards, Santa Rosa, CA (US); Lori Garcia, Santa Rosa, CA (US); Michele Lee Silver, Santa Rosa, CA (US); Christopher W. Storment, Santa Rosa, CA (US); Carol M. Sullivan, Santa Rosa, CA (US); Joseph A. Traina, Santa Rosa, CA (US); Stefan Stoyanov Tunev, Santa Rosa, CA (US)

(73) Assignee: Medtronic Ardian Luxembourg S.a.r.l., Luxembourg (LU)

( * ) Notice: Subject to any disclaimer, the term of this patent is extended or adjusted under 35 U.S.C. 154(b) by 337 days.

(21) Appl. No.: 13/791,681

(22) Filed: Mar. 8, 2013

(65) Prior Publication Data

US 2013/0282001 A1 Oct. 24, 2013

Related U.S. Application Data

(60) Provisional application No. 61/608,625, filed on Mar. 8, 2012, provisional application No. 61/608,626, filed on Mar. 8, 2012, provisional application No. 61/746,528, filed on Dec. 27, 2012.

(51) Int. Cl.
*A61B 18/18* (2006.01)
*A61N 1/32* (2006.01)
(Continued)

(52) U.S. Cl.
CPC ......... *A61B 5/1405* (2013.01); *A61B 5/14503* (2013.01); *A61B 5/14546* (2013.01);
(Continued)

(58) Field of Classification Search
CPC ............ A61B 10/0045; A61B 10/007; A61B 2018/00511; A61B 2018/00577; A61B 5/1405; A61B 5/201; A61B 2018/00345; A61N 18/1492; A61N 1/3605
USPC ..................................... 606/34, 42
See application file for complete search history.

(56) References Cited

U.S. PATENT DOCUMENTS 4,602,624 A 7/1986 Naples et al.
4,649,936 A 3/1987 Ungar et al.
(Continued)

FOREIGN PATENT DOCUMENTS

CN 101489624 7/2009
EP 1169976 1/2002
(Continued)

OTHER PUBLICATIONS

Beale et al., "Minimally Invasive Treatment for Varicose Veins: A Review of Endovenous Laser Treatment and Radiofrequency Ablation". Lower Extremity Wounds 3(4), 2004, 10 pages.
(Continued)

*Primary Examiner* — Christopher D Koharski
*Assistant Examiner* — Pamela M Bays

(57) ABSTRACT

Provided herein are methods, devices, compositions, and kits for monitoring neuromodulation efficacy based on detecting changes in the level or activity of one or more target biomarkers associated with neuromodulation, as well as methods and processes of performing neuromodulation that incorporate monitoring of neuromodulation efficacy based on changes in level or activity of one or more target biomarkers.

29 Claims, 45 Drawing Sheets

(51) Int. Cl.
  *A61B 5/15* (2006.01)
  *A61B 5/157* (2006.01)
  *A61N 1/36* (2006.01)
  *A61B 5/145* (2006.01)
  *A61B 5/00* (2006.01)
  *A61N 1/05* (2006.01)
  *A61B 10/00* (2006.01)
  *A61B 5/20* (2006.01)
  *A61B 18/14* (2006.01)
  *A61B 18/00* (2006.01)
  *G01N 33/68* (2006.01)

(52) U.S. Cl.
  CPC ............ *A61B5/157* (2013.01); *A61B 5/20* (2013.01); *A61B 5/201* (2013.01); *A61B 5/4836* (2013.01); *A61B 5/6851* (2013.01); *A61B 5/6853* (2013.01); *A61B 5/6858* (2013.01); *A61B 10/0045* (2013.01); *A61B 18/1492* (2013.01); *A61B 18/18* (2013.01); *A61N 1/05* (2013.01); *A61N 1/32* (2013.01); *A61N 1/3605* (2013.01); *A61N 1/36007* (2013.01); *A61B 5/15003* (2013.01); *A61B 5/150229* (2013.01); *A61B 5/150992* (2013.01); *A61B 5/4035* (2013.01); *A61B 10/007* (2013.01); *A61B 2018/0022* (2013.01); *A61B 2018/00166* (2013.01); *A61B 2018/00214* (2013.01); *A61B 2018/00279* (2013.01); *A61B 2018/00345* (2013.01); *A61B 2018/00434* (2013.01); *A61B 2018/00511* (2013.01); *A61B 2018/00577* (2013.01); *A61B 2018/00642* (2013.01); *G01N 33/68* (2013.01); *G01N 2800/347* (2013.01)

(56) References Cited

U.S. PATENT DOCUMENTS

| | | |
|---|---|---|
| 4,709,698 A | 12/1987 | Johnston et al. |
| 4,764,504 A | 8/1988 | Johnson et al. |
| 4,890,623 A | 1/1990 | Cook et al. |
| 4,976,711 A | 12/1990 | Parins et al. |
| 5,300,068 A | 4/1994 | Rosar et al. |
| 5,301,683 A | 4/1994 | Durkan |
| 5,358,514 A | 10/1994 | Schulman et al. |
| 5,368,591 A | 11/1994 | Lennox et al. |
| 5,423,744 A | 6/1995 | Gencheff et al. |
| 5,425,364 A | 6/1995 | Imran |
| 5,484,400 A | 1/1996 | Edwards et al. |
| 5,571,147 A | 11/1996 | Sluijter et al. |
| 5,588,964 A | 12/1996 | Imran et al. |
| 5,599,345 A | 2/1997 | Edwards et al. |
| 5,626,576 A | 5/1997 | Janssen |
| 5,672,174 A | 9/1997 | Gough et al. |
| 5,688,266 A | 11/1997 | Edwards et al. |
| 5,700,282 A | 12/1997 | Zabara |
| 5,707,400 A | 1/1998 | Terry, Jr. et al. |
| 5,772,590 A | 6/1998 | Webster, Jr. |
| 5,860,974 A | 1/1999 | Abele |
| 5,865,787 A | 2/1999 | Shapland et al. |
| 5,893,885 A | 4/1999 | Webster et al. |
| 5,944,710 A | 8/1999 | Dev et al. |
| 5,954,719 A | 9/1999 | Chen et al. |
| 5,983,141 A | 11/1999 | Sluijter et al. |
| 6,004,269 A | 12/1999 | Crowley et al. |
| 6,009,877 A | 1/2000 | Edwards |
| 6,024,740 A | 2/2000 | Lesh et al. |
| 6,036,687 A | 3/2000 | Laufer et al. |
| 6,066,134 A | 5/2000 | Eggers et al. |
| 6,091,995 A | 7/2000 | Ingle et al. |
| 6,099,524 A | 8/2000 | Lipson et al. |
| 6,117,101 A | 9/2000 | Diederich et al. |
| 6,135,999 A | 10/2000 | Fanton et al. |
| 6,149,620 A | 11/2000 | Baker et al. |
| 6,161,048 A | 12/2000 | Sluijter et al. |
| 6,219,577 B1 | 4/2001 | Brown, III et al. |
| 6,224,592 B1 | 5/2001 | Eggers et al. |
| 6,246,912 B1 | 6/2001 | Sluijter et al. |
| 6,273,886 B1 | 8/2001 | Edwards et al. |
| 6,283,951 B1 | 9/2001 | Flaherty et al. |
| 6,292,695 B1 | 9/2001 | Webster, Jr. et al. |
| 6,314,325 B1 | 11/2001 | Fitz |
| 6,322,558 B1 | 11/2001 | Taylor et al. |
| 6,322,559 B1 | 11/2001 | Daulton et al. |
| 6,405,732 B1 | 6/2002 | Edwards et al. |
| 6,413,255 B1 | 7/2002 | Stern |
| 6,488,679 B1 | 12/2002 | Swanson et al. |
| 6,506,189 B1 | 1/2003 | Rittman, III et al. |
| 6,514,226 B1 | 2/2003 | Levin et al. |
| 6,522,926 B1 | 2/2003 | Kieval et al. |
| 6,542,781 B1 | 4/2003 | Koblish et al. |
| 6,562,034 B2 | 5/2003 | Edwards et al. |
| 6,616,624 B1 | 9/2003 | Kieval |
| 6,622,731 B2 | 9/2003 | Daniel et al. |
| 6,635,054 B2 | 10/2003 | Fjield et al. |
| 6,685,648 B2 | 2/2004 | Flaherty et al. |
| 6,711,444 B2 | 3/2004 | Koblish |
| 6,736,835 B2 | 5/2004 | Pellegrino et al. |
| 6,752,805 B2 | 6/2004 | Maguire et al. |
| 6,845,267 B2 | 1/2005 | Harrison et al. |
| 6,850,801 B2 | 2/2005 | Kieval et al. |
| 6,869,431 B2 | 3/2005 | Maguire et al. |
| 6,885,888 B2 | 4/2005 | Rezai |
| 6,893,436 B2 | 5/2005 | Woodard et al. |
| 6,939,346 B2 | 9/2005 | Kannenberg et al. |
| 7,149,574 B2 | 12/2006 | Yun et al. |
| 7,160,296 B2 | 1/2007 | Pearson et al. |
| 7,162,303 B2 | 1/2007 | Levin et al. |
| 7,221,979 B2 | 5/2007 | Zhou et al. |
| 7,381,200 B2 | 6/2008 | Katoh et al. |
| 7,390,894 B2 | 6/2008 | Weinshilboum et al. |
| 7,617,005 B2 | 11/2009 | Demarais et al. |
| 7,620,451 B2 | 11/2009 | Demarais et al. |
| 7,647,115 B2 | 1/2010 | Levin et al. |
| 7,653,438 B2 | 1/2010 | Deem et al. |
| 7,717,948 B2 | 5/2010 | Demarais et al. |
| 7,778,703 B2 | 8/2010 | Gross et al. |
| 8,131,371 B2 | 3/2012 | Demarals et al. |
| 8,131,372 B2 | 3/2012 | Levin et al. |
| 8,140,170 B2 | 3/2012 | Rezai et al. |
| 8,145,317 B2 | 3/2012 | Demarais et al. |
| 8,150,518 B2 | 4/2012 | Levin et al. |
| 8,150,519 B2 | 4/2012 | Demarais et al. |
| 8,150,520 B2 | 4/2012 | Demarais et al. |
| 8,175,711 B2 | 5/2012 | Demarais et al. |
| 8,702,619 B2 | 4/2014 | Wang |
| 8,768,470 B2 | 7/2014 | Deem et al. |
| 8,909,316 B2 | 12/2014 | Ng |
| 8,977,359 B2 | 3/2015 | Rossing |
| 9,002,446 B2 | 4/2015 | Wenzel et al. |
| 9,014,809 B2 | 4/2015 | Wenzel et al. |
| 9,014,821 B2 | 4/2015 | Wang |
| 2002/0087208 A1 | 7/2002 | Koblish et al. |
| 2002/0107515 A1 | 8/2002 | Edwards et al. |
| 2002/0139379 A1 | 10/2002 | Edwards et al. |
| 2002/0165532 A1 | 11/2002 | Hill et al. |
| 2002/0183682 A1 | 12/2002 | Darvish et al. |
| 2003/0050635 A1 | 3/2003 | Truckai et al. |
| 2003/0050681 A1 | 3/2003 | Pianca et al. |
| 2003/0060858 A1 | 3/2003 | Kieval et al. |
| 2003/0074039 A1 | 4/2003 | Puskas |
| 2003/0125790 A1 | 7/2003 | Fastovsky et al. |
| 2003/0181897 A1 | 9/2003 | Thomas et al. |
| 2003/0195507 A1 | 10/2003 | Stewart et al. |
| 2003/0199863 A1 | 10/2003 | Swanson et al. |
| 2003/0216792 A1 | 11/2003 | Levin et al. |
| 2003/0233099 A1 | 12/2003 | Danaek et al. |
| 2004/0010289 A1 | 1/2004 | Biggs et al. |
| 2004/0167509 A1 | 8/2004 | Taimisto |
| 2004/0215186 A1 | 10/2004 | Cornelius et al. |
| 2005/0080409 A1 | 4/2005 | Young et al. |
| 2005/0153379 A1* | 7/2005 | Hoon et al. ............ 435/7.92 |

(56) References Cited

U.S. PATENT DOCUMENTS

| | | |
|---|---|---|
| 2005/0187579 A1 | 8/2005 | Danek et al. |
| 2005/0228460 A1 | 10/2005 | Levin et al. |
| 2006/0085054 A1 | 4/2006 | Zikorus et al. |
| 2006/0095029 A1 | 5/2006 | Young et al. |
| 2006/0100618 A1 | 5/2006 | Chan et al. |
| 2006/0206150 A1 | 9/2006 | Demarais et al. |
| 2006/0212076 A1 | 9/2006 | Demarais et al. |
| 2006/0271111 A1 | 11/2006 | Demarais et al. |
| 2007/0129720 A1 | 6/2007 | Demarais et al. |
| 2007/0265687 A1 | 11/2007 | Deem et al. |
| 2008/0057590 A1* | 3/2008 | Urdea et al. ............ 436/71 |
| 2008/0319513 A1 | 12/2008 | Pu et al. |
| 2009/0024195 A1 | 1/2009 | Rezai et al. |
| 2009/0036948 A1 | 2/2009 | Levin et al. |
| 2010/0069888 A1 | 3/2010 | Solomon |
| 2010/0086948 A1* | 4/2010 | Gold et al. ............ 435/7.21 |
| 2010/0087716 A1 | 4/2010 | Nashed |
| 2010/0114244 A1* | 5/2010 | Manda et al. ............ 607/60 |
| 2010/0137860 A1 | 6/2010 | Demarais et al. |
| 2010/0137952 A1 | 6/2010 | Demarais et al. |
| 2010/0166739 A1* | 7/2010 | Chancellor et al. ....... 424/130.1 |
| 2010/0191112 A1 | 7/2010 | Demarais et al. |
| 2010/0222851 A1 | 9/2010 | Deem et al. |
| 2010/0222854 A1 | 9/2010 | Demarais et al. |
| 2010/0331833 A1 | 12/2010 | Maschke et al. |
| 2011/0060324 A1 | 3/2011 | Wu et al. |
| 2011/0112400 A1 | 5/2011 | Emery |
| 2011/0152759 A1 | 6/2011 | Clymer et al. |
| 2011/0160644 A1 | 6/2011 | Dacey, Jr. et al. |
| 2011/0178570 A1 | 7/2011 | Demarais |
| 2011/0184337 A1* | 7/2011 | Evans ............ A61M 25/0084 604/22 |
| 2011/0208096 A1* | 8/2011 | Demarais et al. ............ 601/3 |
| 2011/0270120 A1 | 11/2011 | McFarlin et al. |
| 2011/0306851 A1 | 12/2011 | Wang |
| 2012/0029504 A1 | 2/2012 | Afonso et al. |
| 2012/0116383 A1 | 5/2012 | Mauch et al. |
| 2012/0123400 A1 | 5/2012 | Francischelli et al. |
| 2012/0130289 A1 | 5/2012 | Demarais et al. |
| 2012/0130345 A1 | 5/2012 | Levin et al. |
| 2012/0172837 A1 | 7/2012 | Demarais et al. |
| 2012/0172870 A1 | 7/2012 | Jenson et al. |
| 2012/0191079 A1 | 7/2012 | Moll et al. |
| 2012/0296232 A1 | 11/2012 | Ng |
| 2012/0296329 A1 | 11/2012 | Ng |
| 2013/0085489 A1 | 4/2013 | Fain et al. |
| 2013/0123778 A1 | 5/2013 | Richardson et al. |
| 2013/0165764 A1 | 6/2013 | Scheuermann et al. |
| 2013/0172877 A1 | 7/2013 | Subramaniam et al. |
| 2013/0178750 A1 | 7/2013 | Sheehan et al. |
| 2013/0218029 A1 | 8/2013 | Cholette et al. |
| 2013/0237948 A1* | 9/2013 | Donders ............ A61N 1/36167 604/500 |
| 2013/0274614 A1 | 10/2013 | Shimada et al. |
| 2013/0282001 A1 | 10/2013 | Hezi-Yamit et al. |
| 2014/0012133 A1 | 1/2014 | Sverdlik et al. |
| 2014/0012242 A1 | 1/2014 | Lee et al. |
| 2014/0066803 A1 | 3/2014 | Choi |
| 2014/0073903 A1 | 3/2014 | Weber et al. |
| 2014/0074089 A1 | 3/2014 | Nishii |
| 2014/0128865 A1 | 5/2014 | Gross |
| 2014/0194866 A1 | 7/2014 | Wang |
| 2014/0213873 A1 | 7/2014 | Wang |
| 2014/0221805 A1 | 8/2014 | Wang |
| 2014/0236137 A1 | 8/2014 | Tran et al. |
| 2014/0236138 A1 | 8/2014 | Tran et al. |
| 2014/0246465 A1 | 9/2014 | Peterson et al. |
| 2014/0249524 A1 | 9/2014 | Kocur |
| 2014/0266235 A1 | 9/2014 | Mathur |
| 2014/0275924 A1 | 9/2014 | Min et al. |
| 2014/0276124 A1 | 9/2014 | Cholette et al. |
| 2014/0276733 A1 | 9/2014 | VanScoy et al. |
| 2014/0276742 A1 | 9/2014 | Nabutovsky et al. |
| 2014/0276746 A1 | 9/2014 | Nabutovsky et al. |
| 2014/0276755 A1 | 9/2014 | Cao et al. |
| 2014/0276762 A1 | 9/2014 | Parsonage |
| 2014/0276766 A1 | 9/2014 | Brotz et al. |
| 2014/0276767 A1 | 9/2014 | Brotz et al. |
| 2014/0276773 A1 | 9/2014 | Brotz et al. |
| 2014/0316400 A1 | 10/2014 | Blix et al. |
| 2014/0316496 A1 | 10/2014 | Masson et al. |
| 2014/0330267 A1 | 11/2014 | Harrington |
| 2014/0336637 A1 | 11/2014 | Agrawal et al. |
| 2015/0005764 A1 | 1/2015 | Hanson et al. |
| 2015/0025524 A1 | 1/2015 | Nabutovsky |
| 2015/0112329 A1 | 4/2015 | Ng |
| 2015/0223877 A1 | 8/2015 | Behar et al. |

FOREIGN PATENT DOCUMENTS

| | | |
|---|---|---|
| EP | 2316371 | 5/2011 |
| EP | 2594193 | 5/2013 |
| EP | 2613704 | 7/2013 |
| EP | 2747691 | 7/2014 |
| EP | 2797535 | 11/2014 |
| WO | WO-9407446 | 4/1994 |
| WO | WO-9525472 | 9/1995 |
| WO | WO-9531142 | 11/1995 |
| WO | WO-9736548 | 10/1997 |
| WO | WO-9900060 | 1/1999 |
| WO | WO-0122897 | 4/2001 |
| WO | WO-0170114 | 9/2001 |
| WO | WO-03022167 | 3/2003 |
| WO | WO-03/082080 | 10/2003 |
| WO | WO-2005030072 | 4/2005 |
| WO | WO-2005041748 | 5/2005 |
| WO | WO-2005110528 | 11/2005 |
| WO | WO-2006041881 | 4/2006 |
| WO | WO-2006105121 | 10/2006 |
| WO | WO-2007008954 | 1/2007 |
| WO | WO-2007078997 | 7/2007 |
| WO | WO-2008049084 | 4/2008 |
| WO | WO-2010078175 | 7/2010 |
| WO | WO-2012024543 | 2/2012 |
| WO | WO2012033974 | 3/2012 |
| WO | WO-2012158864 | 11/2012 |
| WO | WO-2013030738 | 3/2013 |
| WO | WO-2013030743 | 3/2013 |
| WO | WO2013074813 | 5/2013 |
| WO | WO2013101485 | 7/2013 |
| WO | WO-2013112844 | 8/2013 |
| WO | WO-2014012282 | 1/2014 |
| WO | WO-2014029355 | 2/2014 |
| WO | WO-2014059165 | 4/2014 |
| WO | WO-2014068577 | 5/2014 |
| WO | WO-2014091328 | 6/2014 |
| WO | WO-2014091401 | 6/2014 |
| WO | WO-2014149550 | 9/2014 |
| WO | WO-2014149552 | 9/2014 |
| WO | WO-2014149553 | 9/2014 |
| WO | WO-2014149690 | 9/2014 |
| WO | WO-2014150425 | 9/2014 |
| WO | WO-2014150432 | 9/2014 |
| WO | WO-2014150441 | 9/2014 |
| WO | WO-2014150455 | 9/2014 |
| WO | WO-2014158708 | 10/2014 |
| WO | WO-2014158713 | 10/2014 |
| WO | WO-2014163990 | 10/2014 |
| WO | WO-2014179768 | 11/2014 |
| WO | WO-2014182946 | 11/2014 |

OTHER PUBLICATIONS

Miller, Reed, "Finding a Future for Renal Denervation With Better Controlled Trials." Pharma & Medtech Business Intelligence, Article # 01141006003, Oct. 6, 2014, 4 pages.

Papademetriou, Vasilios, "Renal Denervation and Symplicity HTN-3: "Dubium Sapientiae Initium" (Doubt Is the Beginning of Wisdom)", Circulation Research, 2014; 115: 211-214.

Papademetriou, Vasilios et al., "Renal Nerve Ablation for Resistant Hypertension: How Did We Get Here, Present Status, and Future Directions." Circulation. 2014; 129: 1440-1450.

(56) References Cited

OTHER PUBLICATIONS

Papademetriou, Vasilios et al., "Catheter-Based Renal Denervation for Resistant Hypertension: 12-Month Results of the EnligHTN I First-in-Human Study Using a Multielectrode Ablation System." Hypertension. 2014; 64: 565-572.
Doumas, Michael et al., "Renal Nerve Ablation for Resistant Hypertension: The Dust Has Not Yet Settled." The Journal of Clinical Hypertension. 2014; vol. 16, No. 6, 2 pages.
Messerli, Franz H. et al. "Renal Denervation for Resistant Hypertension: Dead or Alive?" Healio: Cardiology today's Intervention, May/Jun. 2014, 2 pages.
Communication Relating to the Results of the Partial International Search Report for International App. No. PCT/US2013/030041, Date Mailed: Jun. 18, 2013, 8 pgs.
U.S. Appl. No. 95/002,110, filed Aug. 29, 2012, Demarais et al.
U.S. Appl. No. 95/002,209, filed Sep. 13, 2012, Levin et al.
U.S. Appl. No. 95/002,233, filed Sep. 13, 2012, Levin et al.
U.S. Appl. No. 95/002,243, filed Sep. 13, 2012, Levin et al.
U.S. Appl. No. 95/002,253, filed Sep. 13, 2012, Demarais et al.
U.S. Appl. No. 95/002,255, filed Sep. 13, 2012, Demarais et al.
U.S. Appl. No. 95/002,292, filed Sep. 14, 2012, Demarais et al.
U.S. Appl. No. 95/002,327, filed Sep. 14, 2012, Demarais et al.
U.S. Appl. No. 95/002,335, filed Sep. 14, 2012, Demarais et al.
U.S. Appl. No. 95/002,336, filed Sep. 14, 2012, Levin et al.
U.S. Appl. No. 95/002,356, filed Sep. 14, 2012, Demarais et al.
Benito, F., et al. "Radiofrequency catheter ablation of accessory pathways in infants." Heart, 78:160-162 (1997).
Dibona, G.F. "Sympathetic nervous system and kidney in hypertension." Nephrol and Hypertension, 11: 197-200 (2002).
Dubuc, M., et al., "Feasibility of cardiac cryoablation using a transvenous steerable electrode catheter." J Interv Cardiac Electrophysiol, 2:285-292 (1998).
Final Office Action; U.S. Appl. No. 12/827,700; Mailed on Feb. 5, 2013, 61 pages.
Gelfand, M., et al., "Treatment of renal failure and hypertension." U.S. Appl. No. 60/442,970, 2003.
Golwyn, D. H., Jr., et al. "Percutaneous Transcatheter Renal Ablation with Absolute Ethanol for Uncontrolled Hypertension or Nephrotic Syndrome: Results in 11 Patients with End-Stage Renal Disease." JVIR, 8: 527-533 (1997).
Hall, W. H., et al. "Combined embolization and percutaneous radiofrequency ablation of a solid renal tumor." *Am. J. Roentgenol*,174: 1592-1594 (2000).
Han, Y.-M, et al., "Renal artery ebolization with diluted hot contrast medium: An experimental study." J Vasc Interv Radiol, 12: 862-868 (2001).
Hansen, J. M., et al. "The transplanted human kidney does not achieve functional reinnervation." *Clin. Sci*, 87: 13-19 (1994).
Hendee, W. R. et al. "Use of Animals in Biomedical Research: The Challenge and Response." *American Medical Association White Paper* (1988).
Huang et al., "Renal denervation prevents and reverses hyperinsulinemia-induced hypertension in rats." Hypertension 32 (1998) pp. 249-254.
Kompanowska, E., et al., "Early Effects of renal denervation in the anaesthetised rat: Natriuresis and increased cortical blood flow." J Physiol, 531. 2:527-534 (2001).
Lee, S.J., et al. "Ultrasonic energy in endoscopic surgery." Yonsei Med J, 40:545-549 (1999).
Lustgarten, D.L.,et al., "Cryothermal ablation: Mechanism of tissue injury and current experience in the treatment of tachyarrhythmias." Progr Cardiovasc Dis, 41:481-498 (1999).
Medical-Dictionary.com, Definition of "Animal Model," http://medical-dictionary.com (search "Animal Model"), 2005.
Medtronic, Inc., Annual Report (Form 10-K) (Jun. 28, 2011).
Millard, F. C., et al, "Renal Embolization for ablation of function in renal failure and hypertension." Postgraduate Medical Journal, 65, 729-734, (1989).
Oliveira, V., et al., "Renal denervation normalizes pressure and baroreceptor reflex in high renin hypertension in conscious rats." Hypertension, 19:II-17-II-21 (1992).
Ong, K. L., et al. "Prevalence, Awareness, Treatment, and Control of Hypertension Among United States Adults 1999-2004." Hypertension, 49: 69-75 (2007) (originally published online Dec. 11, 2006).
Peet, M., "Hypertension and its Surgical Treatment by bilateral supradiaphragmatic splanchnicectomy" Am J Surgery (1948) pp. 48-68.
Renal Denervation (RDN), Symplicity RDN System Common Q&A (2011), http://www.medtronic.com/rdn/mediakit/RDN%20FAQ.pdf.
Schauerte, P., et al. "Catheter ablation of cardiac autonomic nerves for prevention of vagal atrial fibrillation." Circulation, 102:2774-2780 (2000).
Solis-Herruzo et al., "Effects of lumbar sympathetic block on kidney function in cirrhotic patients with hepatorenal syndrome," J. Hepatol. 5 (1987), pp. 167-173.
Stella, A., et al., "Effects of reversible renal deneravation on haemodynamic and excretory functions on the ipsilateral and contralateral kidney in the cat." Hypertension, 4:181-188 (1986).
Swartz, J.F., et al., "Radiofrequency endocardial cateheter ablation of accessory atrioventricular pathway atrial insertion sites." Circulation, 87: 487-499 (1993).
Uchida, F., et al., "Effect of radiofrequency catheter ablation on parasympathetic denervation: A comparison of three different ablation sites." PACE, 21:2517-2521 (1998).
Weinstock, M., et al., "Renal denervation prevents sodium rentention and hypertension in salt sensitive rabbits with genetic baroreflex impairment." Clinical Science, 90:287-293 (1996).
Wilcox, Josiah N., Scientific Basis Behind Renal Denervation for the Control of Hypertension, ICI 2012, Dec. 5-6, 2012.
Ahmed, Humera et al., Renal Sympathetic Denervation Using an Irrigated Radiofrequency Ablation Catheter for the Management of Drug-Resistant Hypertension, JACC Cardiovascular Interventions, vol. 5, No. 7, 2012, pp. 758-765.
Avitall et al., "The creation of linear contiguous lesions in the atria with an expandable loop catheter," Journal of the American College of Cardiology, 1999; 33; pp. 972-984.
Blessing, Erwin et al., Cardiac Ablation and Renal Denervation Systems Have Distinct Purposes and Different Technical Requirements, JACC Cardiovascular Interventions, vol. 6, No. 3, 2013.
ClinicalTrials.gov, Renal Denervation in Patients with uncontrolled Hypertension in Chinese (2011), www.clinicaltrials.gov/ct2/show/NCT01390831.
Excerpt of Operator's Manual of Boston Scientific's EPT-1000 XP Cardiac Ablation Controller & Accessories, Version of Apr. 2003, (6 pages).
Excerpt of Operator's Manual of Boston Scientific's Maestro 30000 Cardiac Ablation System, Version of Oct. 17, 2005 , (4 pages).
Schneider, Peter A., "Endovascular Skills—Guidewire and Catheter Skills for Endovascular Surgery," Second Edition Revised and Expanded, 10 pages, (2003).
Kandarpa, Krishna et al., "Handbook of Interventional Radiologic Procedures", Third Edition, pp. 194-210 (2002).
ThermoCool Irrigated Catheter and Integrated Ablation System, Biosense Webster (2006).
Mount Sinai School of Medicine clinical trial for Impact of Renal Sympathetic Denervation of Chronic Hypertenion, Mar. 2013, http://clinicaltrials.gov/ct2/show/NCT01628198.
Opposition to European Patent No. EP2092957, Granted Jan. 5, 2011, Date of Opposition Oct. 5, 2011, 26 pages.
Opposition to European Patent No. EP1802370, Granted Jan. 5, 2011, Date of Opposition Oct. 5, 2011, 20 pages.
Opposition to European Patent No. EP2037840, Granted Dec. 7, 2011, Date of Opposition Sep. 7, 2012, 25 pages.
Oz, Mehmet, Pressure Relief, TIME, Jan. 9, 2012, 2 pages. <www.time.come/time/printout/0,8816,2103278,00.html>.
Prochnau, Dirk et al., Catheter-based renal denervation for drug-resistant hypertension by using a standard electrophysiology catheter; Euro Intervention 2012, vol. 7, pp. 1077-1080.

(56) References Cited

OTHER PUBLICATIONS

Purerfellner, Helmut et al., Pulmonary Vein Stenosis Following Catheter Ablation of Atrial Fibrillation, Curr. Opin. Cardio. 20 : 484-490, 2005.
Papademetriou, Vasilios, Renal Sympathetic Denervation for the Treatment of Difficult-to-Control or Resistant Hypertension, Int. Journal of Hypertension, 2011, 8 pages.
Holmes et al., Pulmonary Vein Stenosis Complicating Ablation for Atrial Fibrillation: Clinical Spectrum and Interventional Considerations, JACC: Cardiovascular Interventions, 2: 4, 2009, 10 pages.
Purerfellner, Helmut et al., Incidence, Management, and Outcome in Significant Pulmonary Vein Stenosis Complicating Ablation for Atrial Fibrillation, Am. J. Cardiol , 93, Jun. 1, 2004, 4 pages.
Tsao, Hsuan-Ming, Evaluation of Pulmonary Vein Stenosis after Catheter Ablation of Atrial Fibrillation, Cardiac Electrophysiology Review, 6, 2002, 4 pages.
Wittkampf et al., "Control of radiofrequency lesion size by power regulation," Journal of the American Heart Associate, 1989, 80: pp. 962-968.
Zheng et al., "Comparison of the temperature profile and pathological effect at unipolar, bipolar and phased radiofrequency current configurations," Journal of Interventional Cardian Electrophysiology, 2001, pp. 401-410.
Abruzzo, Prowidenza et al., "Oxidative stress in the denervated muscle," Free Radical Research, vol. 44, No. 5, 2010, 563-576.
Amsellem S. et al., "Cubilin Is Essential for Albumin Reabsorption in the Renal Proximal Tubule," J Ann Soc Nephril, vol. 21, 2010,1859-1867.
Andres, Vicente, "Control of vascular cell pro;iferation and migration by cyclin-dependent kinase signalling: new perspectives and therapeutic potential," Cardiovascular Research, vol. 63, 2004, 11 pages.
Ankri, R. et al., "In-vivo Tumor detection using diffusion reflection measurements of targeted gold nanorods—a quantitative study," Biophotonics, 2012, 11 pages.
Bengatta, S. et al., "MMP9 and SCF Protect from Apoptosis in Acute Kidney Injury," J Am Soc Nephril, vol. 20, 2009, 787-797.
Bhattacharya, S. et al. "Role of p38 Protein Kinase in the Ligand-independent Ubiquitination and Down-regulation of the IFNAR1 Chain of Type I Interferon Receptor," The Journal of Biological Chemistry, vol. 286 No. 25, 2011, 22069-22076.
Bisoffi, M. et al., "Detection of viral bioagents using a shear horizontal surface acoustic wave biosensor," Biosensors and Bioelectronics, vol. 23, 2008, 7 pages.
Centi et al., "Strategies for electrochemical detection in immunochemistry," Bioanalysis, vol. 1. No. 7, 2009, 21 pages.
Dange, M. et al., "Each Conserved Active Site Tyr in the Three Subunits of Human Isocitrate Dehydrogenase Has a Different Function," The Journal of Biological Chemistry, vol. 285, No. 27, 2010, 6 pages.
Darisipudi, M. et al., "Dual Blockade of the Homeostatic Chemokine CXCL 12 and the Proinflammatory Chemokine CCL2 Has Addictive Protective Effects on Diabetic Kidney Disease," The American Journal of Pathology, vol. 179, No. 1, 2011, 9 pages.
Dhruvajyoti, R. et al., "Seeing and Counting Individual antigens Captured on a Microarrayed Soit with Force-Based Atomic Force Microscopy," Anal. Chem. vol. 82, 2010 6 pages.
Dikow, Ralf et al., "In Renal Transplants With Delayed Graft Function Chemokines and Chemokine Receptor Expression Predict Long-Term Allograft Function," Transplantation, vol. 90, 2010, 71-776.
Dinish, U. et al., "Highly sensitive SERS detection of cancer proteins in low sample volume using hollow core photonic crystal fiber," Biosens, Bioelecton, 2012, 6 pages.
Ford, M. et al., "Expression of fibroblast growth factors and their receptors in rat glomeruli," Kidney International, vol. 51, 1997, 10 pages.
Fragiadaki, Maria et al., "Interstitial fibrosis is associated with increased COL1A2 transcription in AA-injured renal tubular epithelial cells in vivo," Matrix Biology, vol. 30, 2011, 396-403.

Frostick, S. et al., "Schwann Cells, Neurotrophic Factors, and Peripheral Nerve Regeneration," Microsurgery, vol. 18, 1998, 9 pages.
Gaikwad, A. et al., "Epigenetic changes and alteration of Fbn1 and Col3A1 gene expression under hyperglycaemic and hyperinsulinaemic conditions," Biochem. J., vol. 432, 2010, 10 pages.
Green, H., et al., "Development of ERK Activity Sensor, an in vitro, FRET-based sensor of Extracellulat Regulated Kinase activity," BMC Chemical Biology, vol. 5, No. 1, 2005, 8 pages.
Grishman, Ellen et al., "Toll-like receptors, the NLRP3 inflammasome, and interleukin-1β in the development and progression of type 1 diabetes," Pediatric Research, vol. 71, No. 6, 2012, 7 pages.
Heberlein, Annemarie et al., BDNF plasma levels decrease during benzodiazepine withdrawal in patients suffering from comorbidity of depressive disorder and benzodiazepine dependence, Psychopharmacology, vol. 209, 2010, 3 pages.
Hervas, M. et al., "Electrochemical immunosensing on board microfluidic chip platforms," Trends in Analytical Chemistry, vol. 31, 2012, 20 pages.
Higgins, J, et al., "Gene Expression in the Normal Adult Human Kidney Assessed by Complementary DNA Microarray," Molecular Biology of the Cell, vol. 15, 2004, 649-656.
Hirst, E., "Bond-rupture immunosensors—A review," Biosensors and Bioelectronics, vol. 23, 2008, 10 pages.
Horke, S. et al., "Paraoxonase-2 Reduces Oxidative Stress in Vascular Cells and Decreases Endoplasmic Reticulum Stress-Induced Caspase Activation," Circulation, vol. 115, 2007, 11 pages.
Ihling, C. et al., "Endothelin-1 and Endothelin Converting Enzyme-1 in Human Atherosclerosis—Novel Targets for Pharmacotherapy in Atherosclerosis," Current Vascular Pharmacology, vol. 2, 2004, 10 pages.
Jacobs, C. et al., " Review: Carbon nanotube based electrochemical sensors for biomolecules," Analytical Chimica Acta, vol. 662, 2010, 23 pages.
Jin, Xinghua et al., "Delineation of apoptotic genes for synergistic apoptosis of lexatumumab and anthracyclines in human renal cell carcinoma cells by polymerase chain reaction array," Anti-Cancer Drugs, vol. 23, No. 4, 2012, 10 pages.
Johnson, B. et al., "Biosensing using dynamic-mode cantilever sensors: A review," Biosensors and Bioelectronics, vol. 32, 2012, 18 pages.
Kasuno, Kenji et al., "Clinical Application of Urinary Redox Regulating Protein," Thioredoxin, Rinsho Byori, vol. 59, 2011, 189-195.
Kerr, Heather et al., "Complement-mediated injury and protection of enforhelium: Lessons from atypical haemolytic uraemic syndrome," Immunobiology, vol. 217, 2012, 195-203.
Kinoshita, Yukiko et al., "Angiotensin II type I receptor blockade suppresses glomerular renin-angiotensin system activation, oxidative stress, and progressive glomerular injury in rat anti-glomerular basement membrane glomerulonephritis," Translational Research, vol. 158, No. 4, 2011, 15 pages.
Klosterhalfen, B. et al., "Influence of Heat Shock Protein 70 and Metallothionein Induction by Zinc-bis-(DL-Hydrogenaspartate) on the Release of Inflammatory Mediators in a Porcine Model of Recurrent Endotoxemia." Biochemical Pharmacology, vol. 52, 1996, 1201-1210.
Kopp, "Endothelin in the Control of Renal Sympathetic Nerve Activity," Contrib Nephrol. Basel, Karger, vol. 172, 2011, 107-119.
Kopp, Ulla C. et al., "Impaired Interaction Between Efferent and Afferent Renal Nerve Activity in SHR Involves Increased Activation of α2-Adrenoceptors," vol. 57, 2011, 640-647.
Kourtzelis, L., et al., "Complement anaphylatoxin C5a contributes to hemodialysis-associated thrombosis," Blood, 116, No. 4, 2010 9 pages.
Krukoff, Teresa L. et al., "Effects of renal denervation and reinnervation on ganglionic gene expression of neurotransmitter proteins and c-fos in rat," Molecular Brain Research, vol. 19, 1993, 6 pages.
Lan, Hui Yao, Transforming growth factor-β/Smad signalling in diabetic nephropathy, Clinical and Experimental Pharmacology and Physiology, vol. 39, 2012, 731-738.

(56) References Cited

OTHER PUBLICATIONS

Lantero, A. et al., "Transforming Growth Factor-β in Normal Nociceptive Processing and Pathological Pain Models," Mol Neurobiol, vol. 45, 2012, 76-86.
Lechner, Stefan et al., "Regulation of neuronal ion channels via P2Y receptors," Purinergic Signalling, vol. 1, 2004, 31-41.
Lee, Y. et al., "Fibromodulin Suppresses Nuclear Factor—κB Activity by Inducing the Delayed Degradation of IKBA via a JNK-dependent Pathway Coupled to Fibroblast Apoptosis," The Journal of Biological Chemistry, vol. 286, No. 8, 2011, 9 pages.
Leguillon-Buffello, D. et al., "An Alternative Quantitative Acoustical and Electrical Method for Detection of Cell Adhesion Process in Real-Time," Biotechnology and Bioengineering, vol. 108, No. 4, 2011, 16 pages.
Leonard, M., et al., "Reoxygenation-specific activation of the antioxidant transcription factor Nrf2 mediates cytoprotective gene expression in ischemia-reperfusion injury," The FASEB Journal, vol. 20, 2006, 3 pages.
Liang, W. et al., "A novel microfluidic immunoassay system based on electrochemical immunosensors: An application for the detection of NT-proBNP in whole blood," Biosensors and Bioelectronics, vol. 31, 2012, 6 pages.
Liu, Bin et al., "Role of cyclooxygenase-1-mediated prostacyclin synthesis in endothelium-dependent vasoconstrictor activity of porcine interlobular renal arteries," Am J Physiol Renal Physiol, vol. 302, 2012, F1133-F1140.
Liu, Y. et al., "BID Binds to Replication Protein A and Stimulates ATR Function following Replicative Stress," Molecular and Cellular Biology, vol. 31, No. 21, 2011, 12 pages.
Liu, Yanxin et al., "A novel SNP of the ATP1A1 gene is associated with heat tolerance traits in dairy cows," vol. 38, 2011, 83-88.
Liu, Ying et al., "Induction of KLF4 in response to heat stress," Cell Stress & Champerones, vol. 11, No. 4, 2006, 379-389.
Liu, Yong et al., "Renal Medullary MicroRNAs in Dahl Salt-Sensitive Rats: miR-29b Regulates Several Collagens and Related Genes," Hypertension, vol. 55, 2010, 974-982.
Lloyd-Burton, S. et al., "SPARC-Like 1 (SC1) Is a Diversely Expressed and Developmentally Regulated Matricellular Protein That Does Not Compensate for the Absence of SPARC in the CNS," The Journal of Comparative Neurology: Research in Systems Neuroscience, vol. 520, 2012, 2575-2590.
Lo, Denise et al., "Chemokines and their Receptors in Human Renal Allotransplantation," Transplantation, Author manuscript; available in PMC, 2012, 14 pages.
Longley, C. D. et al., "Proportions of Renal and Splenic Postganglionic Sympathetic Populations Containing Galanin and Dopamine Beta Hydroxylase," Neuroscience, vol. 55, No. 1, 1993, 9 pages.
Lu, X. et al., "The Role of Heat Shock Protein (HSP) in Atherosclerosis: Pathophysiology and Clinical Opportunities," Current Medicinal Chemistry, vol. 17, 2010, 957-973.
Luo, Lin, "Gene expression profiles of laser-captured adjacent neuronal subtypes," Nature Medicine, vol. 5, No. 1, 1999, 6 pages.
Ma, Frank, et al., "TGF-β1-activated kinase-1 regulated inflammation and fibrosis in the obstructed kidney," Am J. Physiol Renal Physiol, vol. 300, 2011, 12 pages.
Maeshima, A. et al., "Activin A: Autocrine Regulator of Kidney Development and Repair," Endocrine Journal, vol. 55, No. 1, 2008 9 pages.
Maity, Tapan et al., "Distinct, Gene Specific Effect of Heat Shock on Heat Shock Factor-1 Recruitment and Gene Expression of CXC Chemokine Genes," Cytokine, Author manuscript, available in PMC, 2012, 14 pages.
Mas, Valeria et al., "Gene Expression Patterns in Deceased Donor Kidneys Developing Delayed Graft Function After Kidney Transplantation," Transplantation, vol. 85, No. 4, 2008, 10 pages.
Mazanowska, O. et al. "Imbalance of Metallaproteinase/Tissue Inhibitors of Metalloproteinase System in Renal Transplant Recipients With Chronic Allograft Injury." Transplantation Proceedings, vol. 43, 2011, 4 pages.

Messina, G., et al., "Microfluidic immunosensor design for the quantification of interleukin-6 in human serum samples," Analytical Biochemistry, vol. 380, 2008, 6 pages.
Metters, J. et al., "New directions in screen printed elctroanalytical sensors: an overview of recent developments," Analyst, vol. 136, 2011, 10 pages.
Musial K., et al., "Heat shock proteins in chronic kidney disease," Journal of the International Pediatric Nephrology Association, 2010, 9 pages.
Nakaya, R. et al., "Identification of proteins that may directly interact with human RPA," J. Biochem, vol. 148, No. 5, 2010, 9 pages.
Nath, N. et al., "Evanescent wave fibre optic sensor for detection of L. donovani specific antibodies in sera of kala azar patients," Biosensors & Bioelectronics, 1996, 8 pages.
Obeidat, Motaz A., et al., "Post-transplant nuclear renal scans correlate with renal injury biomarkers and early allograft outcomes," Nephrol Dial Transplant, vol. 26, 2011, 8 pages.
Orellana G. et al., "New Trends in Fiber-Optic Chemical and Biological Sensors," Current Analytical Chemistry, vol. 4, 2008, 23 pages.
Pache, G. et al., "Upregulation of Id-1 via BMP-2 receptors induces reactive oxygen species in podocytes," Am J Physiol Renal Physiol, vol. 291, 2006, 9 pages.
Panini, N. et al., "Integrated microfluidoc systems with an immunosensor modified with carbon nanotubes for detection of prostate specific antigen (PSA) in human serum samples," Biosensors and Bioelectronics, vol. 23, 2008, 7 pages.
Paulis, L. et al., "Novel therapeutic targets for hypertension," Nature Reviews: Cardiology, vol. 7, 2010, 11 pages.
Pereira, Rui et al., "Neutrophil and monocyte activation in chronic kidney disease patients under hemodialysis and its relationship with resistance to recombinant human erythropoietin and to the hemodialysis procedure," Hemodialysis International, vol. 14, 2010, 7 pages.
Ransom, Richard F. et al., "Differential proteomic analysis of proteins induced by gluecocorticoids in cultured murine podocytes," Kidney International, vol. 67, 2005, 1275-1285.
Reich, Heather N. et al., "Molecular Markers of Injury in Kidney Biopsy Specimens of Patients with Lupus Nephritis," The Journal of Molecular Diagnostics, vol. 13, No. 2, 2011, 9 pages.
Romanenko, Aline et al., "p16$^{INK4A}$ and p15$^{INK4B}$ Gene Alteration Associated with Oxidative Stress in Renal Cell Carcinomas After the Chernobyl Accident (Pilot Study)," Diagnostic Molecular Pathology,vol. 11, No. 3, 2002, 163-169.
Ruotsalainen, V. et al., "Nephrin is specifically located at the slit diaphragm of glomerular podocytes," Proc. Natl. Acad. Sci. USA, vol. 96, 1999, 6 pages.
Rusling, J. et al., "Measurement of biomarker proteins for point-of-care early detection and monitoring of cancer," Analyst, Author manuscript, available in PMC, 2010, 31 pages.
Rusnati, M. et al., "Exploiting Surface Plasmon Resonance (SPR) Technology for the Identification of Fibroblast Growth Factor-2 (FGF2) Antagonists Endowed with Antiangiogenic Activity," Sensors, vol. 9, 2009, 33 pages.
Sadik, O. et al., "Status of biomolecular recognition using electrochemical techniques," Biosensors and Bioelectronics, vol. 24, 2009, 17 pages.
Saito, S. et al., "Analysis of glial cell line-derived neurotrophic factor-inducible zinc finger protein 1 expression in human diseased kidney," Human Pathology, col. 42, 2011, 11 pages.
Sataranatarajan, K. et al., "Regulation of Elongation Phase of mRNA Translation in Diabetic Nephropathy," The American Journal of Pathology, vol. 171, No. 6, 2007, 10 pages.
Sigdel, Tara K. et al., " Shotgun Proteomics Identifies Proteins Specific for Acute Renal Transplant Rejection," Proteomics Clin Appl. Author manuscript; available in PMC 2010, 27 pages.
Snigdha, Shikha et al., "Caspase-3 activation as a bifurcation point between plasticity and cell death," Neurosci Bull, vol. 28, No. 1, 2012, 11 pages.
Soleimani, M., "Dietary fructose, salt absorption and hypertension in metabolic syndrome: towards a new paradigm," Acta Physiol, vol. 201, 2011, 55-62.

(56) References Cited

OTHER PUBLICATIONS

Sonna, L. et al., "Molecular Biology of Thermoregulation Invited Review: Effects of heat and cold stress on mammalian gene expression," J Appl Physiol, vol. 92, No. 1725, 2002, 17-42.
Struckmann, Kirsten et al., "Impaired Expression of the Cell Cycle Regulator BTG2 Is Common in Clear Cell Renal Cell Carcinoma," Cancer Res, vol. 64, 2004, 1632-1638.
Su, Y. et al., "Chromatic immunoassay based on polydiacetylene vesicles," Colloids and Surfaces B: Biointerfaces, vol. 38, 2004, 5 pages.
Sun, A. et al., "Sensitive label-free electrochemical immunoassay based on a redox matrix of gold nanoparticles/Azure I/multi-wall carbon nanotubes composite," Biochemical Engineering Journal, vol. 57, 2011, 6 pages.
Sun, Dong et al., "Thronnbospondin-1 Short Hairpin RNA Suppresses Tubulointerstitial Fibrosis in the Kidney of Ureteral Obstruction by Ameliorating Peritubular Capillary Injury," Kidney Blood Press Res, vol. 35, 2012, 6 pages.
Tiniakos, D. et al, "Ontogeny of intrinsic innervation in the human kidney," Anat Embryol, vol. 209, 2004, 7 pages.
Todorov, Vladimir et al., "Differential Regulation of Cathepsin B and Prorenin Gene Expression in Renal Juxtaglomerular Cells," Kidney Blood Press Res, vol. 24, 2001, 4 pages.
Trimarchi, Hernan et al., "Proteinuria: an ignored marker of inflammation and cardiovascular disease in chronic hemodialysis," International Journal of Nephrology and Renovascular Disease, vol. 5, 2012, 7 pages.
Vivekanandan, A. et al., "Urine Glycoprotein Profile Reveals Novel Markers for Chronic Kidney Disease," International Journal of Proteomics, 2011, 18 pages.
Waalkes et al., "Fibronectin 1 mRNA expression correlates with advanced disease in renal cancer," Cancer, vol. 10, 2010, 6 pages.
Wang, Bao-Ying et al., Hepatotoxicity and gene expression downregulation of CYP isozymes caused by renal ischemia/reperfusion in the rat, Experimental and Toxicologic Pathology 61 (2009) 169-176.
Wong, Dona L. et al., "Adrenergic Responses to Stress: Transcriptional and Post-Transcriptional Changes," Ann N Y Acad Sci. Author manuscript; available in PMC, 2009, 10 pages.
Wu, Huiling et al., "TLR4 activation mediates kidney ischemia/reperfusion injury," The Journal of Clinical Investigation, vol. 117, No. 10, 2007, 2847-2859.
Xie, Chaoqin, "Ablation of Transient Receptor Potential Vanilloid 1 Abolishes Endothelin-Induced Increases in Afferent Renal Nerve Activity: Mechanisms and Functional Significance," Hypertension, vol. 54, 2009, 1298-1305.
Xie, Chaoqin, Interdependent Regulation of Afferent Renal Nerve Activity and Renal Function: Role of Transient Receptor Potential Vanilloid Type 1, Neurokinin 1, and Calcitonin Gene-Related Peptide Receptors, The Journal of Pharmacology and Experimental Therapeutics, vol. 325, No. 3, 7 pages.
Yoshino, Jun et al., "Leukemia Inhibitory Factor Is Involved in Tubular Regeneration after Experimental Acute Renal Failure," J Ann Soc Nephrol, vol. 14, 2003, 3090-3101.
Yuan, B. et al., "Gene expression reveals vulnerability to oxidative stress and interstitial fibrosis of renal outer medulla to nonhypertensive elevations of Ang II," Am J. Physiol Regul Integr Comp Physiol, vol. 284, 2003, 12 pages.
Zager, Richard et al., "Acute unilateral ischemic renal injury induces progressive renal inflammation, lipid accumulation, histone modification, and "end-stage" kidney disease," Am J Physiol Renal Physiol, vol. 301, 2011, 12 pages.
Zeisberg, Michael, "Bone morphogenic protein-7 and the kidney: current concepts and open questions," Nephrol Dial Transplant, vol. 21, 2006, 6 pages.
Zerega, Barbara et al., "Expression of NRL/NGAL (neu-related lipocalin/neutrophil gelatinase-associated lipocalin) during mammalian embryonic development and in Inflammation." European Journal of Cell Biology, vol. 79, 2000 8 pages.

Zhang, Weiru et al. "Interleukin 6 Underlies Angiotensin II- Induced Hypertension and Chronic Renal Damage," Hypertension, vol. 59, 2012, 136-144.
Zhao, Hongcheng et al., "Activation of the Transcription Factor Oct-1 in Response to DNA Damage," Cancer Res, vol. 60, 2000, 6 pages.
Staal, S.S., et al., "A Prefilled, Ready-to-Use, Electrophoresis-Based Lab-on-a-Chip Device for Monitoring Ions in Blood and Urine." 14th International Conference on Miniaturized Systems for Chemistry and Life Sciences, Oct. 3-7, 2010, Groningen, The Netherlands. 3 pages.
Rusling, James F., "Nanomaterials-Based Electrochemical Innnnunosensors for Proteins." The Chemical Record, 12 (1), Feb. 2012. 13 pages.
Yanase, Yuhki, et al., "Development of an Optical Fiber SPR Sensor for Living Cell Activation." Biosensors and Bioelectronics, 25 (5), Jan. 15, 2010, 16 pages.
Allen, E.V., Sympathectomy for essential hypertension, Circulation, 1952, 6:131-140.
Bello-Reuss, E. et al., "Effects of Acute Unilateral Renal Denervation in the Rat," Journal of Clinical Investigation, vol. 56, Jul. 1975, pp. 208-217.
Bello-Reuss, E. et al., "Effects of Renal Sympathetic Nerve Stimulation on Proximal Water and Sodium Reabsorption," Journal of Clinical Investigation, vol. 57, Apr. 1976, pp. 1104-1107.
Bhandari, A. and Ellias, M., "Loin Pain Hemaluria Syndrome: Pain Control with RFA to the Splanchanic Plexus," The Pain Clinc, 2000, vol. 12, No. 4, pp. 323-327.
Curtis, John J. et al., "Surgical Therapy for Persistent Hypertension After Renal Transplantation" Transplantation, 31:125-128 (1981).
Dibona, Gerald F. et al., "Neural Control of Renal Function," Physiological Reviews, vol. 77, No. 1, Jan. 1997, The American Physiological Society 1997, pp. 75-197.
Dibona, Gerald F., "Neural Control of the Kidney—Past, Present and Future," Nov. 4, 2002, Novartis Lecture, Hypertension 2003, 41 part 2, 2002 American Heart Association, Inc., pp. 621-624.
Janssen, Ben J.A. et al., "Effects of Complete Renal Denervation and Selective Afferent Renal Denervation on the Hypertension Induced by Intrarenal Norepinephrine Infusion in Conscious Rats", Journal of Hypertension 1989, 7: 447-455.
Katholi, Richard E., "Renal Nerves in the Pathogenesis of Hypertension in Experimental Animals and Humans," Am J. Physiol. vol. 245, 1983, the American Physiological Society 1983, pp. F1-F14.
Krum, Henry et al., "Catheter-Based Renal Sympathetic Denervation for Resistant Hypertension: A Mulitcentre Safety and Proof-of Principle Cohort Study," Lancet 2009; 373:1275-81.
Krum, et al., "Renal Sympathetic-Nerve Ablation for Uncontrolled Hypertension." New England Journal of Med, Aug. 2009, 361;9.
Luippold, Gerd et al., "Chronic Renal Denervation Prevents Glomerular Hyperfiltration in Diabetic Rats", Nephrol Dial Transplant, vol. 19, No. 2, 2004, pp. 342-347.
Mahfoud et al. "Treatment strategies for resistant arterial hypertension" Dtsch Arztebl Int. 2011;108:725-731.
Osborn, et al., "Effect of Renal Nerve Stimulation on Renal Blood Flow Autoregulation and Antinatriuresis During Reductions in Renal Perfusion Pressure," Proceedings of the Society for Experimental Biology and Medicine, vol. 168, 77-81, 1981.
Page, I.H. et al., "The Effect of Renal Denervation on Patients Suffering From Nephritis," Feb. 27, 1935;443-458.
Page, I.H. et al., "The Effect of Renal Denervation on the Level of Arterial Blood Pressure and Renal Function in Essential Hypertension," J. Clin Invest. 1934;14:27-30.
Rocha-Singh, "Catheter-Based Sympathetic Renal Denervation," Endovascular Today, Aug. 2009.
Schlaich, M.P. et al., "Renal Denervation as a Therapeutic Approach for Hypertension: Novel Implications for an Old Concept," Hypertension, 2009; 54:1195-1201.
Schlaich, M.P. et al., "Renal Sympathetic-Nerve Ablation for Uncontrolled Hypertension," N Engl J Med 2009; 361(9): 932-934.
Smithwick, R.H. et al., "Splanchnicectomy for Essential Hypertension," Journal Am Med Assn, 1953; 152:1501-1504.
Symplicity HTN-1 Investigators; Krum H, Barman N, Schlaich M, et al. Catheter-based renal sympathetic denervation for resistant

(56) References Cited

OTHER PUBLICATIONS hypertension: durability of blood pressure reduction out to 24 months. Hypertension. 2011;57(5):911-917.
Symplicity HTN-2 Investigators, "Renal Sympathetic Denervation in Patients with Treatment-Resistant Hypertension (The Symplicity HTN-2 Trial): A Randomised Controlled Trial"; Lancet, Dec. 4, 2010, vol. 376, pp. 1903-1909.
USRDS United States Renal Data System 2003 Annual Data Report.
Valente, John F. et al., "Laparoscopic Renal Denervation for Intractable ADPKD-Related Pain", Nephrol Dial Transplant (2001) 16:160.
Wagner, C.D. et al., "Very Low Frequency Oscillations in Arterial Blood Pressure After Autonomic Blockade in Conscious Dogs," Feb. 5, 1997, Am J Physiol Regul Integr Comp Physiol 1997, vol. 272, 1997 the American Physiological Society, pp. 2034-2039.
"2011 Edison Award Winners." Edison Awards: Honoring Innovations & Innovators, 2011, 6 pages, <http://www.edisonawards.com/BestNewProduct_2011.php>.
"2012 top 10 advances in heart disease and stroke research: American Heart Association/America Stroke Association Top 10 Research Report." American Heart Association, Dec. 17, 2012, 5 pages, <http://newsroom.heart.org/news/2012-top-10-advances-in-heart-241901>.
"Ardian(R) Receives 2010 EuroPCR Innovation Award and Demonstrates Further Durability of Renal Denervation Treatment for Hypertension." PR Newswire, Jun. 3, 2010, 2 pages, <http://www.prnewswire.com/news-releases/ardianr-receives-2010-europcr-innovation-award-and-demonstrates-further-durability-of-renal-denervation-treatment-for-hypertension-95545014.html>.
"Boston Scientific to Acquire Vessix Vascular, Inc.: Company to Strengthen Hypertension Program with Acquisition of Renal Denervation Technology." Boston Scientific: Advancing science for life—Investor Relations, Nov. 8, 2012, 2 pages, <http://phx.corporate-ir.net/phoenix.zhtml?c=62272&p=irol-newsArticle&id=1756108>.
"Cleveland Clinic Unveils Top 10 Medical Innovations for 2012: Experts Predict Ten Emerging Technologies that will Shape Health Care Next Year." Cleveland Clinic, Oct. 6, 2011, 2 pages. <http://my.clevelandclinic.org/media_relations/library/2011/2011-10-6-cleveland-clinic-unveils-top-10-medical-innovations-for-2012.aspx>.
"Does renal denervation represent a new treatment option for resistant hypertension?" Interventional News, Aug. 3, 2010, 2 pages. <http://www.cxvascular.com/in-latest-news/interventional-news---latest-news/does-renal-denervation-represent-a-new-treatment-option-for-resistant-hypertension>.
"Iberis—Renal Sympathetic Denervation System: Turning innovation into quality care." [Brochure], Terumo Europe N.V., 2013, Europe, 3 pages.
"Neurotech Reports Announces Winners of Gold Electrode Awards." Neurotech business report, 2009. 1 page. <http://www.neurotechreports.com/pages/goldelectrodes09.html>.
"Quick. Consistent. Controlled. OneShot renal Denervation System" [Brochure], Covidien: positive results for life, 2013, (n.l.), 4 pages.
"Renal Denervation Technology of Vessix Vascular, Inc. been acquired by Boston Scientific Corporation (BSX) to pay up to $425 Million." Vessix Vascular Pharmaceutical Intelligence: A blog specializing in Pharmaceutical Intelligence and Analytics, Nov. 8, 2012, 21 pages, <http://pharmaceuticalintelligence.com/tag/vessix-vascular/>.
"The Edison AwardsTM" Edison Awards: Honoring Innovations & Innovators, 2013, 2 pages, <http://www.edisonawards.com/Awards.php>.
"The Future of Renal denervation for the Treatment of Resistant Hypertension." St. Jude Medical, Inc., 2012, 12 pages.
"Vessix Renal Denervation System: So Advanced Its Simple." [Brochure], Boston Scientific: Advancing science for life, 2013, 6 pages.

Asbell, Penny, "Conductive Keratoplasty for the Correction of Hyperopia." Tr Am Ophth Soc, 2001, vol. 99, 10 pages.
Badoer, Emilio, "Cardiac afferents play the dominant role in renal nerve inhibition elicited by volume expansion in the rabbit." Am J Physiol Regul Integr Comp Physiol, vol. 274, 1998, 7 pages.
Bengel, Frank, "Serial Assessment of Sympathetic Reinnervation After Orthotopic Heart Transplantation: A longitudinal Study Using PET and C-11 Hydroxyephedrine." Circulation, vol. 99, 1999,7 pages.
Bettmann, Michael, Carotid Stenting and Angioplasty: A Statement for Healthcare Professionals From the Councils on Cardiovascular Radiology, Stroke, Cardio-Thoracic and Vascular Surgery, Epidemiology and Prevention, and Clinical Cardiology, American Heart Association, Circulation, vol. 97, 1998, 4 pages.
Bohm, Michael et al., "Rationale and design of a large registry on renal denervation: the Global SYMPLICITY registry." EuroIntervention, vol. 9, 2013, 9 pages.
Brosky, John, "EuroPCR 2013: CE-approved devices line up for renal denervation approval." Medical Device Daily, May 28, 2013, 3 pages, <http://www.medicaldevicedaily.com/servlet/com.accumedia.web.Dispatcher?next=bioWorldHeadlines_article&forceid=83002>.
Davis, Mark et al., "Effectiveness of Renal Denervation Therapy for Resistant Hypertension." Journal of the American College of Cardiology, vol. 62, No. 3, 2013, 11 pages.
Geisler, Benjamin et al., "Cost-Effectiveness and Clinical Effectiveness of Catheter-Based Renal Denervation for Resistant Hypertension." Journal of the American College of Cardiology, col. 60, No. 14, 2012, 7 pages.
Gertner, Jon, "Meet the Tech Duo That's Revitalizing the Medical Device Industry." FAST Company, Apr. 15, 2013, 6:00 AM, 17 pages, <http://www.fastcompany.com/3007845/meet-tech-duo-thats-revitalizing-medical-device-industry>.
Hering, Dagmara et al., "Chronic kidney disease: role of sympathetic nervous system activation and potential benefits of renal denervation." EuroIntervention, vol. 9, 2013, 9 pages.
Imimdtanz, "Medtronic awarded industry's highest honour for renal denervation system." The official blog of Medtronic Australasia, Nov. 12, 2012, 2 pages, <http://97waterlooroad.wordpress.com/2012/11/12/medtronic-awarded-industrys-highest-honour-for-renal-denervation-system/>.
Kaiser, Chris, AHA Lists Year's Big Advances in CV Research, medpage Today, Dec. 18, 2012, 4 pages, <http://www.medpagetoday.com/Cardiology/PCI/36509>.
Linz, Dominik et al., "Renal denervation suppresses ventricular arrhythmias during acute ventricular ischemia in pigs." Heart Rhythm, vol. 0, No. 0, 2013, 6 pages.
Mabin, Tom et al., "First experience with endovascular ultrasound renal denervation for the treatment of resistant hypertension." EuroIntervention, vol. 8, 2012, 5 pages.
Mahfoud, Felix et al., "Ambulatory Blood Pressure Changes after Renal Sympathetic Denervation in Patients with Resistant Hypertension." Circulation, 2013, 25 pages.
Mahfoud, Felix et al., "Expert consensus document from the European Society of Cardiology on catheter-based renal denervation." European Heart Journal, 2013, 9 pages.
Mahfoud, Felix et al., "Renal Hemodynamics and Renal Function After Catheter-Based Renal Sympathetic Denervation in Patients With Resistant Hypertension." Hypertension, 2012, 6 pages.
Ormiston, John et al., "First-in-human use of the OneShotTM renal denervation system from Covidien." EuroIntervention, vol. 8, 2013, 4 pages.
Ormiston, John et al., "Renal denervation for resistant hypertension using an irrigated radiofrequency balloon: 12-month results from the Renal Hypertension Ablation System (RHAS) trial." EuroIntervention, vol. 9, 2013, 5 pages.
Pedersen, Amanda, "TCT 2012: Renal denervation device makers play show and tell." Medical Device Daily, Oct. 26, 2012, 2 pages, <http://www.medicaldevicedaily.com/servlet/com.accumedia.web.Dispatcher?next=bioWorldHeadlines_article&forceid=80880>.
Schlaich, Markus et al., "Renal Denervation in Human Hypertension: Mechanisms, Current Findings, and Future Prospects." Curr Hypertens Rep, vol. 14, 2012, 7 pages.

(56) References Cited

OTHER PUBLICATIONS

Schmid, Axel et al., "Does Renal Artery Supply Indicate Treatment Success of Renal Denervation." Cardiovasc Intervent Radiol, vol. 36, 2013, 5 pages.
Schmieder, Roland E. et al., "Updated ESH position paper on interventional therapy of resistant hypertension." EuroIntervention, vol. 9, 2013, 9 pages.
Sievert, Horst, "Novelty Award EuroPCR 2010." Euro PCR, 2010, 15 pages.
Stouffer, G. A. et al., "Catheter-based renal denervation in the treatment of resistant hypertension." Journal of Molecular and Cellular Cardiology, vol. 62, 2013, 6 pages.
Verloop, W. L. et al., "Renal denervation: a new treatment option in resistant arterial hypertension." Neth Heart J., Nov. 30, 2012, 6 pages, <http://www.ncbi.nlm.nih.gov/pmc/articles/PMC3547427/>.
Worthley, Stephen et al., "Safety and efficacy of a multi-electrode renal sympathetic denervation system in resistant hypertension: the EnligHTN I trial." European Heart Journal, vol. 34, 2013, 9 pages.
Worthley, Stephen, "The St. Jude Renal Denervation System Technology and Clinical Review." The University of Adelaide Australia, 2012, 24 pages.
Zuern, Christine S., "Impaired Cardiac Baroflex Sensitivity Predicts Response to Renal Sympathetic Denervation in Patients with Resistant Hypertension." Journal of the American College of Cardiology, 2013, doi: 10.1016/j.jacc.2013.07.046, 24 pages.
Dorr et al., "Soluble fms-Like Tyrosine Kinase-1 and Endothelial Adhesion Molecules (Intercellular Cell Adhesion Molecule-1 and Vascular Cell Adhesion Molecule-1) as Predictive Markers for Blood Pressure Reduction After Renal Sympathetic Denervation." Hypertension, 2014, 63, pp. 984-990.
Chinushi et al., "Blood Pressure and Autonomic Responses to Electrical Stimulation of the Renal Arterial Nerves Before and After Ablation of the Renal Artery." Hypertension, 2013, 61, pp. 450-456.
Pokushalov et al., "A Randomized Comparison of Pulmonary Vein Isolation With Versus Without Concomitant Renal Artery Denervation in Patients With Refractory Symptomatic Atrial Fibrillation and Resistant Hypertension." Journal of the American College of Cardiology, 2012, 8 pages.
European Search Report for European Application No. 13159256, Date Mailed: Oct. 17, 2013, 6 pages.
International Search Report and Written Opinion for International App. No. PCT/US2013/030041, mailed Sep. 23, 2013, 20 pages.
Pieper et al., "Design and Implementation of a New Computerized System for Intraoperative Cardiac Mapping." Journal of Applied Physiology, 1991, vol. 71, No. 4, pp. 1529-1539.
Remo, Benjamin F. et al., "Safety and Efficacy of Renal Denervation as a Novel Treatment of Ventricular Tachycardia Storm in Patients with Cardiomyopathy." Heart Rhythm, 2014, 11(4), 541-6.
U.S. Appl. No. 60/852,787, filed Oct. 18, 2006, 112 pages.

\* cited by examiner

CAPTURE
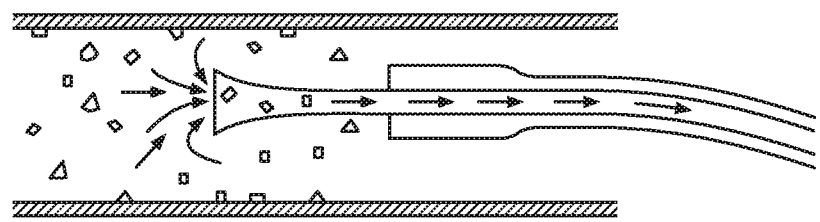
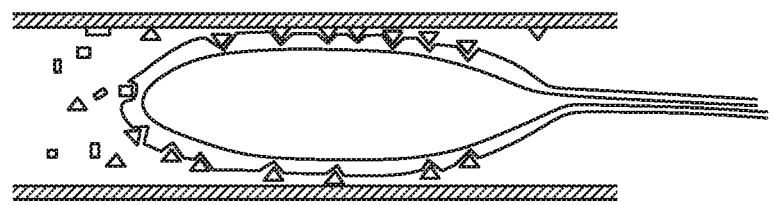
FIG. 8

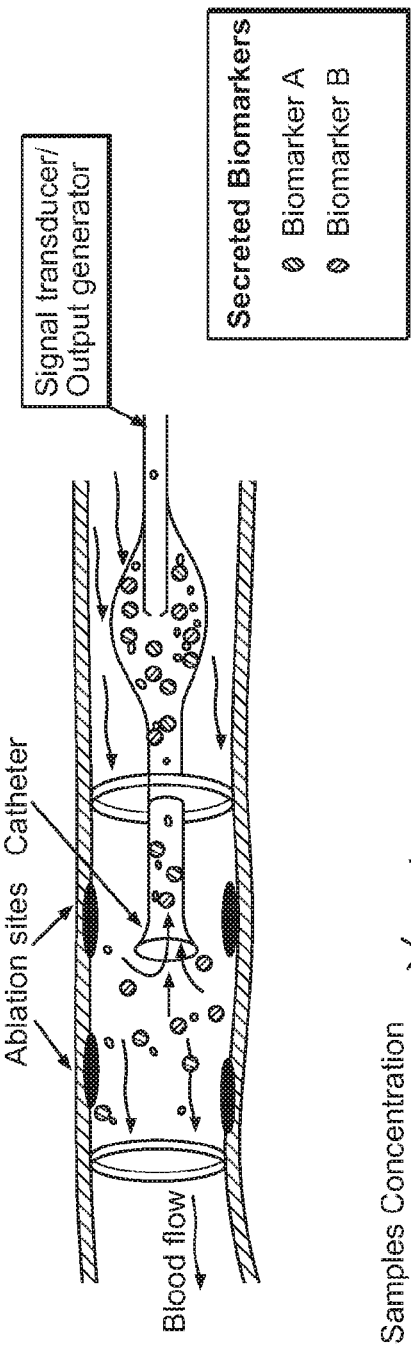
FIG. 9A  Sample Collection pre/post Ablation
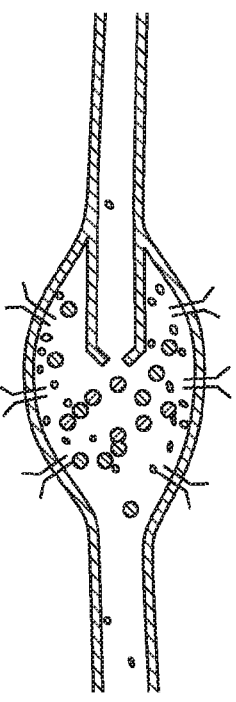
FIG. 9B  Samples Concentration
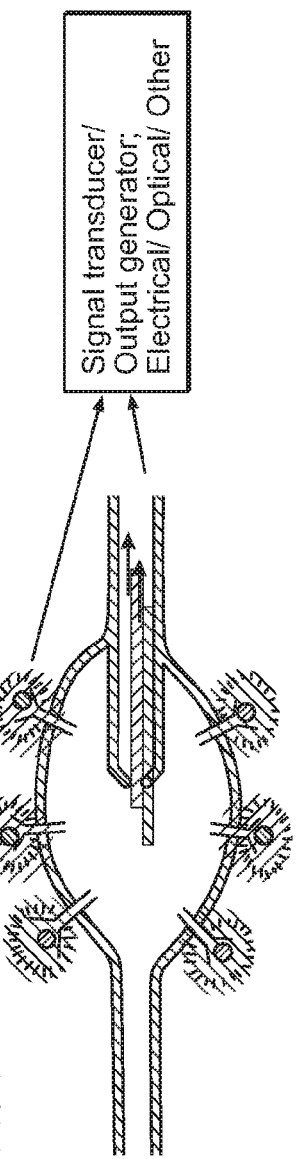
FIG. 9C  Signal detection

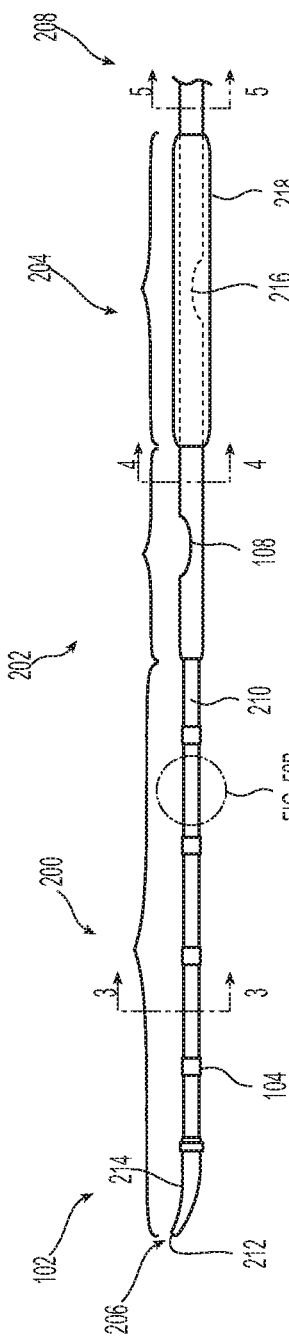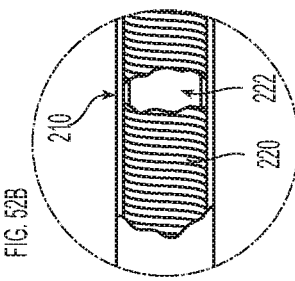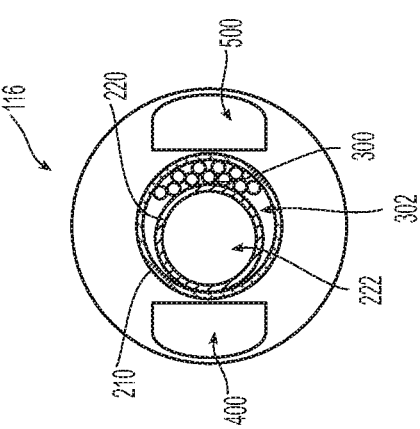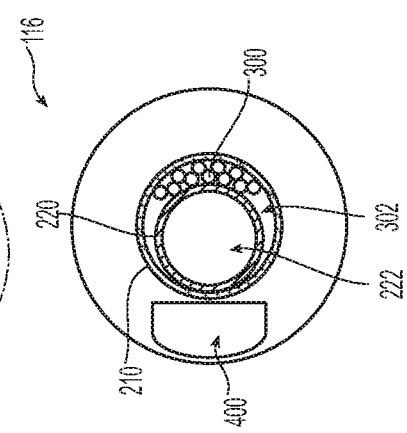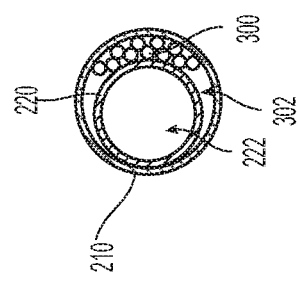

MONITORING OF NEUROMODULATION USING BIOMARKERS

CROSS-REFERENCE TO RELATED APPLICATIONS

The present application claims the benefit of the following applications:

(a) U.S. Provisional Application No. 61/608,625, filed Mar. 8, 2012;

(b) U.S. Provisional Application No. 61/608,626, filed Mar. 8, 2012; and (c) U.S. Provisional Application No. 61/746,528, filed Dec. 27, 2012.

All of the foregoing applications are incorporated herein by reference in their entireties. Further, components and features of embodiments disclosed in the applications incorporated by reference may be combined with various components and features disclosed and claimed in the present application.

ADDITIONAL APPLICATION(S) INCORPORATED BY REFERENCE

The following application is also incorporated herein by reference in its entirety:

U.S. patent application Ser. No. 13/791,751, entitled "BIOMARKER SAMPLING IN THE CONTEXT OF NEUROMODULATION DEVICES, SYSTEMS, AND METHODS," filed Mar. 8, 2013.

As such, components and features of embodiments disclosed in this application may be combined with various components and features disclosed in the present application.

BACKGROUND

The sympathetic nervous system (SNS) is a primarily involuntary bodily control system typically associated with stress responses. Fibers of the SNS innervate tissue in almost every organ system of the human body and can affect characteristics such as pupil diameter, gut motility, and urinary output. Such regulation can have adaptive utility in maintaining homeostasis or in preparing the body for rapid response to environmental factors. Chronic activation of the SNS, however, is a common maladaptive response that can drive the progression of many disease states. Excessive activation of the renal SNS in particular has been identified experimentally and in humans as a likely contributor to the complex pathophysiology of hypertension, states of volume overload (such as heart failure), and progressive renal disease. For example, radiotracer dilution has demonstrated increased renal norepinephrine (NE) spillover rates in patients with essential hypertension.

Cardio-renal sympathetic nerve hyperactivity can be particularly pronounced in patients with heart failure. For example, an exaggerated NE overflow from the heart and kidneys to plasma is often found in these patients. Heightened SNS activation commonly characterizes both chronic and end stage renal disease. In patients with end stage renal disease, NE plasma levels above the median have been demonstrated to be predictive for cardiovascular diseases and several causes of death. This is also true for patients suffering from diabetic or contrast nephropathy. Evidence suggests that sensory afferent signals originating from diseased kidneys are major contributors to initiating and sustaining elevated central sympathetic outflow.

The renal sympathetic nerves arise from T10-L2 and follow the renal artery to the kidney. The sympathetic nerves innervating the kidneys terminate in the blood vessels, the juxtaglomerular apparatus, and the renal tubules. Stimulation of renal efferent nerves results in increased renin release (and subsequent renin-angiotensin-aldosterone system (RAAS) activation) and sodium retention and decreased renal blood flow. These neural regulation components of renal function are considerably stimulated in disease states characterized by heightened sympathetic tone and likely contribute to increased blood pressure in hypertensive patients. The reduction of renal blood flow and glomerular filtration rate as a result of renal sympathetic efferent stimulation is likely a cornerstone of the loss of renal function in cardio-renal syndrome (i.e., renal dysfunction as a progressive complication of chronic heart failure). Pharmacologic strategies to thwart the consequences of renal efferent sympathetic stimulation include centrally acting sympatholytic drugs, beta blockers (intended to reduce renin release), angiotensin converting enzyme inhibitors and receptor blockers (intended to block the action of angiotensin II and aldosterone activation consequent to renin release), and diuretics (intended to counter the renal sympathetic mediated sodium and water retention). These pharmacologic strategies, however, have significant limitations including limited efficacy, compliance issues, side effects, and others.

BRIEF DESCRIPTION OF DRAWINGS

FIG. 8: Illustrative target biomarker capture methods: (a) removal from neuromodulation site and sequestration in a capture compartment for analysis in vivo or ex vivo (upper panel) and (b) balloon-based/semi-permeable filtering device with antibody based/immuno-electrochemical technology embedded within for capture and analysis in vivo or ex vivo (lower panel).

FIGS. 9A-C: Representative embodiment of protein target biomarker detection method and device.

FIG. 52: A. Enlarged side view illustrating a neuromodulation and sampling assembly of the treatment device of FIG. 51 configured in accordance with an embodiment of the present technology. B. Further enlarged cut-away view of a portion of the neuromodulation and sampling assembly of (A) in accordance with an embodiment of the present technology.

FIG. 53: Cross-sectional end view taken along lines 2-2 in FIG. 52A.

FIG. 54: Cross-sectional end view taken along lines 3-3 in FIG. 52A.

FIG. 55: Cross-sectional end view taken along lines 4-4 in FIG. 52A.

DETAILED DESCRIPTION

Figure 1:
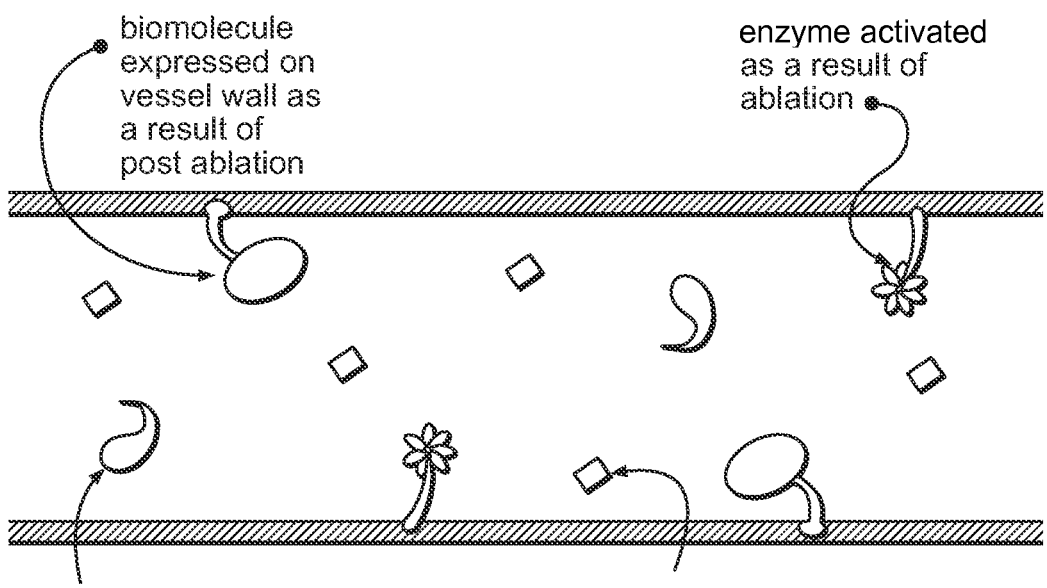
FIG. 1: Illustration of potential target biomarkers for rapid monitoring of renal neuromodulation: artery wall proteins, secreted proteins, enzymes activated as a result of denervation, and secreted small molecules.

The present technology is directed to methods, systems, devices, compositions, and kits for monitoring neuromodulation efficacy by detecting changes in the level or activity of one or more target biomarkers, as well as methods, systems, compositions, and kits for determining biomarker activity in a patient. Specific details of several embodiments of the technology are described below with reference to FIGS. 1-56D. Although many of the embodiments are described below with respect to methods, systems, devices, compositions, and kits for monitoring renal neuromodulation efficacy, other applications (e.g., monitoring nerve activity in the absence of neuromodulation) and other embodiments in addition to those described herein are within the scope of the technology. Additionally, several other embodiments of the technology can have different configurations, components, or procedures than those described herein. A person of ordinary skill in the art, therefore, will accordingly understand that the technology can have other embodiments with additional elements, or the technology can have other embodiments without several of the features shown and described below with reference to FIGS. 1-56D.

Several current methods for neuromodulation would benefit from a process for rapid evaluation of success of the procedure. Examples of neuromodulation methods that may benefit from rapid evaluation methods include renal denervation, for example to treat clinical conditions characterized by increased overall and particularly renal sympathetic activity such as hypertension, metabolic syndrome, insulin resistance, diabetes, left ventricular hypertrophy, chronic end stage renal disease, inappropriate fluid retention in heart failure, cardio-renal syndrome, osteoporosis, and sudden death.

Efficacy of many current renal neuromodulation methods is evaluated after the procedure has been completed by monitoring blood pressure, but statistically meaningful changes in blood pressure may not be observed until about 2 weeks, 4 weeks, 3 months, 6 months, or more after completion. In the absence of real-time or at least relatively contemporaneous feedback (e.g., less than about 30 minutes), physicians may miss nerves (i.e., under ablate) with unconventional nerve anatomy or, alternatively, err on the side of over-ablation.

Disclosed herein are several embodiments of methods and processes for monitoring neuromodulation efficacy by detecting changes in the level or activity of one or more target biomarkers associated with neuromodulation, as well as methods and processes of performing neuromodulation that incorporate monitoring of neuromodulation efficacy based on changes in level or activity of one or more target biomarkers. In contrast with many conventional approaches, the disclosed methods are expected to allow for real-time or relatively contemporaneous monitoring of neuromodulation efficacy. In certain embodiments, these methods and processes are used to monitor the efficacy of renal neuromodulation. Also provided herein are methods of treating hypertension in a subject in need thereof using renal neuromodulation, wherein the methods include steps for monitoring the efficacy of the neuromodulation procedure by detecting changes in the level or activity of one or more target biomarkers associated with neuromodulation. Further provided herein are devices, compositions, and kits for use in conjunction with the disclosed methods.

"Neuromodulation" is the partial or complete incapacitation or effective disruption of one or more nerves. Such incapacitation or disruption can be long term (e.g., permanent or for periods of months or years) or short term (e.g., for periods of minutes, hours, days, or weeks). "Renal neuromodulation" is the partial or complete incapacitation or effective disruption of the nerves of the kidneys, including nerves terminating in the kidneys or in structures closely associated with the kidneys. Renal neuromodulation is expected to efficaciously treat several clinical conditions characterized by increased overall sympathetic activity, and, in particular, conditions associated with central sympathetic overstimulation such as hypertension, heart failure, acute myocardial infarction, metabolic syndrome, insulin resistance, diabetes, left ventricular hypertrophy, chronic and end stage renal disease, inappropriate fluid retention in heart failure, cardio-renal syndrome, osteoporosis, and sudden death, among others. The reduction of afferent neural signals typically contributes to the systemic reduction of sympathetic tone/drive, and renal neuromodulation is expected to be useful in treating several conditions associated with systemic sympathetic overactivity or hyperactivity.

Several embodiments of methods for monitoring neuromodulation efficacy by detecting changes in the level or activity of one or more target biomarkers in accordance with the present technology are described herein. In certain embodiments, these methods can be used to determine whether a neuromodulation procedure was successful, i.e., whether the procedure resulted in partial or complete incapacitation or effective disruption of one or more target nerves. In certain embodiments, these methods include (a) determining a baseline level or activity of one or more target biomarkers; (b) performing the neuromodulation procedure; (c) determining a post-neuromodulation level or activity for the target biomarker(s); and (d) comparing the post-neuromodulation level or activity to the baseline level or activity, wherein the neuromodulation procedure is classified as successful if the post-neuromodulation level or activity differs significantly from the baseline level or activity. In certain embodiments, a significant difference in level or activity means a difference of 1% or greater, for example 2% or greater, 3% or greater, 4% or greater, 5% or greater, 10% or greater, 20% or greater, or 50% or greater. In other embodiments, a significant difference in level or activity means a difference of 2-fold or greater, for example 3-fold or greater, 4-fold or greater, or 5-fold or greater. In other embodiments, these methods include (a) performing the neuromodulation procedure; (b) determining a post-neuromodulation level or activity for one or more target biomarkers; and (c) comparing the post-neuromodulation level or activity to a pre-determined threshold level or activity, wherein the neuromodulation procedure is classified as successful if the post-neuromodulation level or activity is greater than the pre-determined threshold level or activity. In still other embodiments, these methods include (a) performing the neuromodulation procedure; (b) determining a post-neuromodulation level or activity for one or more target biomarkers; and (c) comparing the post-neuromodulation level or activity to a pre-determined range of level or activity, wherein the neuromodulation procedure is classified as successful if the post-neuromodulation level or activity falls within the pre-determined range of level or activity. In certain embodiments, post-neuromodulation target biomarker level or activity is determined in an acute timeframe, e.g., within 30 minutes or less following denervation, thereby allowing neuromodulation efficacy to be assessed while a subject is still catheterized. In other embodiments, however, post-neuromodulation target biomarker level or activity may be measured in a chronic timeframe, e.g., within several hours, days, weeks, or months following denervation. In certain embodiments, the methods provided herein include (a) determining a baseline level or activity of one or more target biomarkers, (b) at least partially inhibiting sympathetic neural activity in a renal nerve of the subject via a neuromodulation assembly (discussed in more detail below), (c) determining a post-neuromodulation level or activity for the target biomarker(s), and (d) comparing the post-neuromodulation level or activity to the baseline level or activity, wherein the neuromodulation procedure is classified as successful if the post-neuromodulation level or activity differs significantly from the baseline level or activity.

Also described herein are several embodiments of methods for determining biomarker activity in a patient in accordance with the present technology. In certain of these embodiments, these methods include (a) transluminally positioning an energy delivery element of a catheter within a target blood vessel of a patient and adjacent to target neural fibers, (b) at least partially ablating the target neural fibers via the energy delivery element, (c) capturing a plurality of at least one type of biomarker in a capture compartment of the catheter, wherein the biomarker is secreted as a result of the ablation procedure, (d) sequestering the plurality of the at least one type of biomarker in the capture compartment to concentrate the biomarker, (e) binding the biomarker to at least one immobilized capture agent disposed on an inner surface of the capture compartment, and (f) detecting a concentration of the biomarker, wherein the concentration corresponds, at least in part, to a degree of ablation of the target neural fibers.

Target biomarker(s) for use in conjunction with the methods disclosed herein may be any biomolecule that exhibits a quantitative and detectable change in level or activity following neuromodulation in a desired manner. In certain embodiments, target biomarkers may be proteins or fragments thereof. In these embodiments, a change in protein level may refer to a change in expression (as measured by mRNA or protein level) or secretion. In other embodiments, target biomarkers may be small molecules, peptides, or other non-protein compounds. Provided in certain embodiments are compositions and kits comprising one or more target biomarkers for use in the methods disclosed herein.

In those embodiments that utilize protein target biomarkers, the target biomarkers may be one or more proteins implicated in a cell death, apoptosis, metabolic modulation, oxidative stress, or neuro-endothelial cross-talk pathway, or proteins involved in neuromodulation, hormone modulation, neuronal stress response, neuronal regeneration, endothelial vasodilation or vasoconstriction, modulation of efferent and afferent sympathetic activation, or regulation of catecholamine production. Specific classes of proteins that may be utilized as target biomarkers in conjunction with the methods disclosed herein include but are not limited to endothelins, neurotrophins, vasoconstrictive proteins, cell surface receptors, heatshock proteins or modified heatshock proteins, secreted inflammatory cytokines or chemokines, and proteins from the renin-angiotensin system. Protein target biomarkers for use in the present methods may be cell surface proteins, secreted proteins, or intracellular proteins. In certain of these embodiments, the protein can be a cell surface receptor expressed on a vessel wall, a secreted protein that exhibits increased or decreased secretion levels post-ablation, and/or an enzyme that exhibits increased or decreased activity post-ablation (see, e.g., FIG. 1).

In those embodiments that utilize non-protein target biomarkers, the target biomarkers may be small molecules such as catecholamines or other neurotransmitters (particularly those associated with sympathetic nervous activity) such as NE, neuropeptide Y (NPY) epinephrine, or dopamine, secreted hormonal or other soluble endocrine molecules, or secreted metabolites or cellular debris.

In certain embodiments of the methods disclosed herein, a change in target biomarker level or activity occurs at or near a neuromodulation site (e.g., at or near an ablation site). In these embodiments, the change can be measured at or near the neuromodulation site or in a biological sample obtained from at or near the neuromodulation site. For example, where neuromodulation is carried out at or near the kidney (e.g., in the renal artery), changes in target biomarker level or activity may be measured in a biological sample obtained from at or near the kidney. A "biological sample" as used herein may refer to any bodily fluid (e.g., blood, plasma, urine, etc.) or tissue that may contain one or more target biomarkers. Therefore, a biological sample obtained from at or near the kidney may be blood or tissue from the renal arteries, renal veins, or elsewhere in the renal system. A target biomarker associated with renal neuromodulation may exhibit changes in expression or activity at any or all of these locations. Alternatively or in addition to locally measurable changes in level or activity, in certain embodiments the target biomarkers may exhibit changes in level or activity at locations remote to the neuromodulation site. In these embodiments, target biomarker collection may take place systemically, for example by collecting a blood or urine sample. In certain embodiments, local target biomarker collection may be preferred to systemic collection because it provides a higher concentration of target biomarker and may allow for more rapid or accurate results than systemic collection. In other embodiments, there may be no preference between local and systemic collection, or systemic collection may be preferred, for example due to ease of collection.

Figure 2:
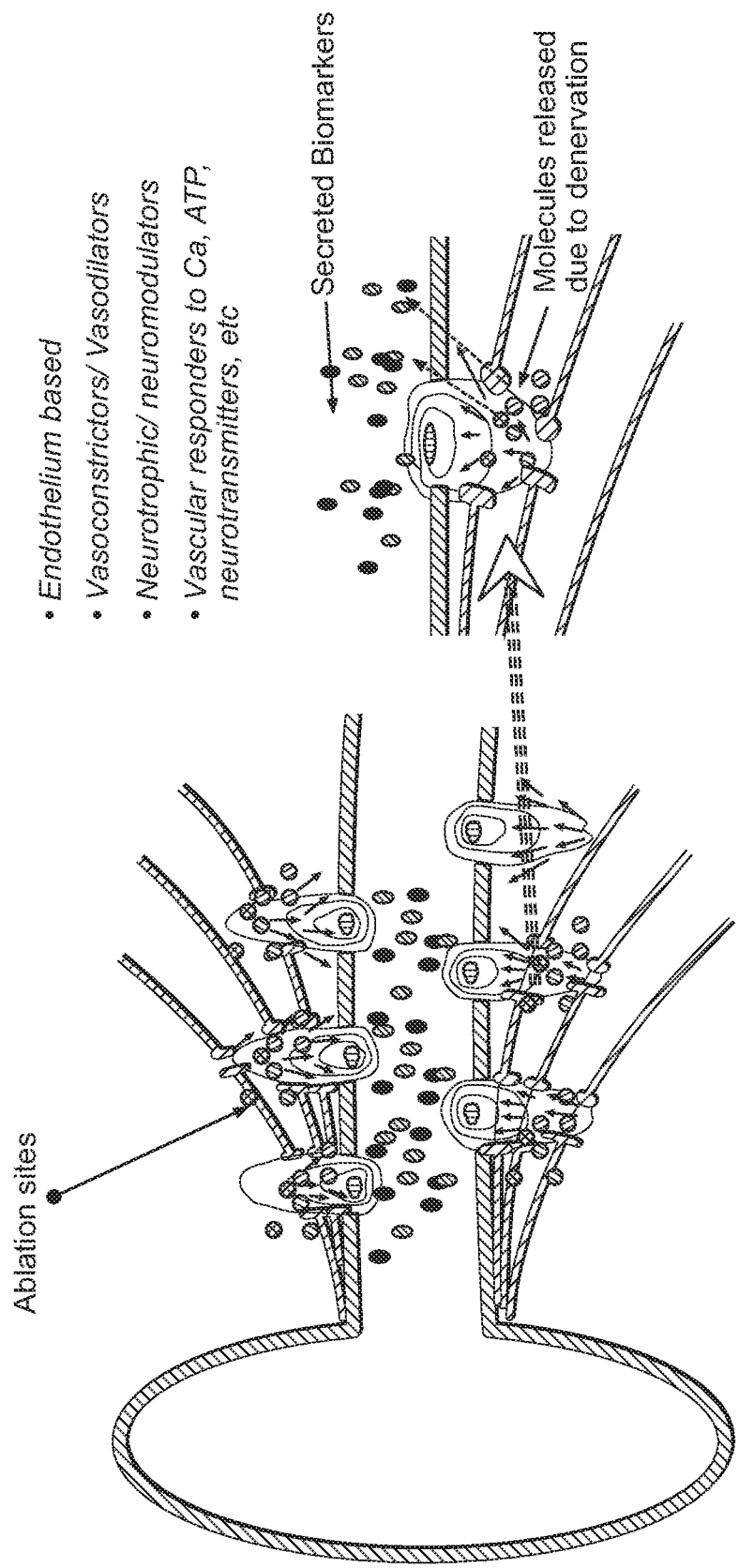
FIG. 2: Illustration of target biomarkers exhibiting changes in level or activity as a result of vascular-neuronal cross-talk.
Figure 3:
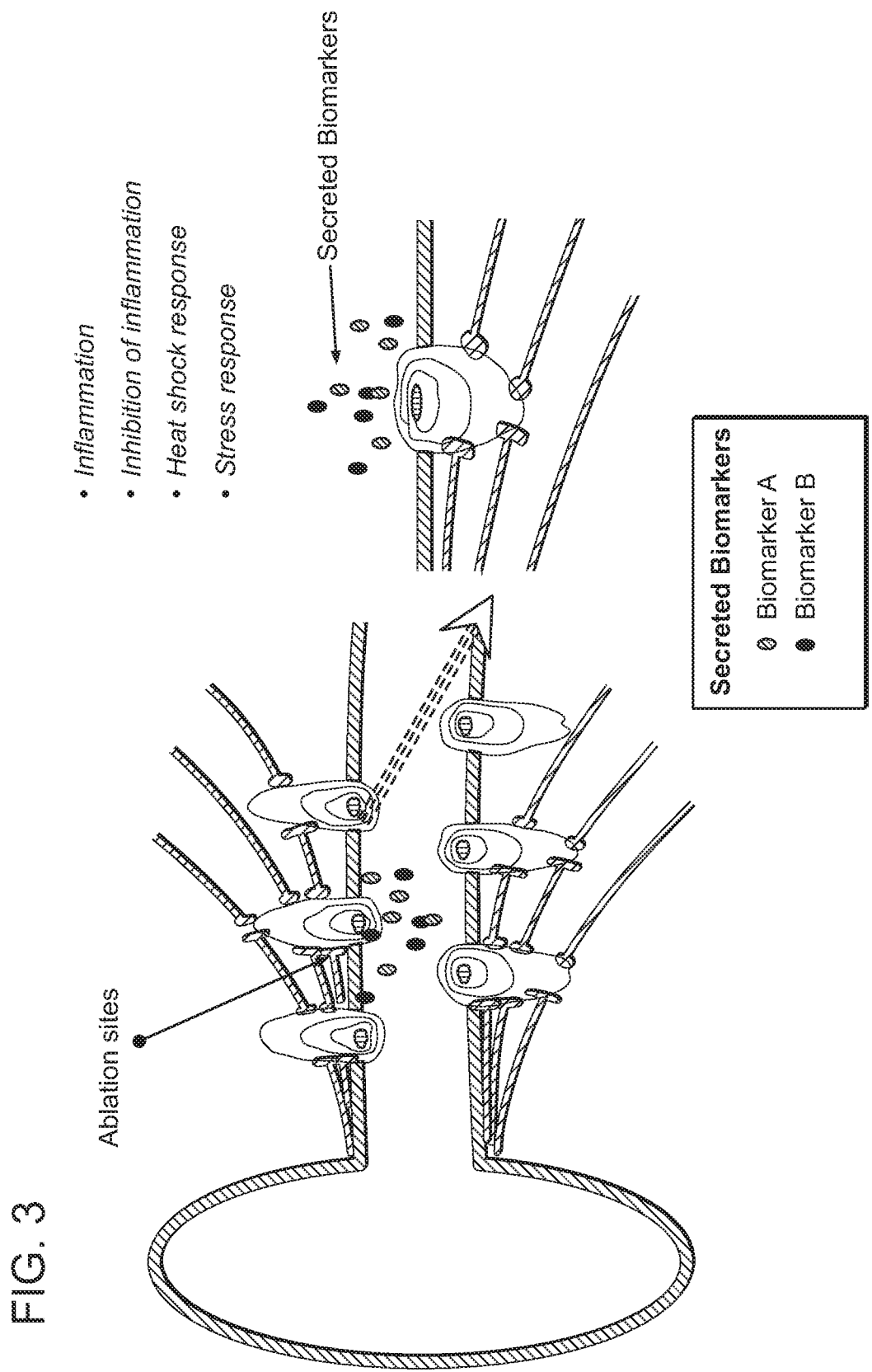
FIG. 3: Illustration of target biomarkers exhibiting changes in level or activity as a surrogate response to neuromodulation (e.g., as a response to RF).

Target biomarkers for use in the methods disclosed herein may exhibit a change in level or activity that correlates with nerve ablation and/or NE levels, for example nerve ablation and/or NE levels in the kidney. In certain embodiments, changes in the level or activity of a target biomarker may be a direct result of neuromodulation, e.g., a direct response to neuronal damage. In certain of these embodiments, the target biomarker may exhibit changes in activity or level as a result of vascular-neuronal cross-talk (see, e.g., FIG. 2). For example, the target biomarker may be an endothelium-based target biomarker, vasoconstrictor, vasodilator, neuromodulator, neurotrophic factor, catecholamine, or vascular responder to signaling molecules such as ATP, neurotransmitters, or calcium that exhibits increased or decreased levels as a direct result of neuromodulation. Changes in the level or activity of a target biomarker may be indicative of a synaptic discharge of substances such as small molecules (e.g., calcium) or neurotransmitters as a result of axonal damage, axonal stress, or axotectomy. For example, sympathetic denervation might result in discharge of NE, NPY, or dopamine reserves at the synaptic ends in the kidney, resulting in a burst that can be collected and detected from renal arterial or venous blood or elsewhere such as in systemic blood or urine. In other embodiments, changes in the level or activity of a target biomarker may be an indirect/surrogate response to the neuromodulation procedure (see, e.g., FIG. 3). For example, a target biomarker may be a protein such as an inflammatory or anti-inflammatory pathway, heat shock response pathway, or stress response pathway protein that exhibits a change in level or activity in response to RF exposure or changes in temperature at or near an ablation site.

In certain embodiments of the methods disclosed herein, neuromodulation efficacy is monitored by detecting changes in the level or activity of a single target biomarker. In other embodiments, efficacy is monitored by detecting changes in the level or activity of two or more target biomarkers. In certain of these embodiments, neuromodulation is classified as successful if each of the target biomarkers exhibits a change in level or activity. In other embodiments, neuromodulation is classified as successful if a threshold number or a specific subset or combination of target biomarkers exhibits a change in level or activity. In those embodiments that utilize two or more target biomarkers, the target biomarkers may be all proteins, all non-proteins, or a combination of proteins and non-proteins.

In certain embodiments of the methods disclosed herein, baseline level or activity of a target biomarker is derived from the subject undergoing neuromodulation. For example, target biomarker level or activity may be measured in the subject at one or more timepoints before neuromodulation. The baseline value may represent target biomarker level or activity at a specific timepoint before neuromodulation, or it may represent an average level or activity at two or more timepoints before neuromodulation. In certain preferred embodiments, a baseline value is based on target biomarker level or activity immediately before neuromodulation (i.e., after the subject has already been catheterized). Alternatively, a baseline value for a particular target biomarker may be derived from a standard value for that target biomarker across the population as a whole or across a particular subpopulation. In certain embodiments, the baseline level or activity of a target biomarker is determined using the same method that is subsequently used to determine the post-neuromodulation level or activity of the target biomarker. In certain embodiments, changes in target biomarker level or activity are calculated based on the difference between baseline level or activity and post-neuromodulation level or activity. For example, the differential (delta) in target biomarker expression levels can be the difference between target biomarker expression at a specific timepoint pre- and post-neuromodulation.

Target biomarkers for use in the methods disclosed herein may exhibit a two-fold or greater change in level or activity in response to neuromodulation. For example, a target biomarker may be a protein that exhibits a two-fold or greater increase or decrease in expression or secretion following neuromodulation. In certain of these embodiments, a target biomarker exhibits a three-fold or greater, five-fold or greater, or ten-fold or greater change in level or activity in response to neuromodulation.

In certain embodiments, target biomarkers for use in the methods disclosed herein exhibit a change in level or activity within a predetermined timeframe post-neuromodulation. In certain embodiments, the methods provided herein allow for real-time or relatively contemporaneous monitoring of neuromodulation efficacy. Accordingly, certain target biomarkers for use in the methods disclosed herein may exhibit a change in level or activity at the time of neuromodulation or relatively contemporaneous to neuromodulation. For example, in certain embodiments a target biomarker exhibits a change in level or activity within 1 minute, 2 minutes, 5 minutes, 10 minutes, 15 minutes, or 30 minutes of neuromodulation. Accordingly, in certain embodiments, post-neuromodulation level or activity for a target biomarker is determined during neuromodulation or relatively contemporaneous to neuromodulation, i.e., within 1 minute, 2 minutes, 5 minutes, 10 minutes, 15 minutes, or 30 minutes of neuromodulation. In preferred embodiments, post-neuromodulation level or activity for a target biomarker is determined in an acute timeframe, i.e., while the subject is still catheterized and/or under anesthesia. Alternatively or in addition to a change in level or activity at the time of neuromodulation or relatively contemporaneous to neuromodulation, a target biomarker may exhibit a change in level or activity at a later timepoint (e.g., at a chronic timepoint). For example, in certain embodiments a target biomarker exhibits a change in level or activity within 2 hours, 4 hours, 6 hours, 8 hours, 12 hours, 24 hours, 48 hours, 72 hours, 7 days, 14 days, one month, two months, four months, or one year of neuromodulation. Accordingly, in certain embodiments, post-neuromodulation level or activity for a target biomarker is determined 2 hours or more after neuromodulation, i.e., within 2 hours, 4 hours, 6 hours, 8 hours, 12 hours, 24 hours, 48 hours, 72 hours, 7 days, 14 days, one month, two months, four months, or one year of neuromodulation. In certain embodiments, changes in target biomarker level or activity at these later timepoints can be used to assess or classify a subject's response to neuromodulation. The resultant information can be used to develop predictive models for determining whether neuromodulation is likely to be effective in a particular subject or subpopulation.

The methods disclosed herein may be used to monitor the efficacy of neuromodulation carried out using a variety of suitable techniques. The neuromodulation, for example, may be electrically-induced, thermally-induced, chemically-induced, or induced in another suitable manner or combination of manners at one or more suitable treatment locations during a treatment procedure. For example, neuromodulation may be carried out by delivering monopolar or bipolar radio frequency (RF) energy, microwave energy, laser light or optical energy, magnetic, ultrasound energy (e.g., intravascularly delivered ultrasound, extracorporeal ultrasound, high frequency ultrasound (HIFU)), direct heat energy, and/or cryotherapeutic energy to target tissue at a treatment location to induce one or more desired effects at the treatment location. A treatment location may be a location proximate to one or more nerves being neuromodulated. In some embodiments, the treatment location is in or near a vessel or other body lumen. For example, a treatment location for renal neuromodulation may be at or near the renal artery. In certain embodiments, the identity of the target biomarkers may vary depending on the neuromodulation method being used. For example, neuromodulation using RF energy may result in changes in the level or activity of a different set of target biomarkers than cryotherapy. In other embodiments, a specific target biomarker or set of target biomarkers may be effective for monitoring efficacy across a range of neuromodulation techniques.

In certain embodiments, changes in target biomarker level or activity can be used in the prognosis of co-morbidities that are directly or indirectly benefited by neuromodulation. In other embodiments, changes in target biomarker level or activity can be used to predict a subject's response to neuromodulation.

Determination of baseline and/or post-neuromodulation target biomarker level or activity may be carried out using any previously known method and/or methods disclosed herein. In some embodiments, for example, determination of target biomarker level or activity utilizes a detection method that produces results in an acute timeframe following neuromodulation. Where a target biomarker is a secreted or cell surface biomolecule, determination of target biomarker level or activity may utilize one or more capture or detection agents. Where a target biomarker is an intracellular biomolecule, determination of target biomarker level or activity may utilize imaging/spectroscopy techniques that allow level or activity to be assessed in a non-invasive manner. In other embodiments, the level or activity of an intracellular target biomarker may require tissue sampling.

Figure 4:
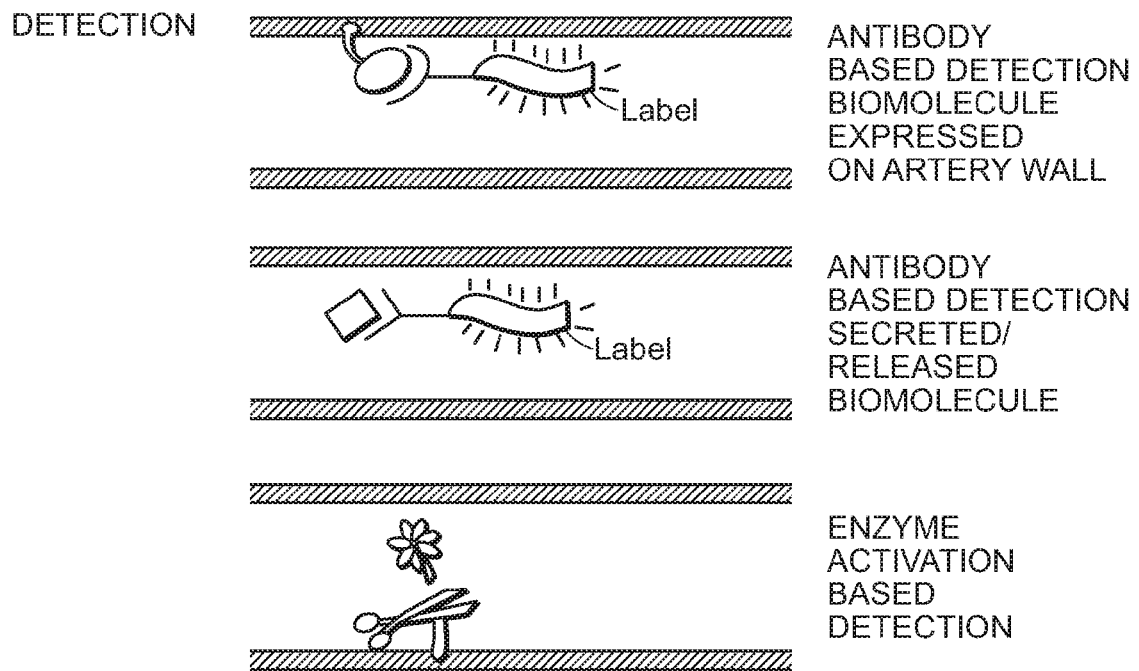
FIG. 4: Examples of target biomarker detection methods: antibody-based detection of artery wall proteins (upper panel), antibody-based detection of secreted proteins (middle panel), and activity-based detection of enzyme activity (lower panel).

In certain embodiments, determination of baseline or post-neuromodulation level of a target biomarker may be carried out using one or more capture agents that specifically bind the target biomarker, such as an antibody or an epitope-binding fragment thereof (see, e.g., FIG. 4; labeled antibody binding artery wall (upper panel) or secreted (lower panel) target biomarker), a ligand for the target biomarker, a receptor for which the target biomarker is a ligand, a nucleic acid complementary to an mRNA sequence encoding the target biomarker, or any other agent that specifically binds a target biomarker. In these embodiments, the target biomarker is detected based on binding to the capture agent.

Determination of baseline or post-neuromodulation activity of a target biomarker may be carried out using a detection agent that has a functional interaction with the target biomarker, such as a substrate for the target biomarker or an enzyme or catalytic antibody for which the target biomarker is a substrate (see, e.g., FIG. 4; scissors represent enzymatic detection agent capable of cleaving target biomarker). In these embodiments, target biomarker activity is detected based on presence of a specific function (e.g., substrate conversion). Alternatively, determination of target biomarker activity may be carried out using a capture agent specific for an enzymatic product or by-product of the target biomarker.

Capture or detection agents for use in determining the activity of a target biomarker may be in solution, or they may be immobilized on a surface such as a bead, resin, or one or more surfaces of a neuromodulation or other treatment device, a component thereof, or a separate capture device. Examples of suitable resins include, for example, hydrophobic resins, cation/anion exchange resins (e.g., carboxymethyl, sulfopropyl/diethylamine), immobilized metal affinity chromatography (IMAC) resins, and polar chromatographic resins (e.g., silica gel). In those embodiments that utilize a surface such as a bead or resin, all capture agents on the surface may be specific for a single target biomarker. Alternatively, capture or detection agents for multiple target biomarkers may be present on a single surface, allowing for simultaneous detection and analysis of multiple target biomarkers. In those embodiments wherein capture or detection agents are immobilized on one or more surfaces of a treatment device, a component thereof, or a separate capture device, the capture or detection agents may be on the outside of the device, i.e., in direct contact with arterial blood or the artery wall. In other embodiments, the capture or detection agents may be on an internal surface, such as the interior of a catheter or a capture compartment.

Figure 5:
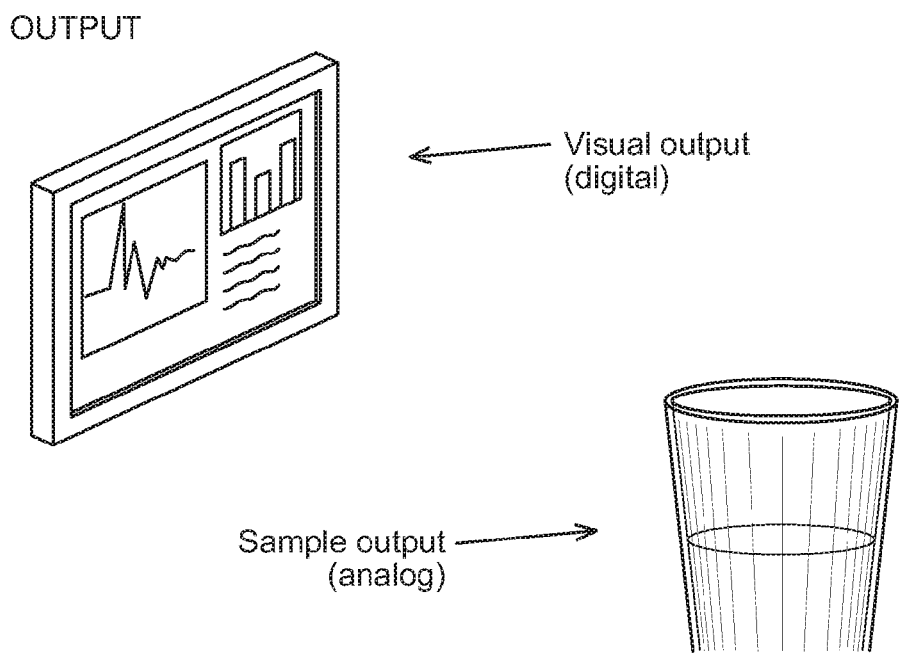
FIG. 5: Illustrative digital and analog outputs for displaying a detectable signal generated by the interaction of a target biomarker with a capture or detection agent.

In certain embodiments, binding of a target biomarker to a capture agent and/or interaction of the target biomarker with a detection agent results in a quantifiable signal. This quantifiable signal may be, for example, a colorimetric, fluorescent, heat, energy, or electric signal. In certain embodiments, this signal may be transduced to an external visual output device (see, e.g., FIG. 5). In certain embodiments, a capture or detection agent may be labeled, such as for example with an enzymatic or radioactive label. A capture or detection agent may be a binding substrate for a secondary capture agent, such as a labeled antibody.

Figure 6:
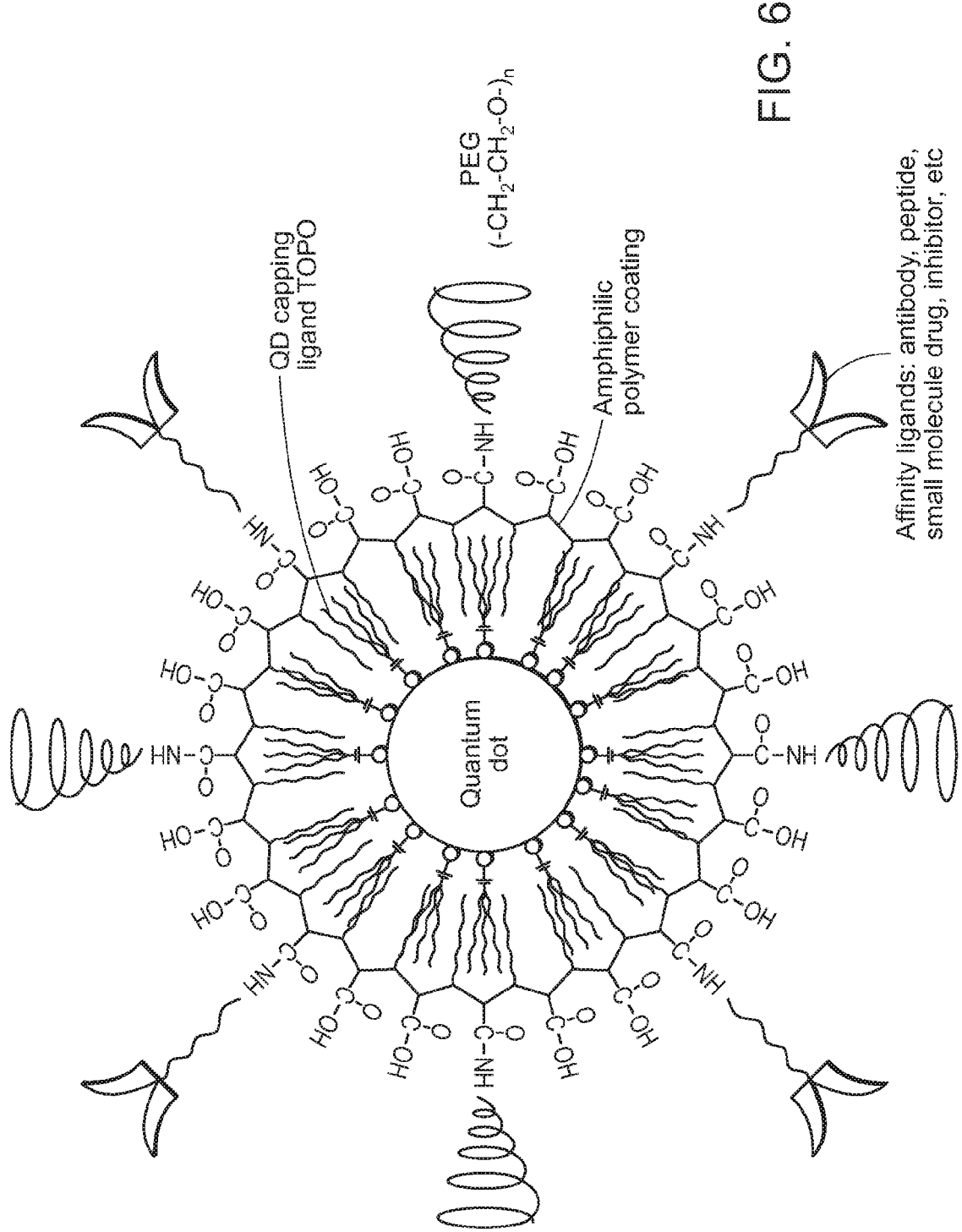
FIG. 6: Quantum dot system for generation of a detectable signal following binding of a target biomarker to an affinity ligand capture agent.

In certain embodiments, binding of a target biomarker to a capture agent results in a signal that which can be transduced to an external monitoring device. For example, binding of a target biomarker to a capture or detection agent may be detected using a high sensitivity fluorescence technique such as a resonance energy transfer method (e.g., Forster resonance energy transfer, bioluminescence resonance energy transfer, or surface plasmon resonance energy transfer). FIG. 6 illustrates a quantum dot embodiment for generating a signal based on binding of a target biomolecule to an affinity ligand capture agent (e.g., an antibody, peptide, small molecule drug, or inhibitor). Quantum dots are nanometer sized semiconductor crystals that fluoresce when excited with the proper frequency of light (see, e.g., Xing Nat Protoc 2:1152 (2007)). The emitted light is tuned by the size of the nanocrystal, and excitation frequencies range from near IR to UV. Dynamic visualization through skin has been demonstrated in animals using near IR radiation.

Figure 7:
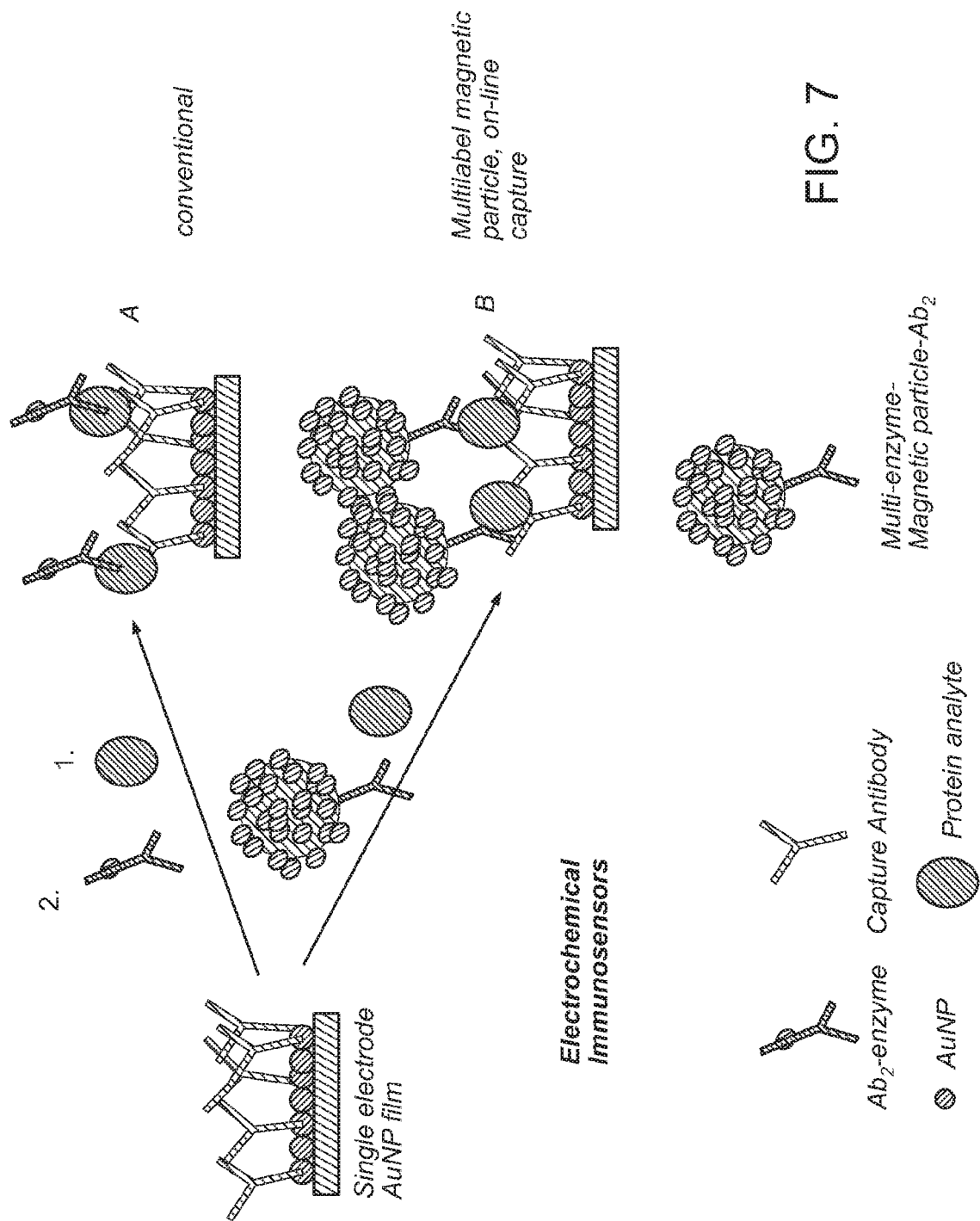
FIG. 7: Illustration of representative electrochemical immunosensor protocols.

In certain embodiments of the methods disclosed herein, determination of baseline and/or post-neuromodulation target biomarker level or activity is carried out using any immunoassay-based method. For example, target biomarker levels may be determined using an electrochemical immunosensor (see, e.g., FIG. 7), which provides concentration-dependent signaling (see, e.g., Centi Bioanalysis 1:1271 (2009); Rusling Analyst 135:2496 (2010)). Antibodies for use in an immunoassay-based determination of target biomarker level or activity may be labeled or unlabeled.

Determination of baseline and/or post-neuromodulation target biomarker level or activity may take place in vivo in some embodiments. For example, the determination may be carried out using the same device that is used to carry out neuromodulation or a component attached to the treatment device. Alternatively, determination of biomarker level or activity may be carried out using a separate device. In certain of these embodiments, the separate device can be delivered to the neuromodulation site via the same catheter used to deliver the treatment device. In other embodiments, however, determination of baseline and/or post-neuromodulation target biomarker level or activity takes place ex vivo.

In some embodiments, the interaction between a target biomarker and a capture or detection agent takes place at or near the neuromodulation site, e.g., near the renal artery. In certain of these embodiments, a target biomarker binds to a capture or detection agent in the bloodstream or at the surface of the arterial wall. In these embodiments, the capture or detection agent may be in solution (i.e., in the bloodstream) or immobilized to a surface that is in contact with the bloodstream and/or arterial wall. For example, a device or component thereof in which a capture or detection agent is integrated may be a balloon coated with one or more detection molecules that inflates to touch the ablated artery wall (see, e.g., FIG. 8, lower panel). Captured target biomarkers may be detected in vivo, or the balloon-based device may be removed for target biomarker detection ex vivo.

In other embodiments, however, the interaction between a target biomarker and a capture or detection agent can take place away from the neuromodulation site. For example, target biomarkers may be removed from a neuromodulation site and sequestered in a capture compartment (see, e.g., FIG. 8, upper panel). In those embodiments that utilize a capture compartment, the capture compartment may be located in vivo or ex vivo. In certain of these embodiments, the capture compartment may be located in vivo initially, then removed from the body for analysis (i.e., removed from the body prior to contact with capture or detection agents). In certain embodiments, a target biomarker may be contacted with capture or detection agents inside the capture compartment. In other embodiments, exposure to capture or detection agents may take place after a biological sample has been removed from the capture compartment. In certain embodiments, target biomarkers may be concentrated prior to or simultaneous with exposure to capture or detection agents. In those embodiments that utilize a capture compartment, concentration may be carried out within the capture compartment or after the biological sample has been removed from the capture compartment. In certain embodiments, concentration of target biomarkers may be carried out using one or more filters integrated into the capture device or capture compartment. For example, a first filter at the distal end of a capture compartment may be selected such that it allows passage of the target biomarker into the capture compartment while preventing passage of other biomolecules. A second filter at a proximal end of the capture component may be selected such it prevents passage of the target biomarker out of the capture compartment while allowing blood to flow out of the capture compartment. Through the use of one or more filters, a target biomarker may be concentrated within the capture compartment. Alternatively or in addition to the use of filters, one or more additional steps may be taken to concentrate target biomarkers in the capture compartment or after removal from the capture compartment. For example, target biomarkers may be concentrated using beads.

A representative embodiment of a target biomarker detection method and device is set forth in FIG. 9. In this embodiment, a blood sample containing secreted target biomarkers A and B is captured from near the ablation sites using a catheter based capture device (FIG. 9A), as will be described in more detail below. This capture step results in sequestration of the target biomarkers in a capture compartment wherein the biomarkers are concentrated. The target biomarkers bind to one or more immobilized capture agents on the inner surface of the capture compartment (FIG. 9B). Binding of the target biomarkers to the immobilized capture agents results in a signal that is transduced to an ex vivo device via an output generator (FIG. 9C). Examples of devices for carrying out these and other embodiments are described in more detail below with reference to FIGS. 51-56D.

Figure 10:
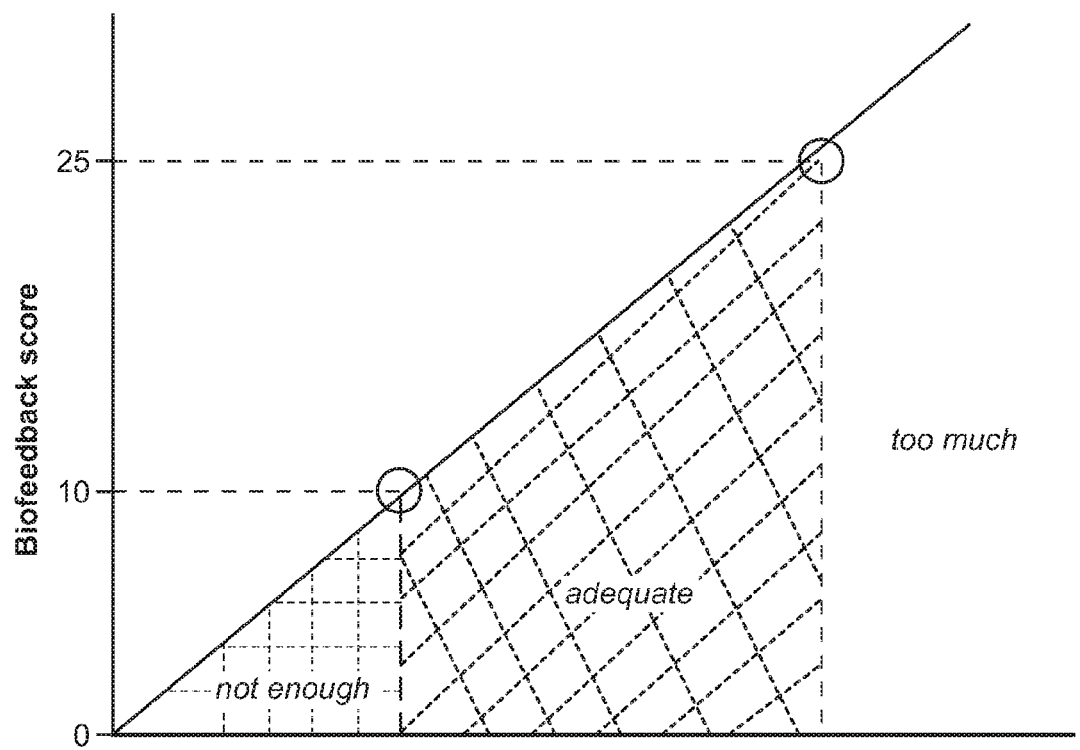
FIG. 10: Illustration of biofeedback score for determining the likelihood of success of a renal neuromodulation procedure.

In certain embodiments, the methods provided herein produce a biofeedback score indicating to a practitioner the likelihood that a neuromodulation procedure was successful. For example, a biofeedback score falling within a certain range indicates that the procedure was likely successful, while a score falling outside this range indicates that the procedure was unsuccessful (see, e.g., FIG. 10). In other embodiments, the methods provided herein provide a binary "yes or no" indicator of the success of a neuromodulation procedure. In these embodiments, a specific threshold increase or decrease in the level or activity of a target biomarker or set of target biomarkers indicates the neuromodulation procedure was successful. In certain of these embodiments, the specific threshold change indicates that the neuromodulation procedure was successful with a specific confidence interval (e.g., 95% or greater, 97% or greater, or 99% or greater). In some embodiments, information regarding changes in the level or activity of a target biomarker may be combined with one or more additional parameters such as temperature, nerve signaling data, or impedance in assessing neuromodulation efficacy. Further, efficacy may be evaluated based on a combination of all parameters, with changes in target biomarker level or activity simply functioning as one of the parameters.

For example, as disclosed in Example 1 below, a set of candidate protein target biomarkers was screened in vivo to identify proteins exhibiting a change in expression level in renal tissue at various timepoints following ablation. This resulted in the identification of a set of secreted, cell surface, and intracellular protein target biomarkers that showed increased or decreased expression levels at 10 minutes, 24 hours, and 7 days post-ablation.

Examples of secreted protein target biomarkers that were upregulated within 10 minutes of ablation include brain-derived neurotrophic factor (BDNF), calcitonin-related polypeptide beta (CALCB, CGRP), CD40L ligand (CD40L, CD40LG), clusterin (CLU), endothelin-3 (EDN3), interleukin 10 (IL-10), and kalakrein B1 (KLKB1). Examples of cell surface protein target biomarkers that were upregulated within 10 minutes of ablation include selectin E (SELE) and DnaJ (Hsp40) homolog superfamily A member 4 (DNAJA4). Examples of intracellular protein target biomarkers that were upregulated within 10 minutes of ablation include BTG2 family member 2 (BTG2), DNAJA4, DnaJ (Hsp40) homolog superfamily B member 1 (DNAJB1), FBJ murine osteosarcoma viral oncogene homolog (FOS), heat shock 27 kDa protein 1 (HSPB1), heat shock 60 kDa protein 1 (HSPD1), and heat shock 105 kDa/110 kDa protein 1 (HSPH1).

Examples of secreted protein target biomarkers that were upregulated within 24 hours of ablation include bone morphogenetic protein 7 (BMP7), IL-10, tumor necrosis factor receptor superfamily member 1B (TNFRSF1B), and leukemia inhibitor factor (LIF). Examples of cell surface protein target biomarkers that were upregulated within 24 hours of ablation include ATPase/Na/K transporting alpha 1 polypeptide (ATP1A1), endothelin receptor type B (ETB, EDNRB), integrin alpha M (ITGAM, CD11b), solute carrier family 2 (facilitated glucose/fructose transporter) member 5 (SLC2A5/GLUT5), SELE, Toll-like receptor 4 (TLR4), and TNFRSF1B. Examples of surface protein target biomarkers that were downregulated within 24 hours of ablation include melanocortin 2 receptor (MC2R). Examples of intracellular protein target biomarkers that were upregulated within 24 hours of ablation include heme oxygenase (decycling) 1 (HMOX-1), heat shock 70 kDa protein 5 (HSPA5), HSPD1, HSPH1, ATP1A1, and superoxide dismutase 2 (SOD2).

Examples of secreted protein target biomarkers that were upregulated within 7 days of ablation include natriuretic peptide B (BNP), CD40L, CLU, Fas ligand (FASLG), IL-10, TNFRSF1B, and LIF. Examples of secreted protein target biomarkers that were downregulated within 7 days of ablation include neurotrophin 3 (NTF3). Examples of cell surface protein target biomarkers that were upregulated within 7 days of ablation include ATP1A1, EDNRB, ITGAM, purinergic receptor P2Y G-protein coupled 12 (P2RY12), SELE, SLC2A5/GLUT5, Toll-like receptor 3 (TLR3), TLR4, Toll-like receptor 7 (TLR7), and TNFRSF1B. Examples of cell surface protein target biomarkers that were downregulated within 7 days of ablation include adrenergic alpha 2B receptor (ADRA2b). Examples of intracellular protein target biomarkers that were upregulated within 7 days of ablation include CDKN2B (p15), HMOX-1, heat shock 70 kDa protein 14 (HSPA14), ATP1A1, and HSPD1. Examples of intracellular protein target biomarkers that were downregulated within 7 days of ablation include CDKN1B (p27).

As disclosed in Example 2 below, a set of candidate protein target biomarkers was screened in vitro to identify proteins exhibiting a change in expression or secretion level at 1, 5, and 10 minutes after exposure to heat, inflammation, or a combination thereof. This resulted in the identification of a set of protein target biomarkers that showed increased expression or secretion levels at 1, 5, or 10 minutes post-ablation. Examples of protein target biomarkers that exhibited an increase in expression include caspase 10 (CASP10), CCL13 (MCP4), CCND1, CD70, alpha B crystalline (CRYAB), CPS1, DNAJB1, DNAJB11, heat shock 70 kDa protein 1A (HSPA1A), heat shock 70 kDa protein 1B (HSPA1B), heat shock protein B6 (HSPB6), IL-10, KIT, lymphotoxin alpha (LTA), myosin light chain kinase 3 (MYLK3), NODAL, NPY1R, POU1F1, and TCP-1-alpha (TCP1). Examples of protein target biomarkers that exhibited an increase in secretion include actin, cytoplasmic (ACTA2), S100 calcium binding protein A6 (CACY/2A9), cofilin-1 (CFL1), protein cTAGE-2 (CTAG1A1/CTAG21), L-lactate dehydrogenase (LDHA), transmembrane protein 141 (MGC141/TMEM141), N-alpha-acetyltransferase 20 (NAA20/NAT5), nucleoside diphosphate kinase B (NM23B), phytanoyl-CoA deoxygenase, peroxisomal (PAHX/PHYH1), prefoldin subunit 1 (PFDN1), serine/threonine protein kinase (PLK-2), tubulin alpha-1B-chain (TUBA1B), and vimentin (VIM).

As further disclosed in Example 2, a set of candidate protein target biomarkers was screened by treating a set of neuronal cells with heat, inflammation, or a combination thereof, then treating a set of endothelial cells with the neuronal cell secretome, i.e., conditioned media from the heat/inflammation treated neuronal cells. This conditioned media contains neuronal protein and non-protein stress factors that exhibit increased secretion after heat/inflammation treatment. Alternatively, the endothelial cells were treated directly with recombinant factors including neurotropic factor or angiogenic growth factors (e.g., BDNF, FGF5). Examples of protein target biomarkers that exhibited an increase in expression in the second set of cells include synuclein alpha (SNCA), BDNF, ciliary neurotrophic factor (CNTF), fibroblast growth factor 2 (basic) (FGF2), glial cell-derived factor 2 (basic) (GDNF), beta nerve growth factor 2 (NGF2), neurotrophin-3 (NTF3), PF4, EDN2, ACE2, interferon gamma (IFN-γ), artemin (ARTN), LIF, cerebellin 1 precursor (CBLN1), neuregulin 1 (NRG1), neuregulin 2 (NRG2), neuregulin 4 (NRG4), persephin (PSPN), NTF4, and transforming growth factor alpha (TGFA).

As disclosed in Example 3 below, an additional set of protein and non-protein candidate target biomarkers will be screened in vivo to identify potential target biomarkers exhibiting a change in renal arterial or venous blood levels at various timepoints following ablation. As set forth in Example 3, an initial evaluation using this screen was carried out using NE and CFL1. Additional candidate target biomarkers that may be evaluated in this screen include NPY, DBN, $Ca^{2+}$, renin, dopamine beta-hydroxylase (DBH), angiotensin (AGT), endothelin 1, 2, and 3, neurotensin (NTS), and amyloid beta (A4) precursor protein (APP).

In certain embodiments, the methods disclosed herein utilize one or more of the target biomarkers listed above from the in vivo and in vitro studies to evaluate the efficacy of renal neuromodulation. Provided herein in certain embodiments are compositions comprising capture or detection agents specific to one or more of these target biomarkers, as well as kits, panels, and arrays comprising such capture or detection agents.

The following examples are provided to better illustrate the disclosed technology and are not to be interpreted as limiting the scope of the technology. To the extent that specific materials are mentioned, it is merely for purposes of illustration and is not intended to limit the technology. It will be understood that many variations can be made in the procedures herein described while still remaining within the bounds of the present technology. It is the intention of the inventors that such variations are included within the scope of the technology.

EXAMPLES

Example 1

In Vivo Target Biomarker Screening (Porcine Renal Tissue)

Gene expression studies were conducted in renal artery tissue samples from domestic swine to identify candidate target biomarkers that exhibit a change in expression level at various time points after renal denervation/ablation.

Animals were broken into three groups of three animals each: naïve (no treatment), sham (catheterized but not ablated), and treated (subject to ablation at 65° C. and 90 seconds using a spiral ablation catheter device). Left and right renal arteries and surrounding tissue samples were obtained by sampling tissue in the area of ablation at 10 minutes ("day 0"), 7 days, or 24 hours post-treatment. Slices from the center of ablation sites were removed for histopathological analysis, and the ablation sites were cleaned up by removing any non-ablated tissue and pooled. Tissue was maintained during the dissection process using RNALater.

Pooled tissue samples were weighed and mixed under frozen conditions, and then added to round-bottomed tubes containing 2× stainless steel beads (5 mm diameter) at room temperature. 900 µL QIAzol lysis reagent was added to each tube, and the tissue was macerated using the TissueLyser II Adaptor Set with disruption at 30 Hz (3×2 minutes) to release RNA. An additional 300 µL of lysis buffer was added to each tube, and the disruption cycle was repeated (1×2 minutes at 30 Hz). Lysates were transferred to new Eppendorf tubes for mRNA isolation.

120 µl gDNA Eliminator Solution was added to each lysate sample, and tubes were shaken vigorously for 15 seconds. 180 µl of chloroform was added, and tubes were again shaken vigorously for 15 seconds. After 2-3 minutes at room temperature, tubes containing homogenate were centrifuged at 12,000×g for 15 minutes at 4° C. The centrifuge was warmed to room temperature, and the upper aqueous phase was transferred to a new Eppendorf tube. An equal volume of 70% ethanol was added to each tube with thorough mixing, and 700 µl of each sample was transferred to an RNeasy Mini spin column in a 2 mL collection tube. Samples were centrifuged for 15 seconds at >8000×g (>10,000 rpm) at room temperature and flow-thru was discarded. The ethanol mixing and RNeasy centrifugation steps were repeated until all sample was used up. 700 µL of Buffer RWT was added to each spin column, followed by centrifugation for 15 seconds at >8,000×g (>10,000 rpm) to wash the membrane. Flow-thru was discarded, and 500 µl Buffer RPE was added each spin column, followed by centrifugation for 15 seconds at >8,000×g (>10,000 rpm). Flow thru was discarded, and 500 µl Buffer RPE was again added to each spin column, followed by centrifugation for 2 minutes at >8,000×g (>10,000 rpm) to wash the membrane. RNeasy spin columns were placed in a new 2 mL collection tube and centrifuged at full speed for 1 minute. The spin column was placed in a new 1.5 mL collection tube, 50 µL RNase free water was added directly to the spin column membrane, and RNA eluted was eluted by centrifugation for 1 minute at >8,000×g (>10,000 rpm). This step was repeated using another 50 µL of RNase free water. To ensure significance, A260 readings were verified to be greater than 0.15. An absorbance of 1 unit at 260 nm corresponds to 44 µg of mRNA per mL (A260=1=µg/mL) at neutral pH.

ABI High Capacity cDNA kits were used to convert mRNA to cDNA for quantitative real-time PCR (qPCR). PCR was performed in optical 384-well plates, freshly prepared on the Eppendorf epMotion liquid handler. Final reaction volume was 20 µL (4 µL Taqman Assay+mixture of 6 µL cDNA (3 ng)+10 µL Universal Master Mix with UNG). Assays were performed to include +RT (reverse transcriptase) samples and, when appropriate, a −RT control. Endogenous controls (×2) were run in triplicate and animal samples were run only once for screening purposes. The real-time PCR protocol included an initial step of 50° C. (2 minutes) to activate the DNA polymerase, denaturation by a hot start at 95° C. for 10 minutes, and 40 cycles of a two-step program (denaturation at 95° C. for 15 seconds for primer annealing/extension at 60° C. for 1 minute). Fluorescence data was collected at 60° C. Fluorescence was quantified with the ABI PRISM 7900HT, and the resultant data was analyzed using SDS RQ Manager (1.2.1) Software (Sequence Detection System Software, Applied Biosystems). Each candidate target biomarker was checked, and threshold and baseline was adjusted to produce (in ΔRn versus Cycle) an amplification curve of the type suggested by Applied Biosystems in their "Relative Quantification Using Comparative Ct Getting Started Guide." A calibrator was selected for calculation of the RQ (relative quantification). The calibrator was based on an average of 6× figures from the three naïve animals, left & right arteries, resulting in a numerical result of 1 for the naïve RQ. For calculation of the RQ for the standard deviation (SD) of the naïves, any other experimental animal was used as a calibrator (generally the first animal for Day 0 treated). RQ averages of animals (×3) in the same treatment group were calculated for each point and for each candidate target biomarker individually, and plotted in bar graphs.

Figure 11:
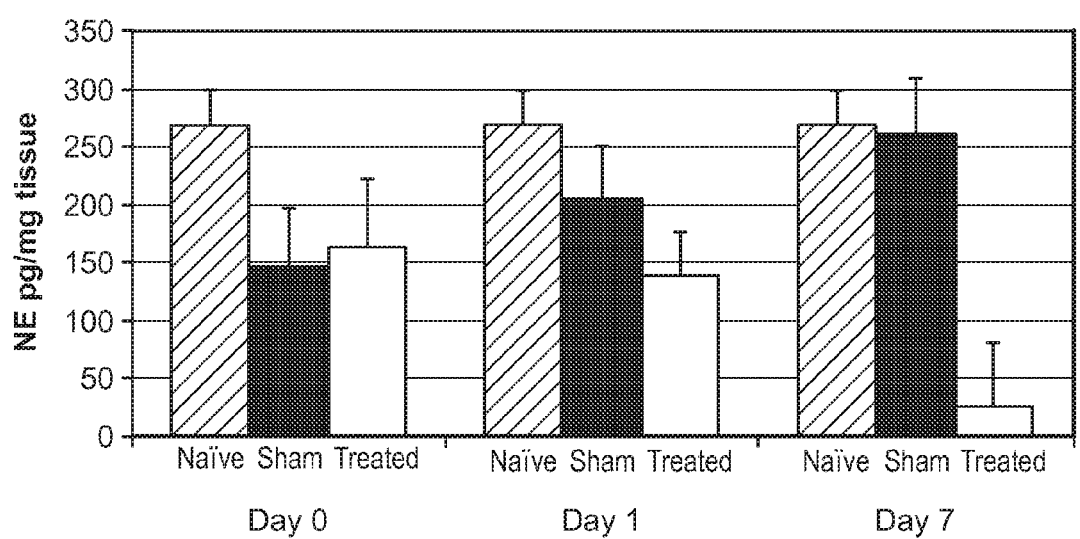
FIG. 11: Average kidney NE levels post-ablation.

Renal NE and dopamine (DBN) levels in naïve, sham, and test animals were evaluated at 10 minutes, 24 hours, and 7 days. Average kidney NE production post-ablation is shown in FIG. 11. Candidate genes were evaluated for their ability to provide a graded response that correlates with NE production.

The initial screen was carried out using the 70 candidate target biomarkers set forth in Table 1. Shaded genes exhibited an increase or decrease in expression within 10 minutes, 24 hours, and/or 7 days of ablation. Preferred target biomarkers are those exhibiting at least a two-fold change in expression within 10 minutes of ablation. From the initial screen, this group included the genes BDNF, CALCB, CD40L, CLU, EDN3, IL-10, KLKB1, SELE, DNAJA4, BTG2, DNAJB1, FOS, HSPB1, HSPD1, and HSPH1. Of these, the most preferred biomarkers are the secreted proteins BDNF, CALCB, CD40L, CLU, EDN3, IL-10, and KLKB1. Additional screens may be carried out to evaluate candidate target biomarker expression at later time periods (e.g., 1 month, 6 months, or one year post-ablation) in order to validate efficacy as long-term target biomarkers and durability of changes in expression.

TABLE 1

Figure 12:
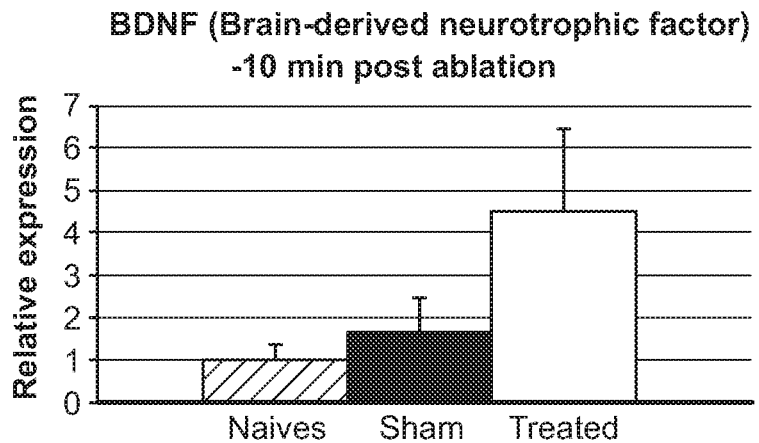
FIG. 12: Upregulation of BDNF 10 minutes post-ablation in endothelial cells.
Figure 13:
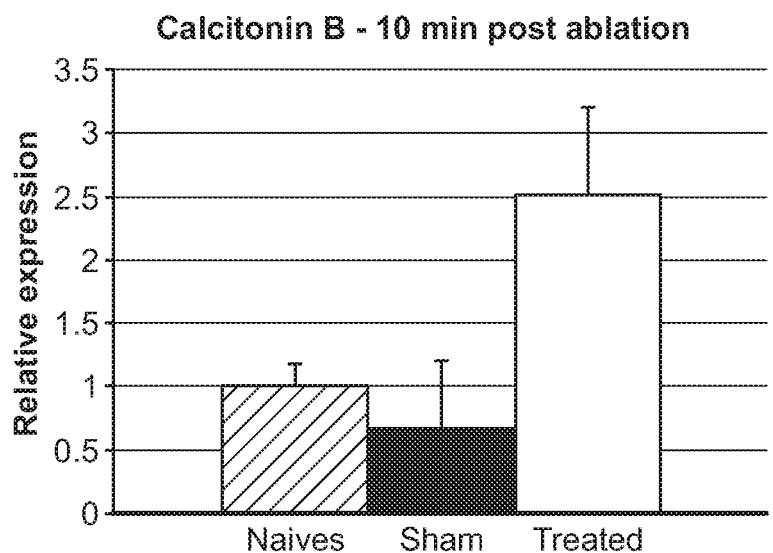
FIG. 13: Upregulation of CALCB 10 minutes post-ablation in endothelial cells.
Figure 14:
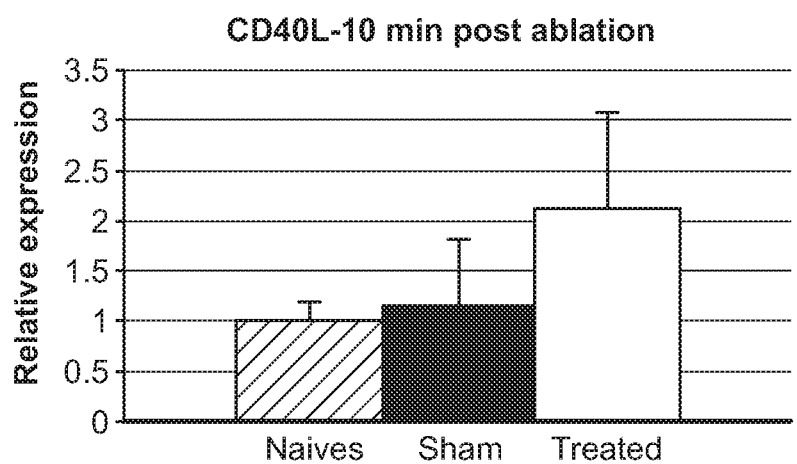
FIG. 14: Upregulation of CD40L 10 minutes post-ablation in endothelial cells.
Figure 15:
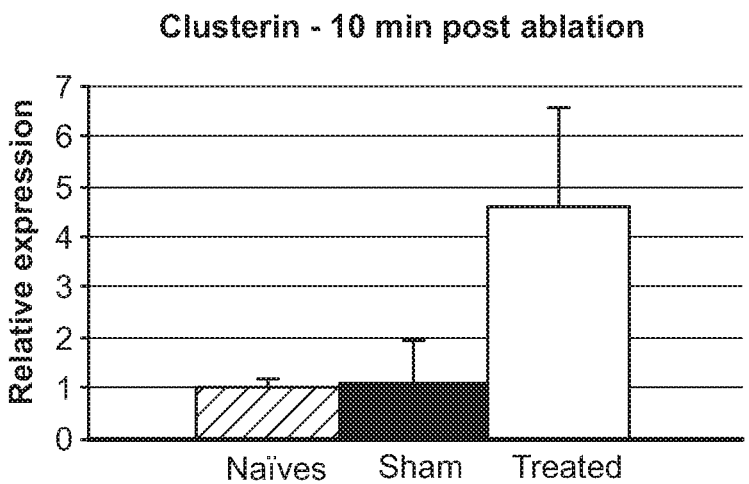
FIG. 15: Upregulation of CLU 10 minutes post-ablation in endothelial cells.
Figure 16:
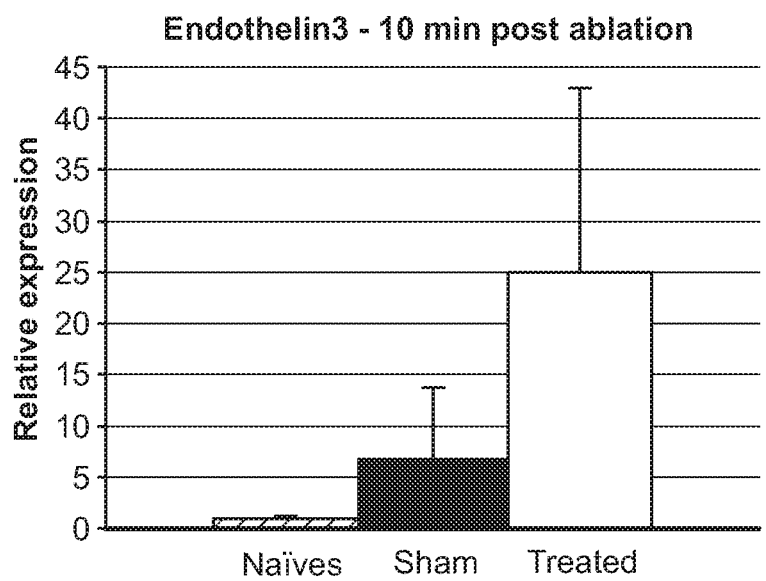
FIG. 16: Upregulation of EDN310 minutes post-ablation in endothelial cells.
Figure 17:
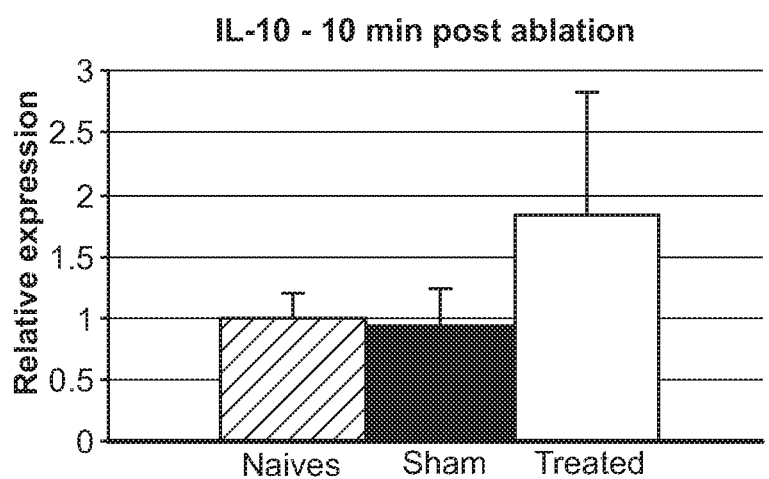
FIG. 17: Upregulation of IL-10 10 minutes post-ablation in endothelial cells.
Figure 18:
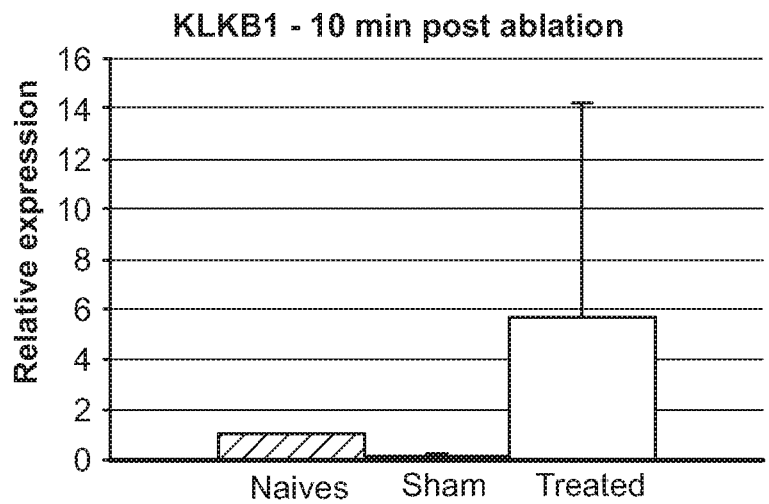
FIG. 18: Upregulation of KLKB1 10 minutes post-ablation in endothelial cells.

| Gene (Reference) | Location | Result | Gene Product Function/Description |
|---|---|---|---|
| BDNF (Frostick Microsurgery 18: 397 (1998); Heberlein Psychopharmacology (Berl) 209: 213 (2010)) | Secreted | Upregulated 10 minutes post-ablation (FIG. 12) | Promotes survival and differentiation of selected neuronal populations of the peripheral and central nervous system, participates in axonal growth and pathfinding and in modulation of dendritic growth and morphology |
| CALCB (Xie Hypertension 54: 1298 (2009); Xie J Pharmacol Exp Ther 325: 751 (2008)) | Secreted | Upregulated 10 minutes post-ablation (FIG. 13) | Potent vasodilator and hypotensor, potential neurotransmitter or neuromodulator role |
| CD40L (Jin Anticancer Drugs 23: 445 (2012)) | Secreted | Upregulated 10 minutes post-ablation (FIG. 14) Upregulated 7 days post-ablation | Pro-inflammatory and immunoregulatory functions |
| CLU (Lu Curr Med Chem 17: 957 (2010)) | Secreted | Upregulated 10 minutes post-ablation (FIG. 15) Upregulated 7 days post-ablation | Secreted chaperone (heatshock protein) |
| EDN3 (Paulis Nat Rev Cardiol 7: 431 (2010)) | Secreted | Upregulated 10 minutes post-ablation (FIG. 16) | Potent vasoconstrictive peptide |
| IL-10 (Zager Am J Physiol Renal Physiol 301: F1334 (2011); Lu Curr Med Chem 17: 957 (2010)) | Secreted | Upregulated 10 minutes post-ablation (FIG. 17) Upregulated 24 hours post-ablation Upregulated 7 days post-ablation | Anti-inflammatory cytokine with pleiotropic effects in immunoregulation and inflammation, inhibits synthesis of various cytokines including IFN-γ, IL-2, IL-3, TNF, and GM-CSF produced by activated macrophages and helper T-cells |
| KLKB1 (Paulis Nat Rev Cardiol 7: 431 (2010)) | Secreted | Upregulated 10 minutes post-ablation (FIG. 18) | Participates in surface-dependent activation coagulation, fibrinolysis, and inflammation, may play a role in the renin-angiotensin system by converting prorenin to renin (vasoconstriction) |
| SELE (Sonna J Appl Physiol 92: 1725 (2002)) | Surface | Upregulated 10 minutes post-ablation Upregulated 24 hours post-ablation Upregulated 7 days post-ablation | Endothelial cell adhesion molecular/inflammation |
| DNAJA4 (Sonna J Appl Physiol 92: 1725 (2002)) | Intracellular/ Surface | Upregulated 10 minutes post-ablation | Protein folding and heat response |
| BTG2 (Struckmann Cancer Res 64: 1632 (2004)) | Intracellular | Upregulated 10 minutes post-ablation | Anti-proliferative, regulator of neuron differentiation, transcriptional co-factor |
| DNAJB1 (Lu Curr Med Chem 17: 957 (2010)) | Intracellular | Upregulated 10 minutes post-ablation | Interacts with Hsp70, stimulates ATPase activity |

TABLE 1-continued

Figure 19:
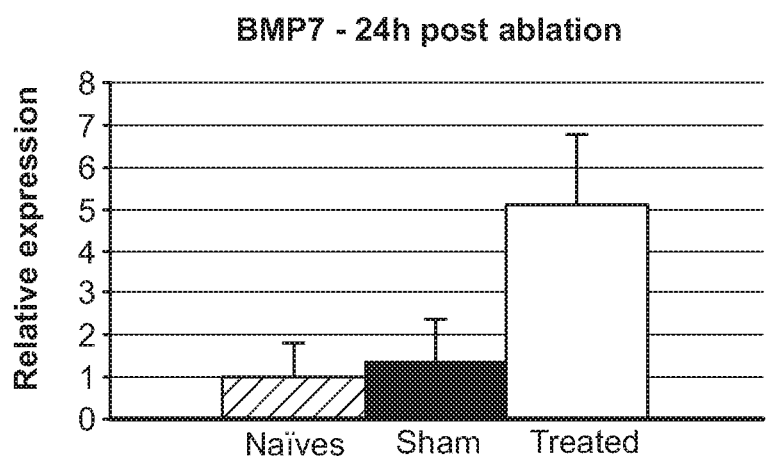
FIG. 19: Upregulation of BMP7 24 hours post-ablation in endothelial cells.
Figure 20:
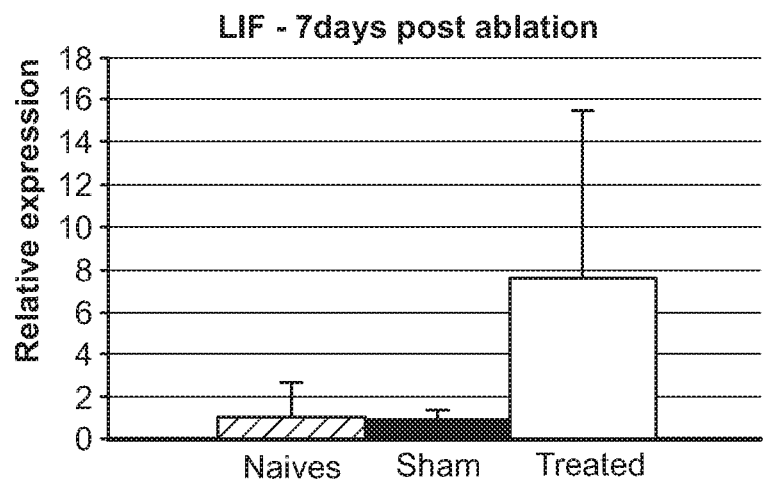
FIG. 20: Upregulation of LIF 7 days post-ablation in endothelial cells.
Figure 21:
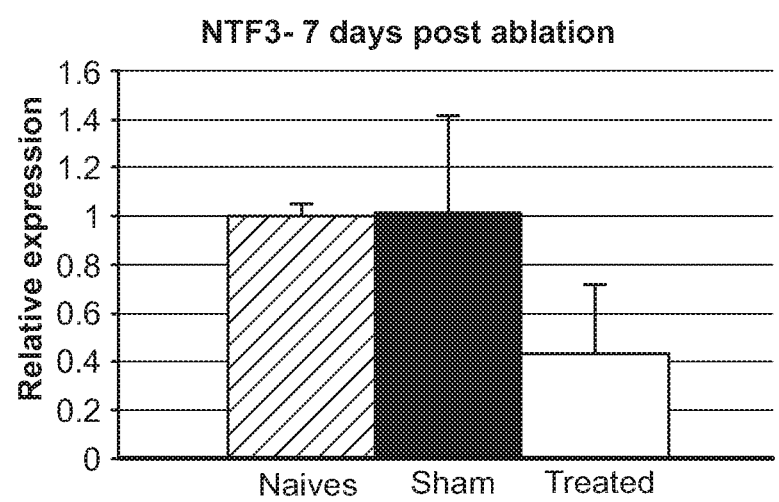
FIG. 21: Downregulation of NTF3 7 days post-ablation in endothelial cells.

| Gene (Reference) | Location | Result | Gene Product Function/Description |
|---|---|---|---|
| FOS (Sonna J Appl Physiol 92: 1725 (2002)) | Intracellular | Upregulated 10 minutes post-ablation | Apoptosis, regulation of cell proliferation, differentiation, and transformation |
| HSPB1 (Lu Curr Med Chem 17: 957 (2010)) | Intracellular | Upregulated 10 minutes post-ablation | Stress resistance, actin organization |
| HSPD1 (Lu Curr Med Chem 17: 957 (2010)) | Intracellular | Upregulated 10 minutes post-ablation Upregulated 24 hours post-ablation Upregulated 7 days post-ablation | Chaperonin, involved in folding of mitochondrial matrix proteins |
| HSPH1 (Lu Curr Med Chem 17: 957 (2010)) | Intracellular | Upregulated 10 minutes post-ablation Upregulated 24 hours post-ablation | Prevents aggregation of denatured proteins under severe stress |
| BMP7 (Zeisberg Nephrol Dial Transplant 21: 568 (2006)) | Secreted | Upregulated 24 hours post-ablation (FIG. 19) | Member of TGFβ superfamily |
| LIF (Yoshino J Am Soc Nephrol 14: 3090 (2003)) | Secreted | Upregulated 24 hours post-ablation Upregulated 7 days post-ablation (FIG. 20) | Pleiotropic cytokine involved in nephrogenesis and ECM repair |
| ATP1A1 (Liu Mol Biol Rep 38: 83 (2011)) | Intracellular/ Surface | Upregulated 24 hours post-ablation Upregulated 7 days post-ablation | Establishes and maintains electrochemical gradients of $Na^+$ and $K^+$ across plasma membrane |
| EDNRB (Paulis Nat Rev Cardiol 7: 431 (2010)) | Surface | Upregulated 24 hours post-ablation Upregulated 7 days post-ablation | Involved in vasoconstriction, vasodilation, and cell proliferation |
| ITGAM (Pereira Hemodial Int 14: 295 (2010)) | Surface | Upregulated 24 hours post-ablation Upregulated 7 days post-ablation | Mediates inflammation and adhesion |
| MC2R (Paulis Nat Rev Cardiol 7: 431 (2010)) | Surface | Downregulated 24 hours post-ablation | Involved in energy homeostasis, inflammation, immunomodulation, and temperature control |
| SLC2A5/GLUT5 (Soleimani Acta Physiol (Oxf) 201: 55 (2011) | Surface | Upregulated 24 hours post-ablation Upregulated 7 days post-ablation | Fructose transporter |
| TLR4 (Lu Curr Med Chem 17: 957 (2010)) | Surface | Upregulated 24 hours post-ablation Upregulated 7 days post-ablation | Pattern recognition receptor, involved in inflammation |
| TNFRSF1B (Mas Transplantation 85: 626 (2008)) | Secreted/ Surface | Upregulated 24 hours post-ablation Upregulated 7 days post-ablation | Involved in recruitment of anti-apoptotic proteins |
| HMOX1 (Sonna J Appl Physiol 92: 1725 (2002)) | Intracellular | Upregulated 24 hours post-ablation Upregulated 7 days post-ablation | Catalyzes degradation of heme, active during physiological stress |
| HSPA5 (SABiosciences $RT_2$ Profiler PCR Array Human Neurotoxicity platform) | Intracellular | Upregulated 24 hours post-ablation | Facilitates assembly of multimeric protein complexes in ER |
| SOD2 (SABiosciences $RT_2$ Profiler PCR Array Human Neurotoxicity platform) | Intracellular | Upregulated 24 hours post-ablation | Destroys superoxide anion radicals |
| BNP (Paulis Nat Rev Cardiol 7: 431 (2010)) | Secreted | Upregulated 7 days post-ablation | Involved in natriuresis, diuresis, vasorelaxation, renin inhibition, and aldosterone secretion |
| FASLG (SABiosciences $RT_2$ Profiler PCR Array Human Neurotoxicity platform) | Secreted | Upregulated 7 days post-ablation | Triggers apoptosis |
| NTF3 (Frostick Microsurgery 18: 397 (1998)) | Secreted | Downregulated 7 days post-ablation (FIG. 21) | Neurotrophic growth factor, controls neuron survival and differentiation |
| ADRA2B (Kopp Hypertension 57: 640 (2011)) | Surface | Downregulated 7 days post-ablation | Involved in regulation of neurotransmitter release from sympathetic nerves and adrenergic neurons in the CNS |

TABLE 1-continued

| Gene (Reference) | Location | Result | Gene Product Function/Description |
|---|---|---|---|
| P2RY12 (Lechner Purinergic Signal 1: 31 (2004)) | Surface | Upregulated 7 days post-ablation | Diverse physiological roles including platelet aggregation, muscle contraction, and neurotransmission |
| TLR3 (Musial Pediatr Nephrol 26: 1031 (2011)) | Surface | Upregulated 7 days post-ablation | Activation of innate immunity and inflammation |
| TLR7 (Musial Pediatr Nephrol 26: 1031 (2011)) | Surface | Upregulated 7 days post-ablation | Activation of innate immunity and inflammation |
| Cyclin-dependent kinase inhibitor 2B (CDKN2B, p15) (Romanenko Diagn Mol Pathol 11: 163 (2002)) | Intracellular | Upregulated 7 days post-ablation | Potent inhibitor of cell cycle G1 progression, potent effector of TGFβ-induced cell cycle arrest |
| Cyclin-dependent kinase inhibitor 1B (CDKN1B, p27, Kip1) (Andres Cardiovasc Res 63: 11 (2004)) | Intracellular | Downregulated 7 days post-ablation | |
| Heat shock 70 kDa protein 14 (HSPA14) | Intracellular | Upregulated 7 days post-ablation | |
| Angiotensin 1 converting enzyme (ACE) (Frostick Microsurgery 18: 397 (1998); Paulis Nat Rev Cardiol 7: 431 (2010)) | Surface | | |
| Actin alpha 2 (ACTA2) (Yuan Am J Physiol Regul Integr Comp Physiol 284: R1219 (2003)) | Intracellular | | |
| Activin A receptor type IIB (ACVR2B) (Pache Am J Physiol Renal Physiol 291: F654 (2006)) | Surface | | |
| Angiotensin II receptor type 2 (AGTR2) (Paulis Nat Rev Cardiol 7: 431 (2010)) | Surface | | |
| Agouti signaling protein (ASIP) (Sonna J Appl Physiol 92: 1725 (2002)) | Secreted | | |
| Arginine vasopressin (AVP) (Paulis Nat Rev Cardiol 7: 431 (2010)) | Secreted | | |
| Arginine vasopressin receptor 2 (AVPR2) (Paulis Nat Rev Cardiol 7: 431 (2010)) | Surface | | |
| Bradykinin receptor B2 (BDKRB2) (Paulis Nat Rev Cardiol 7: 431 (2010)) | Surface | | |
| Caspase 3 apoptosis-related cysteine peptidase (CASP3) (Singdha Neurosci Bull 28: 14 (2012)) | Intracellular | | |
| Chloride intracellular channel 1 (CLIC1) (SABiosciences $RT_2$ Profiler PCR Array Human Hypertension platform) | Surface/intracellular | | |
| Cytochrome P450 family 2 subfamily E polypeptide 1 (CYP2E1) (Wang Exp Toxicol Pathol 61: 169 (2009)) | Surface | | |
| DnaJ/Hsp40 homolog subfamily C member 3 (DNAJC3) (Sonna J Appl Physiol 92: 1725 (2002)) | Intracellular | | |
| Endothelin converting enzyme 1 (ECE1) (Ihling Curr Vasc Pharmacol 2: 249 (2004)) | Surface | | |
| Endothelin 1 (EDN1) (Paulis Nat Rev Cardiol 7: 431 (2010)) | Secreted | | |
| Endothelin receptor type A (EDNRA) (Paulis Nat Rev Cardiol 7: 431 (2010)) | Surface | | |
| Guanylate cyclase 1 soluble alpha 3 (GUCY1A3) (SABiosciences $RT_2$ Profiler PCR Array Human Hypertension platform) | Intracellular | | |
| Heat shock 70 kDa protein 6 (HSP70B) (HSPA6) (Sonna J Appl Physiol 92: 1725 (2002)) | Intracellular | | |

TABLE 1-continued

| Gene (Reference) | Location | Result | Gene Product Function/Description |
|---|---|---|---|
| Interferon (alpha, beta, and omega) receptor 1 (IFNAR1) (Bhattacharya J Biol Chem 286: 22069 (2011)) | Surface | | |
| Integrin alpha V vitronectin receptor (ITGAV) (SABiosciences RT$_2$ Profiler PCR Array Human Endothelial Cell Biology platform) | Surface | | |
| Potassium large conductance calcium-activated channel subfamily M alpha member 1 (KCNMA1) (SABiosciences RT$_2$ Profiler PCR Array Human Hypertension platform) | Surface | | |
| Kruppel-like factor 4 (KLF4) (Liu Cell Stress Chaperones 11: 379 (2006)) | Intracellular | | |
| Kininogen 1 (KNG1) (Paulis Nat Rev Cardiol 7: 431 (2010)) | Secreted | | |
| Neuropeptide Y (NPY) (Krukoff Mol Brain Res 19: 287 (1993)) | Secreted | | |
| Phenylethanolamine-N-methyltransferase noradrenalin (PNMT) (Wong Ann NY Acad Sci 1148: 249 (2008)) | Intracellular | | |
| Paraoxanase 2 (PON2) (Horke Circulation 115: 2055 (2007)) | Surface | | |
| Prostaglandin D2 Synthase 21 kDa (brain) (PTGDS) (Vivekanandan-Giri Int J Proteomics 2011: 214715 (2011)) | Intracellular/ secreted | | |
| Solute carrier family 22 organic cation transporter 1-OCT1 (SLC22A1) (Zhao Cancer Res 60: 6276 (2000)) | Surface | | |
| SRA stem-loop interacting RNA binding protein (SLIRP) (Lu Curr Med Chem 17: 957 (2010)) | Intracellular | | |
| Superoxide dismutase 1, soluble (SOD1) (Sonna J Appl Physiol 92: 1725 (2002)) | Intracellular | | |
| Thrombomodulin (THBD) (SABiosciences RT$_2$ Profiler PCR Array Human Endothelial Cell Biology platform) | Surface | | |
| Transient receptor potential cation channel subfamily V member 1 (TRPV1) (Xie Hypertension 54: 1298 (2009)) | Surface | | |
| Vascular cell adhesion molecule 1 (VCAM1) (SABiosciences RT$_2$ Profiler PCR Array Human Endothelial Cell Biology platform) | Surface | | |
| Von Willebrand factor (vWF) (SABiosciences RT$_2$ Profiler PCR Array Human Endothelial Cell Biology platform) | Secreted | | |

Additional screens will be carried out using genes associated with nerves in the renal pelvis, wherein a high percentage are afferent. Examples of such genes are set forth in Table 2.

TABLE 2

| Gene (Reference) | Location |
|---|---|
| Gamma 2 actin (ACTG2) (Higgins Mol Cell Biol 15: 649 (2004)) | Intracellular |
| Caveolin 1 (Cav1) (Higgins Mol Cell Biol 15: 649 (2004)) | Surface |
| Calponin 1 (CNN1) (Higgins Mol Cell Biol 15: 649 (2004)) | Intracellular |
| Actin binding protein 280 (FLNA) (Higgins Mol Cell Biol 15: 649 (2004)) | Intracellular |

TABLE 2-continued

| Gene (Reference) | Location |
|---|---|
| Glutathione peroxidase 2 (GPX2) (Higgins Mol Cell Biol 15: 649 (2004)) | Intracellular |
| Myosin light polypeptide kinase (MYLK) (Higgins Mol Cell Biol 15: 649 (2004)) | |
| c-AMP protein kinase A (PRKACA) (Kopp Contrib Nephrol 172: 107 (2011)) | Intracellular |
| Prostate stem cell antigen (PSCA) (Higgins Mol Cell Biol 15: 649 (2004)) | Surface |
| Prostaglandin $E_2$ (PTGER2) (Kopp Contrib Nephrol 172: 107 (2011)) | Surface |
| EP4 receptor (PTGER4) (Kopp Contrib Nephrol 172: 107 (2011)) | Surface |
| Cyclooxygenase 2 (COX-2) (PTGS2) (Kopp Contrib Nephrol 172: 107 (2011)) | Surface |
| Tachykinin 1 precursor (TAC1) (Kopp Contrib Nephrol 172: 107 (2011)) | Secreted |
| Tachykinin receptor 1 (TACR1-NK1) (Xie Hypertension 54: 1298 (2009)) | Surface |
| TP63 (Higgins Mol Cell Biol 15: 649 (2004)) | Intracellular |
| Tropomyosin 2 (TPM2) (Higgins Mol Cell Biol 15: 649 (2004)) | |
| Uroplakin 1B (Upk1B) (Higgins Mol Cell Biol 15: 649 (2004)) | Surface |
| Upk3A (Higgins Mol Cell Biol 15: 649 (2004)) | Surface |

Screens will also be carried out using various neuronal genes that are not necessarily associated with kidney afferent nerves. Examples of such genes are set forth in Table 3.

TABLE 3

| Gene (Reference) | Location |
|---|---|
| Annexin V (ANXA5) (Luo Nat Med 5: 17 (1999)) | Intracellular |
| Calcitonin gene-related polypeptide alpha (CGRP/CALCA) (Luo Nat Med 5: 17 (1999)) | Secreted |
| Fatty acid binding protein, brain (FABP7) (Luo Nat Med 5: 17 (1999)) | Intracellular |
| Neurofilament, heavy polypeptide (NEFH) (Luo Nat Med 5: 17 (1999)) | Intracellular |
| Neurofilament, heavy polypeptide (NEFL) (Luo Nat Med 5: 17 (1999)) | Intracellular |
| Phospholipase C delta 4 (PLCD4) (Luo Nat Med 5: 17 (1999))) | Surface/ intracellular |
| Na N sodium voltage-gated channel (SCN11A) (Luo Nat Med 5: 17 (1999)) | Surface |
| Beta 1 subunit of voltage gated Na channels (SCN1B) (Luo Nat Med 5: 17 (1999)) | Surface |

Additional screens will be carried out using a variety of secreted, surface, and intracellular genes. Examples of genes that may be included in such screens include those set forth in Table 4.

TABLE 4

| Gene (Reference) | Location |
|---|---|
| Actinin alpha 4 (ACTN4) (Higgins Mol Biol Cell 15: 649 (2004)) | Intracellular |
| Activin A receptor type IIA (ACVR2A) (Maeshima Endocr J 55: 1 (2008)) | Surface |
| Aldolase B fructose-biphosphate (ALDOB) (Higgins Mol Biol Cell 15: 649 (2004)) | Intracellular |
| Biglycan (BGN) (Wu J Clin Invest 117: 2847 (2007)) | Secreted |
| Complement 5 (C5) (Kerr Immunobiol 217: 195 (2012)) | Secreted |

TABLE 4-continued

| Gene (Reference) | Location |
|---|---|
| MCP-1 (CCL2) (Darisipudi Am J Pathol 179: 116 (2011)) | Secreted |
| Chemokine (C-C motif) ligand 5 (CCL5) (Lo Transplantation 91: 70 (2011)) | Secreted |
| Chemokine (C-C motif) receptor 1 (CCR1) (Dikow Transplantation 90: 771 (2010)) | Surface |
| Ciliary neurotrophic factor (CNTF) (Ransom Kidney Int 67: 1275 (2005)) | Intracellular |
| Collagen type 1 alpha 1 (Col1A1) (Reich J Mol Diagn 13: 143 (2011)) | Secreted |
| Collagen type 1 alpha 2 (Col1A2) (Fragiadaki Matrix Biol 30: 396 (2011)) | Secreted |
| Collagen type 5 alpha 2 (Col5A2) (Liu Hypertension 55: 974 (2010)) | Secreted |
| C reactive protein (CRP) (Trimarchi Int J Nephrol Renovasc Dis 5: 1 (2012)) | Secreted |
| Connective tissue growth factor (CTGF/CNN2) (Lan Clin Exp Pharmacol Physiol (epub Dec. 28, 2011)) | Secreted |
| Cathepsin B (CTSB) (Todorov Kidney Blood Press Res 24: 75 (2001)) | Intracellular |
| Cubilin (CUBN) (Amsellem J Am Soc Nephrol 21: 1859 (2010)) | Surface |
| CXCL5 (Maity Cytokine 54: 61 (2011)) | Secreted |
| Tissue factor (LOC396677) (F3) (Kourtzelis Blood 116: 631 (2010)) | Surface |
| Fibrillin 1 (FBN1) (Gaikwad Biochem J 432: 333 (2010)) | Secreted |
| Ficolin (collagen/fibrinogen domain containing) 3 (FCN3) (Higgins Mol Biol Cell 15: 649 (2004)) | Secreted |
| Fibroblast growth factor receptor 2 (FGFR2) (Ford Kidney Int 51: 1729 (1997)) | Secreted/ surface |
| Fibromodulin (FMOD) (Lee J Biol Chem 286: 6414 (2011)) | Secreted |
| Fibronectin (FN1) (Waalkes BMC Cancer 10: 503 (2010)) | Secreted |
| Fucosyltransferase 6 (FUT6) (Higgins Mol Biol Cell 15: 649 (2004)) | Intracellular |
| Glial cell line-derived neurotrophic factor (GDNF) (Saito Hum Pathol 42: 848 (2011)) | Secreted |
| Cybb, NOX2 (Gp91-phox) (Kinoshita Transl Res 158: 235 (2011)) | Surface |
| Glutathione S-transferase A2 (GSTA2) (Leonard FASEB J 20: 2624 (2006)) | Intracellular |
| GST Yb-1 protein (GSTM1-1) (Abruzzo Free Radic Res 44: 563 (2010)) | Intracellular |
| Glutathione S-transferase mu 2 (GSTM2-LOC780435) (Yuan Am J Physiol Regul Integr Comp 284: R1219 (2003)) | Intracellular |
| Glutathione S-transferase alpha (GSTA1) (GST-α) (Obeidat Nephrol Dial Transplant 26: 3038 (2011)) | Intracellular |
| Isocitrate dehydrogenase 3 NAD beta (IDH3B) (Dange J Biol Chem 285: 20520 (2010)) | Intracellular |
| Interleukin 1b (IL1b) (Grishman Pediatr Res (epub Feb. 15, 2012)) | Secreted |
| Interleukin 6 (IL-6) (Zhang Hypertension 59: 136 (2012)) | Secreted |
| CXCL8 (IL8) (Maity Cytokine 54: 61 (2011)) | Secreted |
| Inducible nitric oxide synthase (iNOS (NOS2)) (Ma Am J Physiol Renal Physiol 300: F1410 (2011)) | Intracellular |
| Ketohexokinase (fructokinase) (KHK) (Higgins Mol Biol Cell 15: 649 (2004)) | Intracellular |
| Lamini beta 1 (LAMB1) (Sataranatarajan Am J Pathol 171: 1733 (2007)) | Secreted |
| Lipocalin 2 (NGAL) (LCN) (Zerega Eur J Cell Biol 79: 165 (2000)) | Secreted |
| Maltase-glucoamylase (MGAM) (Higgins Mol Biol Cell 15: 649 (2004)) | Surface |
| Matrix metallopeptidase 2 (MMP2) (Mazanowska Transplant Proc 43: 3000 (2011)) | Secreted |
| Matrix metallopeptidase 9 (MMP9) (Begatta J Am Soc Nephrol 20: 787 (2009)) | Secreted |
| Metallothionein (MT1A) (Klosterhalfen Biochem Pharmacol 52: 1201 (1996)) | Intracellular |

TABLE 4-continued

| Gene (Reference) | Location |
|---|---|
| Neuronal nitric oxide synthase 1 (nNOS (NOS1)) (Zheng Am J Physiol Heart Circ Physiol 301: H2402 (2011)) | Surface |
| Prostaglandin E synthase 2 (PTGES2) (Kopp Hypertension 57: 640 (2011)) | Surface |
| Prostaglandin endoperoxide synthase 1 (COX-1) (PTGS1) (Liu Am J Physiol Renal Physiol (epub Feb. 1, 2012)) | Intracellular |
| Replication protein A1 (RPA-1) (Liu Mol Cell Biol 31: 4298 (2011)) | Intracellular |
| Replication protein A2 (RPA-2) (Nakaya J Biochem 148: 539 (2010)) | Intracellular |
| Shingosine-1-phosphate receptor 1 (S1PR1/EDG1) (Higgins Mol Biol Cell 15: 649 (2004)) | Surface |
| Serpin peptidase inhibitor clade F (SerpinF1) (Sigdel Proteomics Clin Appl 4: 32 (2010)) | Secreted |
| Secreted acidic cystein-rich glycoprotein (osteonectin) (SPARC) (Lloyd-Burton J Comp Neurol (epub Dec. 15, 2011)) | Secreted |
| Transforming growth factor beta 1 (TGFB1) (Lantero Mol Neurobiol 45: 76 (2012)) | Secreted |
| Transforming growth factor beta 2 (TGFB2) (Lantero Mol Neurobiol 45: 76 (2012)) | Secreted |
| Tyrosine hydroxylase (TH) (Rothmond Anat Embryol (Berl) 209: 41 (2004)) | Intracellular |
| Thrombospondin 1 (THBS1) (Sun Kidney Blood Press Res 35: 35 (2012)) | Intracellular |
| Tight junction protein (TJP1 (ZO-1)) (Higgins Mol Biol Cell 15: 649 (2004)) | Surface |
| Thioredoxin (TXN) (Kasuno Rinsho Byori 59: 189 (2011)) | Intracellular/ secreted |
| Vascular endothelial growth factor A (VEGFA) (Chade F1000 Med Rep (epub Jan. 3, 2012)) | Secreted |
| SMAD family member 6 (SMAD6 (MADH6)) (Higgins Mol Biol Cell 15: 649 (2004)) | Intracellular |
| Galanin prepropeptide (GAL) (Longley Neuroscience 55: 253 (1993)) | Secreted |
| Nephrin (NPHS1) (Ruotsalainen Proc Natl Acad Sci USA 96: 7962 (1999)) | Surface |

Additional screens may be carried out to evaluate changes in various non-protein candidate biomarkers such as NE, DBN, or other catecholamines in renal tissue.

Example 2

In Vitro Target Biomarker Screening (Human)

Additional candidate target biomarkers were evaluated through in vitro screening of human vascular and neuronal cells. Target biomarkers were identified based on changes in expression and/or secretion levels in response to experimental conditions that imitate heat-based stress to neuronal and vascular cells, thereby mimicking in vivo intervention. Specifically, cells were exposed to inflammatory stimulation and/or heat to simulate arterial RF ablation and SNS denervation in vivo.

Figure 22:
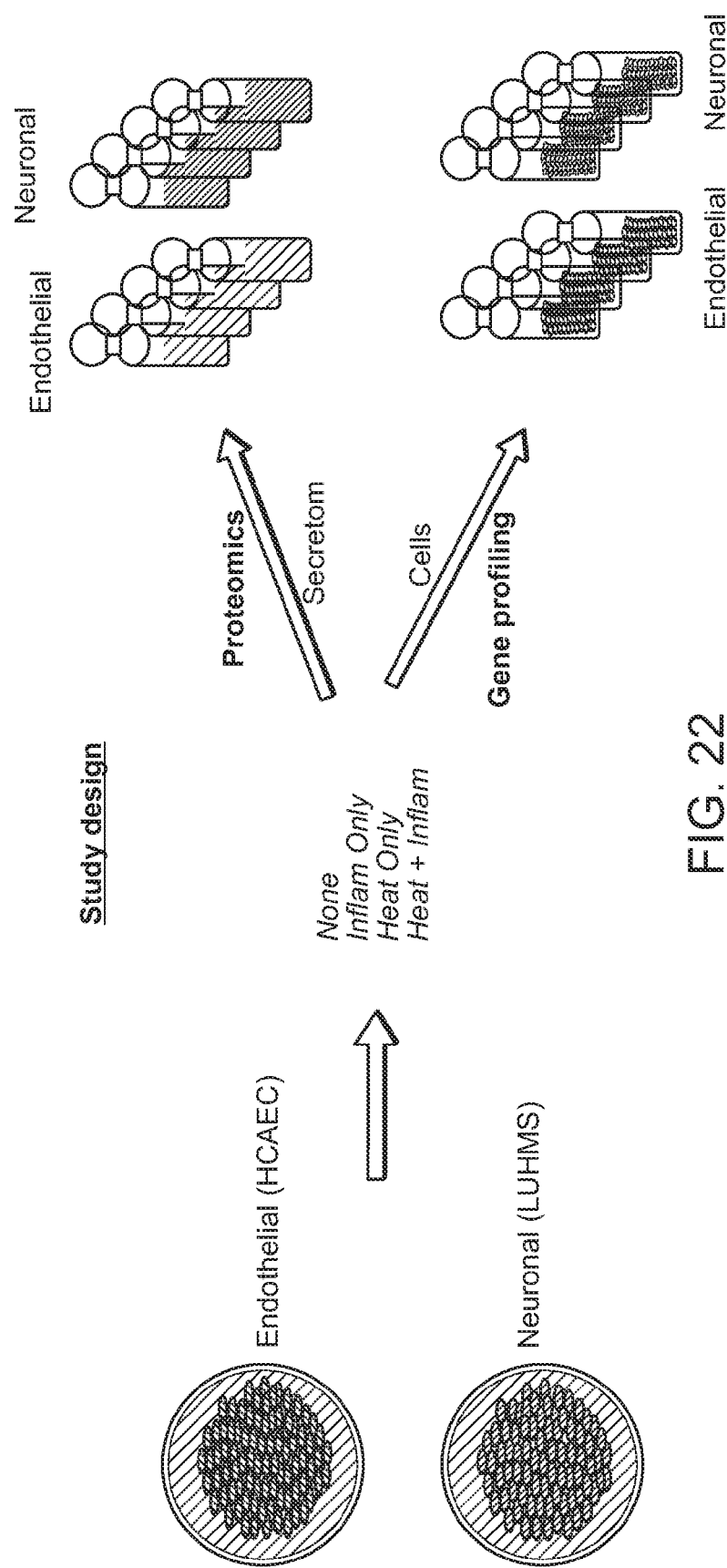
FIG. 22: General protocol for human in vitro gene expression/secretomics experiment.
Figure 23:
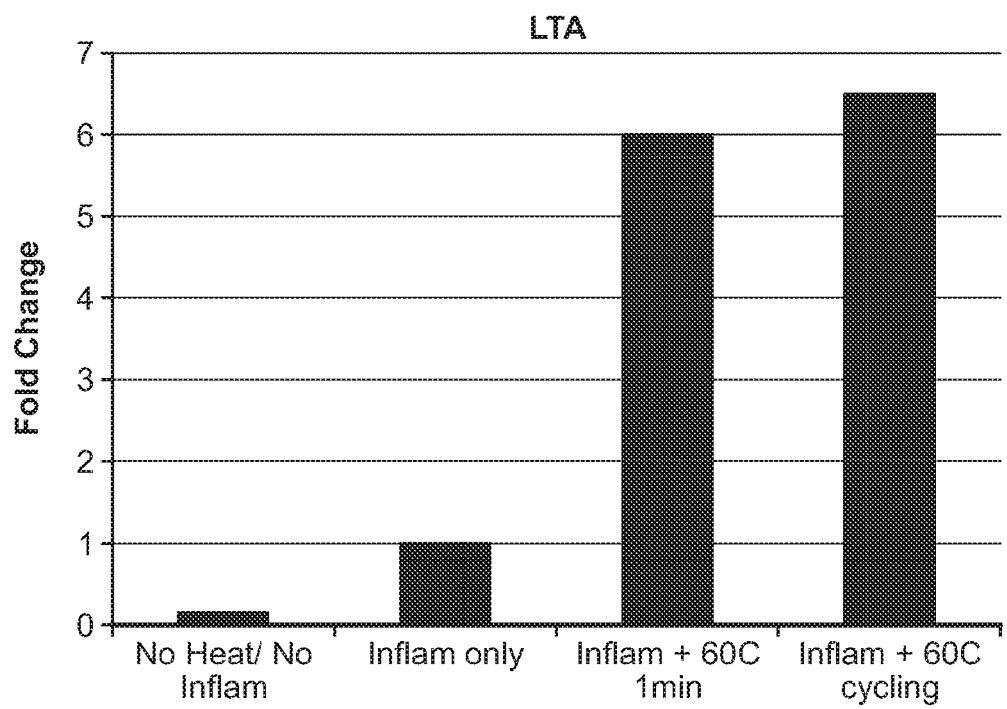
FIG. 23: Upregulation of LTA in response to inflammation/heat in endothelial cells.
Figure 24:
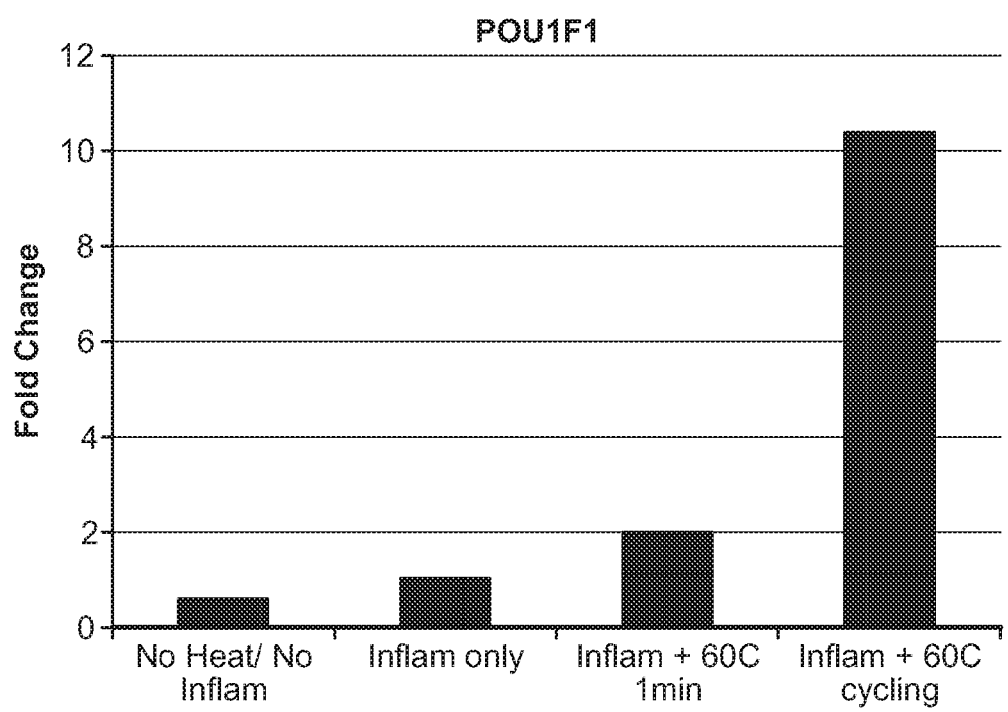
FIG. 24: Upregulation of POU1F1 in response to inflammation/heat in endothelial cells.
Figure 25:
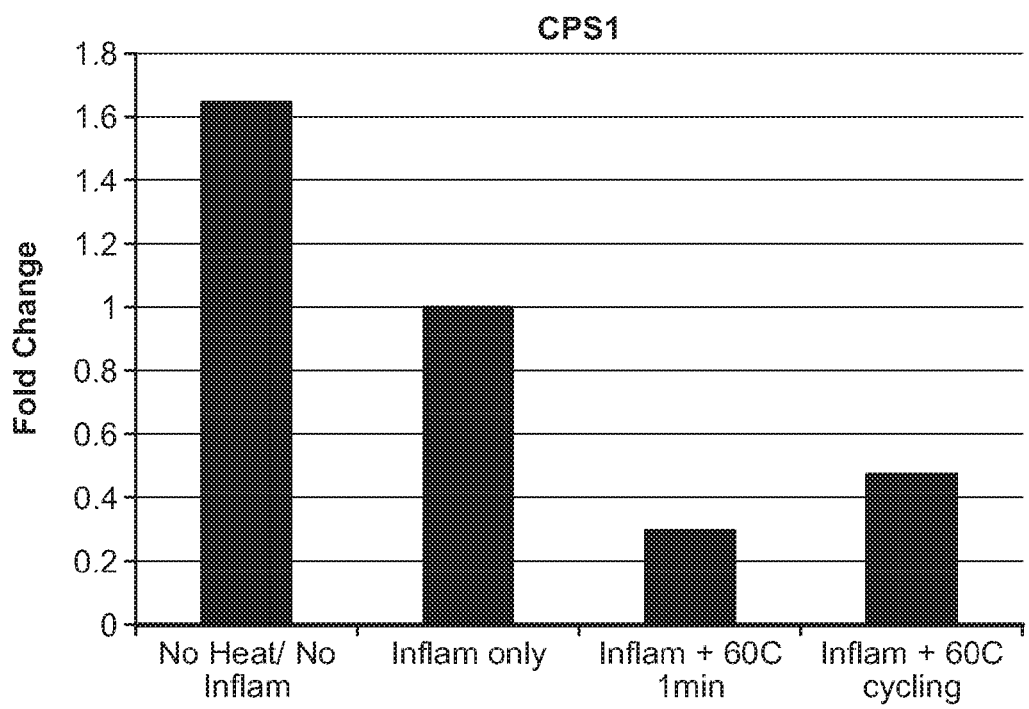
FIG. 25: Upregulation of CPS1 in response to inflammation/heat in endothelial cells.
Figure 26:
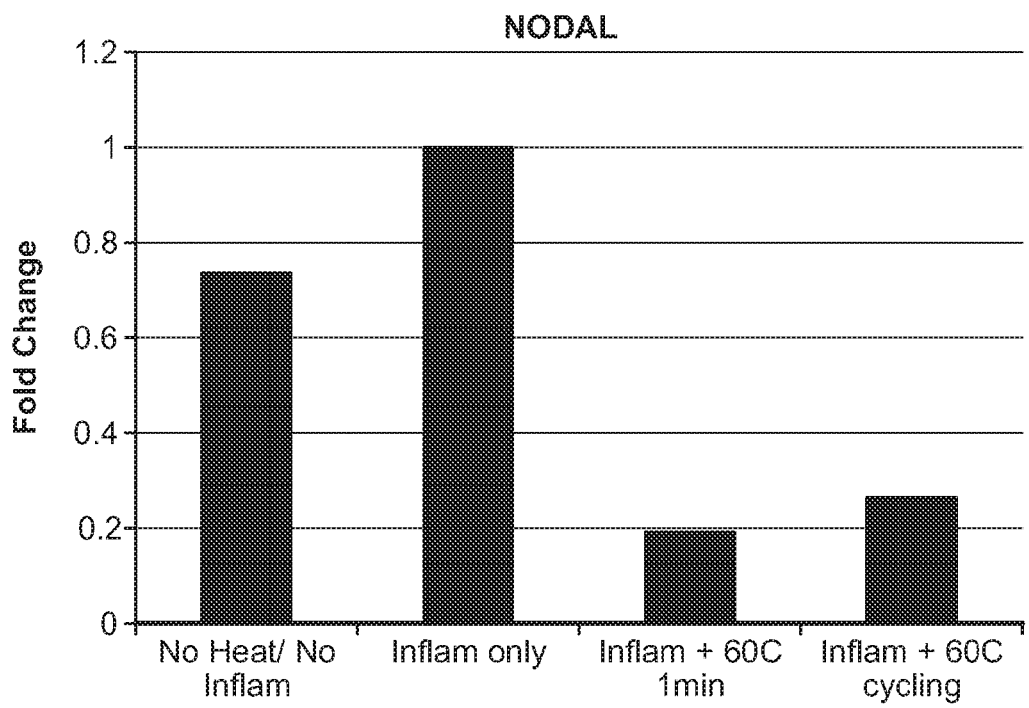
FIG. 26: Upregulation of NODAL in response to inflammation/heat.
Figure 27:
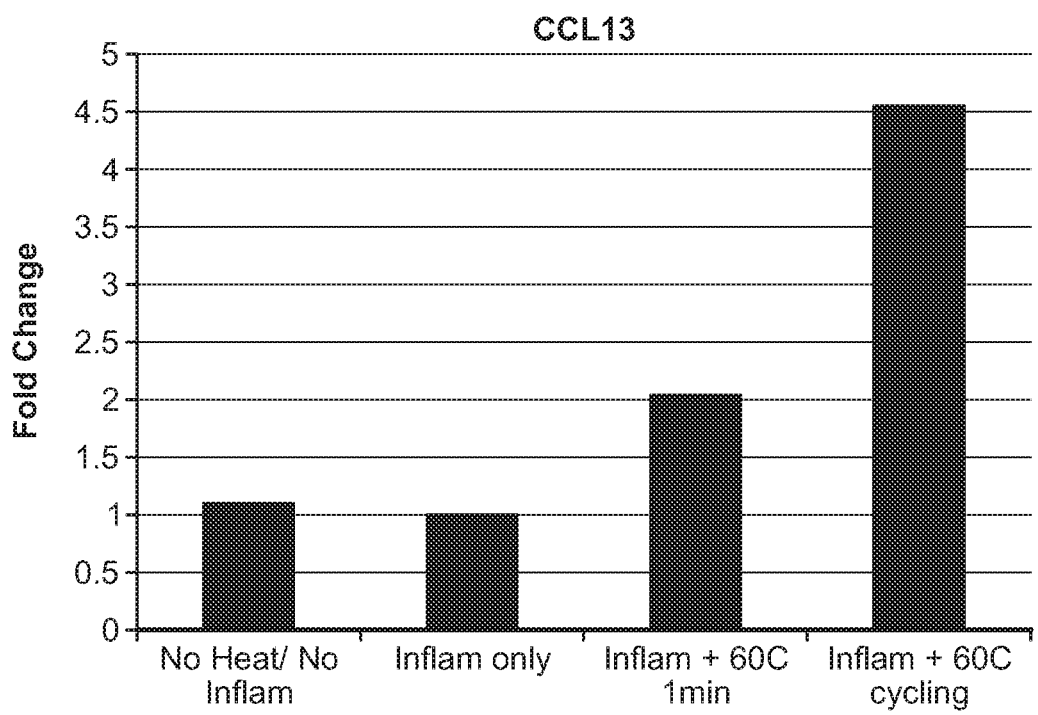
FIG. 27: Upregulation of CCL13 in response to inflammation/heat in endothelial cells.
Figure 28:
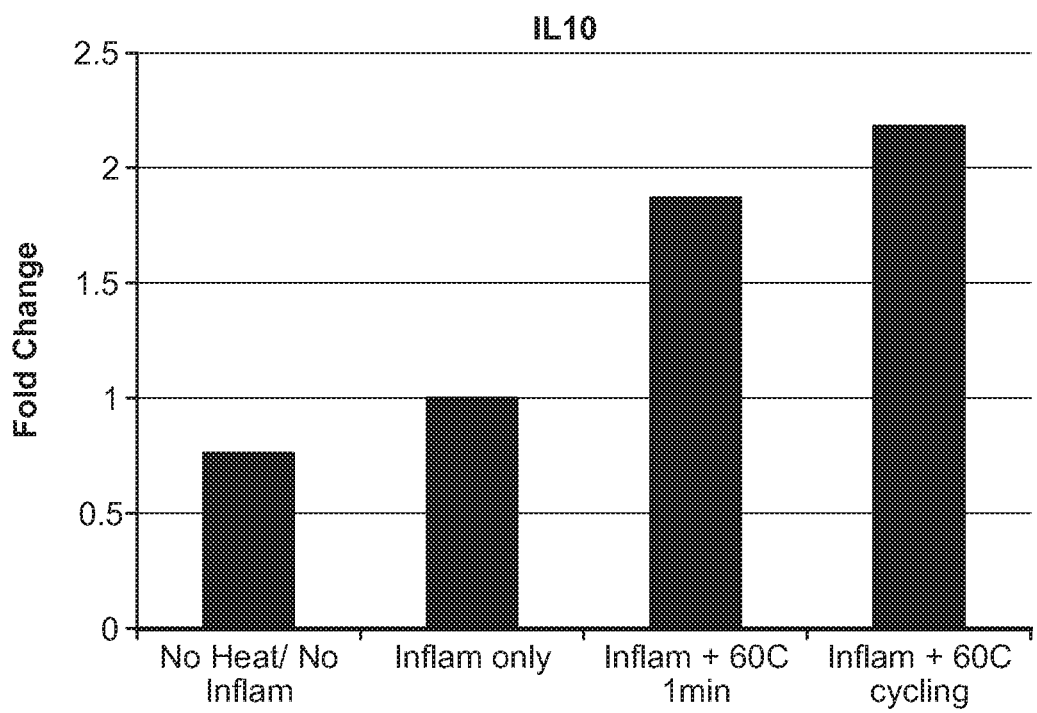
FIG. 28: Upregulation of IL-10 in response to inflammation/heat in endothelial cells.

A first set of gene profiling and secretomics experiments were performed according to the protocol set forth in FIG. 22. In this first set of experiments, Human Coronary Artery Endothelial Cells (HCAEC), Human Coronary Artery Smooth Muscle Cells (HCASMC), and Lund human mesencephalic cells (LUHMES) were exposed to inflammatory conditions and/or heat, following by secretomic and gene profiling studies. Inflammatory conditions were obtained by treating cultured cells with various inflammatory cytokines (e.g., TNFα or IL-β at about 5 ng/ml) to mimic the cellular environment during neuromodulatory intervention. Cells exposed to heat were subjected to an elevated temperature of 60° C. for 90 seconds and allowed to recover at 37° C. for various time periods (e.g., 30-120 seconds). Cell culture samples were obtained for proteomics analysis prior to inflammation/heat exposure and at 1, 5, and 10 minutes post-exposure.

Cells were lysed, and gene profiling was performed. This resulted in the identification of 19 proteins that exhibited an acute response to inflammation and heat. These proteins are listed in Table 5. Results for LTA, POU1F1, CPS1, NODAL, CCL13, and IL-10 are set forth in FIGS. 23-28, respectively.

TABLE 5

| Gene | Gene Product Function/Description |
|---|---|
| CASP10 | Cysteinyl aspartate protease involved in signal transduction pathways of apoptosis, necrosis, and inflammation |
| CCL13 (MCP4) | Chemotactic factor that attracts monocytes, lymphocytes, basophils, and eosinophils, but not neutrophils |
| CCND1 | Regulatory component of cyclin D1-CDK4 (DC) complex that phosphorylates and inhibits members of the retinoblastoma (RB) protein family and regulates cell cycle during G(1)/S transition |
| CD70 | Cytokine that binds CD27, plays role in T-cell activation, induces proliferation of co-stimulated T-cells and enhances generation of cytolytic T-cells |
| CPS1 | Mitochondrial enzyme catalyzes synthesis of carbamoyl phosphate from ammonia and bicarbonate, involved in urea cycle of ureotelic animals, plays important role in removing excess urea |
| CRYAB | Members of small heat shock protein (sHSP) family, acts as molecular chaperone by holding proteins in large soluble aggregates, elevated expression in many neurological diseases |
| DNAJB1 | Interacts with Hsp70, stimulates ATPase activity |
| DNAJB11 | |
| HSPA1A | |
| HSPA1B | |
| HSPB6 | Expressed in multiple tissues, most highly constitutively expressed in different types of muscle including vascular, airway, colonic, bladder, uterine smooth muscle, cardiac muscle, and skeletal muscle, has specific functions for vasodilation, platelet function, and insulin resistance in smooth and cardiac muscle |
| IL-10 | Anti-inflammatory cytokine with pleiotropic effects in immunoregulation and inflammation, inhibits synthesis of various cytokines including IFN-γ, IL-2, IL-3, TNF, and GM-CSF produced by activated macrophages and helper T-cells |
| KIT | Receptor for stem cell factor (mast cell growth factor), has tyrosine-protein kinase activity, ligand binding leads to autophosphorylation and associate with substrates such as phosphatidylinositol 3-kinase (Pi3K) |
| LTA | Member of TNF family produced by lymphocytes, highly inducible, forms heterotrimers with lymphotoxin beta |
| MYLK3 | Myosin light chain kinases (MLCKs) are serine/threonine kinases divided into two subtypes, MLCK1 subtype is found in smooth muscle and phosphorylates myosin II regulatory light chains at Ser19 |
| NODAL | Member of TGF-β superfamily, may be essential for mesoderm formation and subsequent organization of axial structures in early embryonic development |
| NPY1R | NPY receptors are Gi/o-protein-coupled receptors divided into four subtypes (Y1, Y2, Y4, Y5), mediate diverse range of biological actions including stimulation of food intake and anxiolysis |
| POU1F1 | Member of TNF ligand family, part of POU family of transcription factors that regulate mammalian development |
| TCP1 | Molecular chaperone, assists folding of proteins upon ATP hydrolysis, may play a role in formation of BBSome (complex involved in ciliogenesis), plays a role in actin and tubulin folding |

Figure 29:
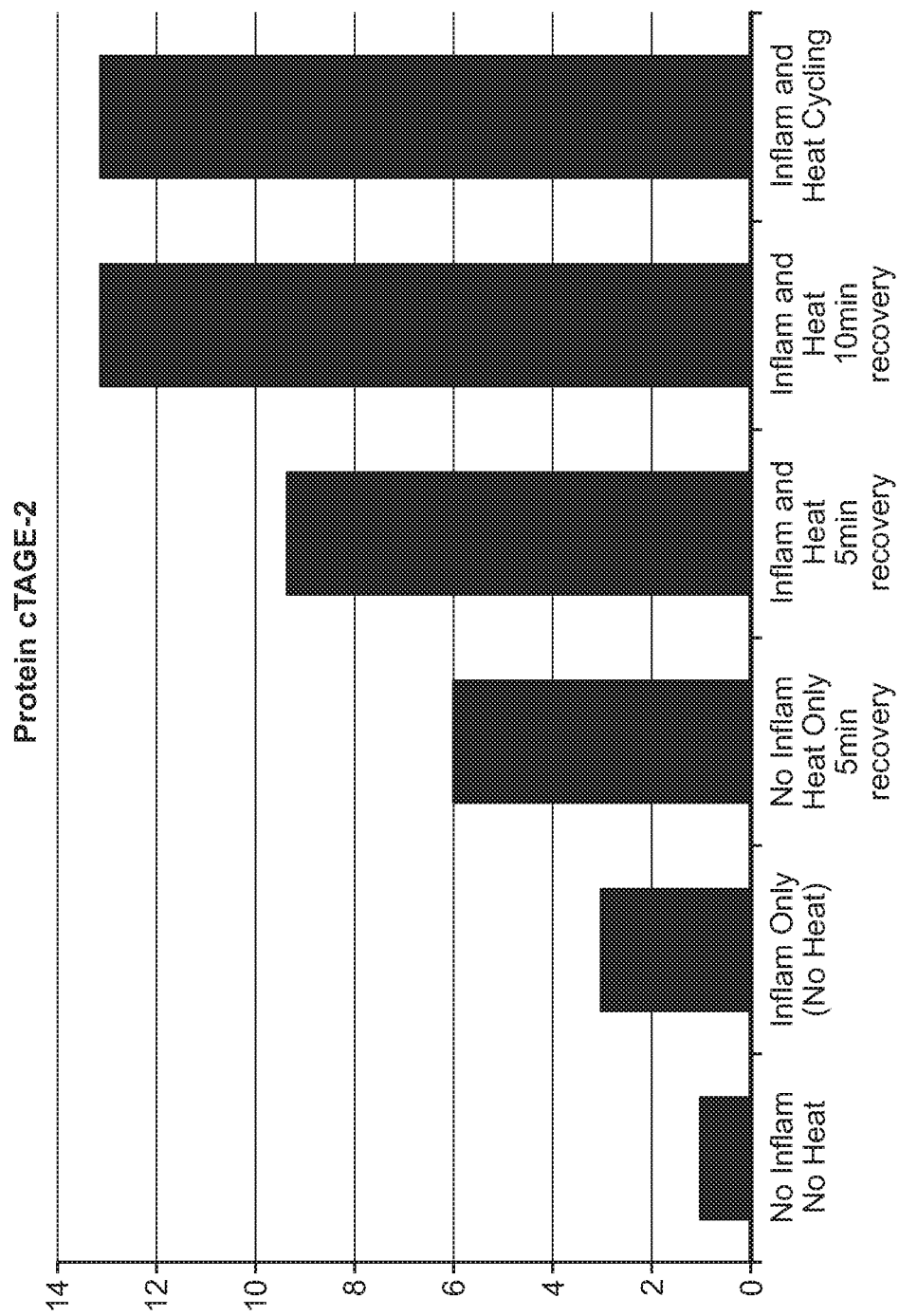
FIG. 29: Increased secretion of cTAGE-2 in response to inflammation/heat in endothelial cells.

The collected cell culture samples included cultured media from the treated cells (i.e., conditioned media) into which the cells can actively secrete proteins, peptides, and non-protein molecules in response to inflammation and heat. These cell culture samples were subjected to secretomics to identify proteins released into culture in response to inflammation and heat. Secretomics assays were performed using iTRAQ methodology (Wiśniewski Arch Pathol Lab Med 132:1566 (2008)). Samples were diluted, digested with trypsin, and iTRAQ labeled using 8-Plex reagent. The resultant complex protein digests were pooled together for MudPIT analysis. Each fraction was analyzed by LC-MS/MS, for acquisition of mass spectroscopy data with the inclusion of iTRAQ quantitation data. The 13 proteins listed in Table 6 exhibited increased secretion after exposure to inflammatory markers and heat. Results for cTAGE-2 are set forth in FIG. 29.

TABLE 6

| Protein | Gene | Function/Description |
| --- | --- | --- |
| Actin, cytoplasmic | ACTA2 | Major component of cytoskeletal part of contractile apparatus |
| S100 calcium binding protein A6 | CACY/2A9 | May function as calcium sensor and contribute to cellular calcium signaling, may function by interacting with other proteins and indirectly play a role in reorganization of the actin cytoskeleton and in cell motility |
| Cofilin-1 | CFL1 | Actin de-polymerization factor |
| Protein cTAGE-2 | CTAG1A1/CTAG21 | Antigen overexpressed in many cancers, but also expressed in normal testis, potential role in survival/stress response |
| L-lactate dehydrogenase A | LDHA | Catalyzes conversion of L-lactate and NAD to pyruvate and NADH in final step of aerobic glycolysis |
| Transmembrane protein 141 | MGC141/TMEM141 | Multi-pass membrane protein |
| N-alpha-acetyltransferase 20 | NAA20/NAT5 | Catalytic subunit of NatB complex which catalyzes acetylation of N-terminal methionine residue of peptides beginning with Met-Asp-Glu, may play a role in normal cell cycle progression |
| Nucleoside diphosphate kinase B | NM23B | Major role in synthesis of nucleoside triphosphates other than ATP, acts as transcriptional activator of MYC gene, binds DNA non-specifically, exhibits histidine protein kinase activity |
| Phytanoyl-CoA deoxygenase, peroxisomal | PAHX/PHYH1 | Plays role in lipid metabolism |
| Prefoldin subunit 1 | PFDN1 | |
| Serine/threonine-protein kinase PLK2 | PLK-2 | Plays key role in synaptic plasticity and memory by regulating Ras and Rap protein signaling, induction by p53/TP53 suggests it may participate in mitotic checkpoint following stress, activated by phosphorylation of Thr-239 |
| Tubulin alpha-1B chain | TUBA1B | Part of microtubule, function in maintaining cell shape |
| Vimentin | VIM | Class-III intermediate filament found in various non-epithelial cells (especially mesenchymal cells), attached to the nucleus, endoplasmic reticulum, and mitochondria, either laterally or terminally involved with LARPS in stabilization of type I collagen mRNAs for CO1A1 and CO1A2 |

Cell culture samples were further subjected to proteomics analysis using commercially available ELISA assays for proteins encoded by the genes identified in Tables 5 and 6.

Figure 30:
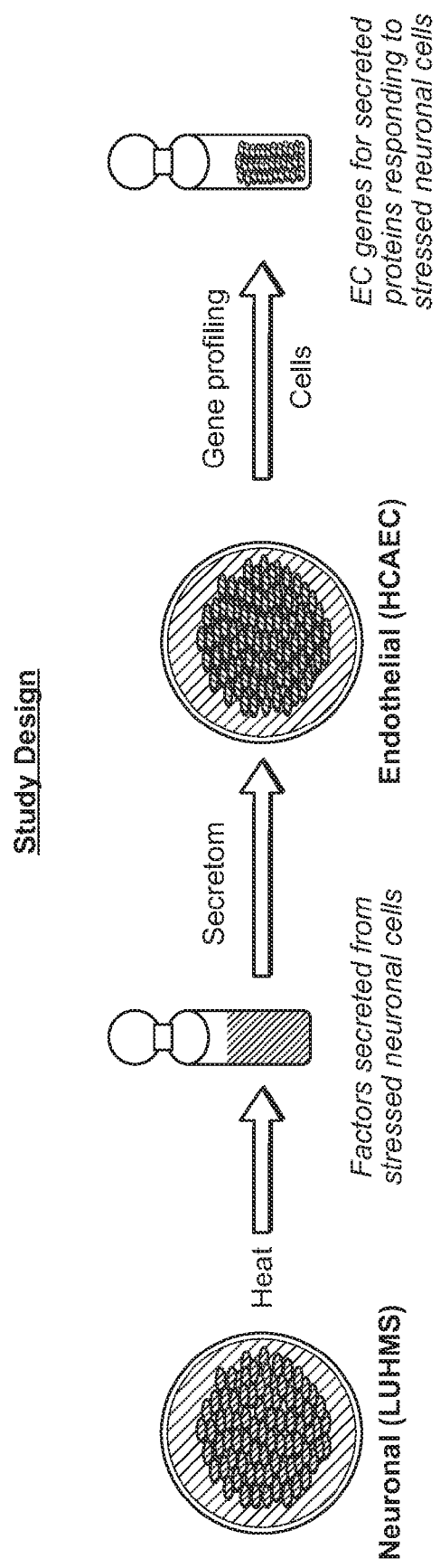
FIG. 30: General protocol for human in vitro gene expression/secretomics experiment.
Figure 31A:
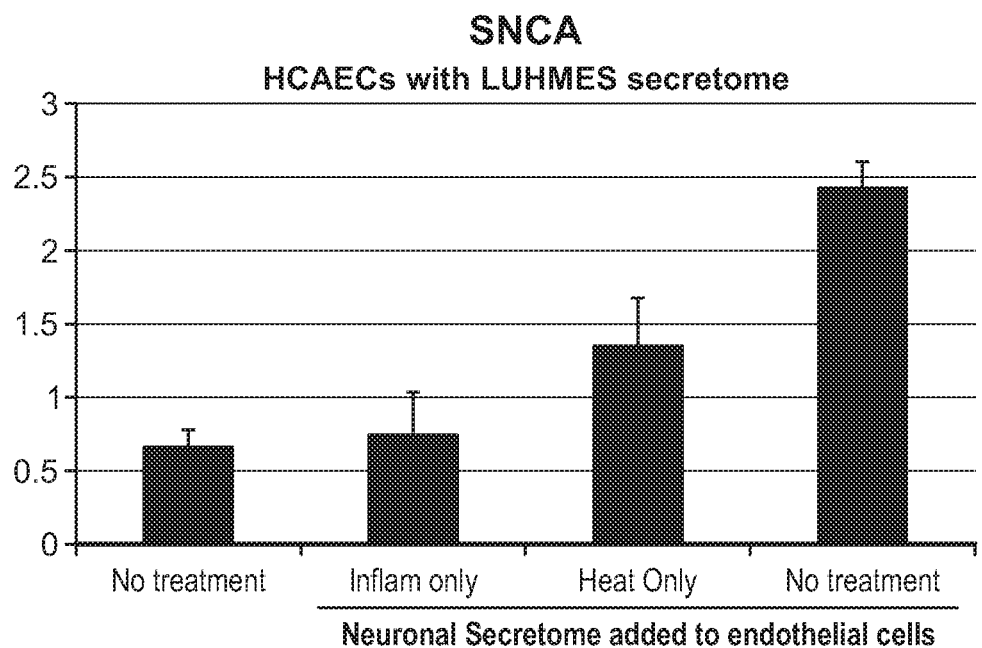
FIG. 31: A. Upregulation of SNCA expression by HCAECs in the presence of secreted proteins from LUHMES treated with inflammation/heat. B. Upregulation of SNCA expression by HCAECs in the presence of added neuronal (recombinant) factor BDNF.
Figure 31B:
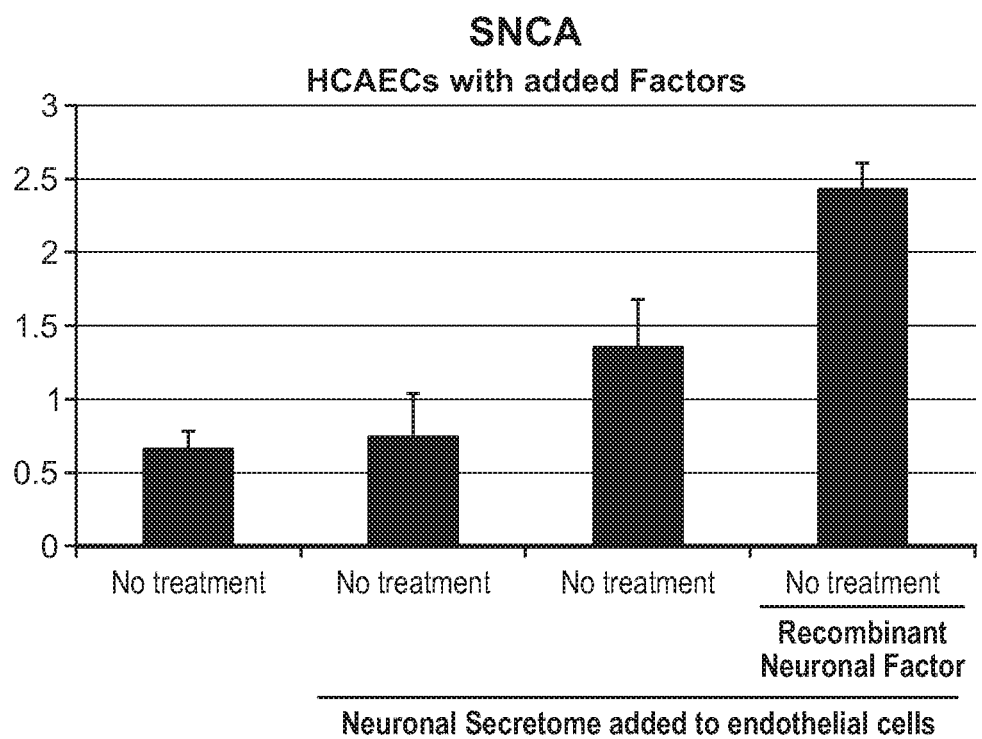
Figure 32:
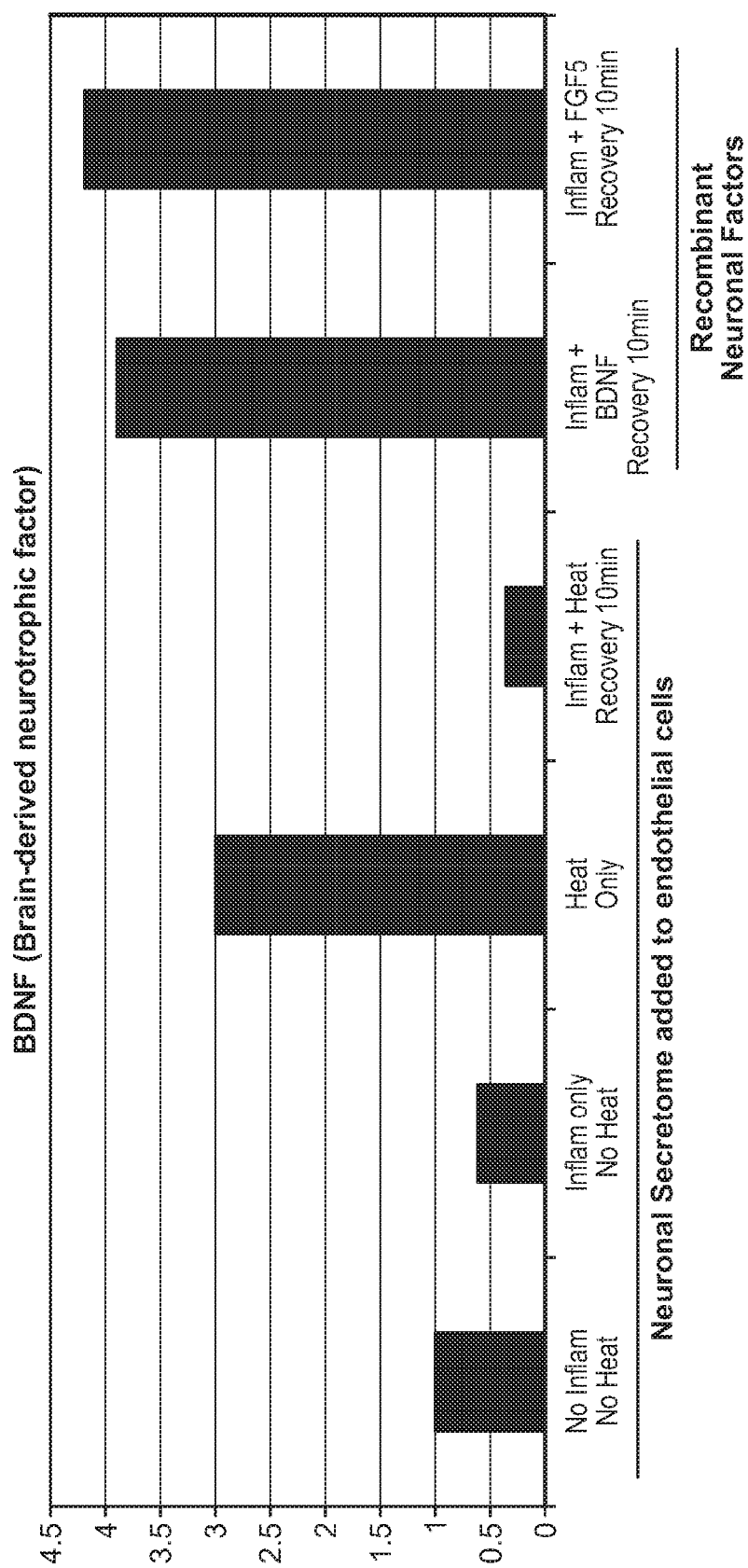
FIG. 32: Upregulation of BDNF expression in response to heat and/or inflammation in neuronal cells treated with inflammation/heat and with added neuronal (recombinant) factors BDNF or FGF5.
Figure 33:
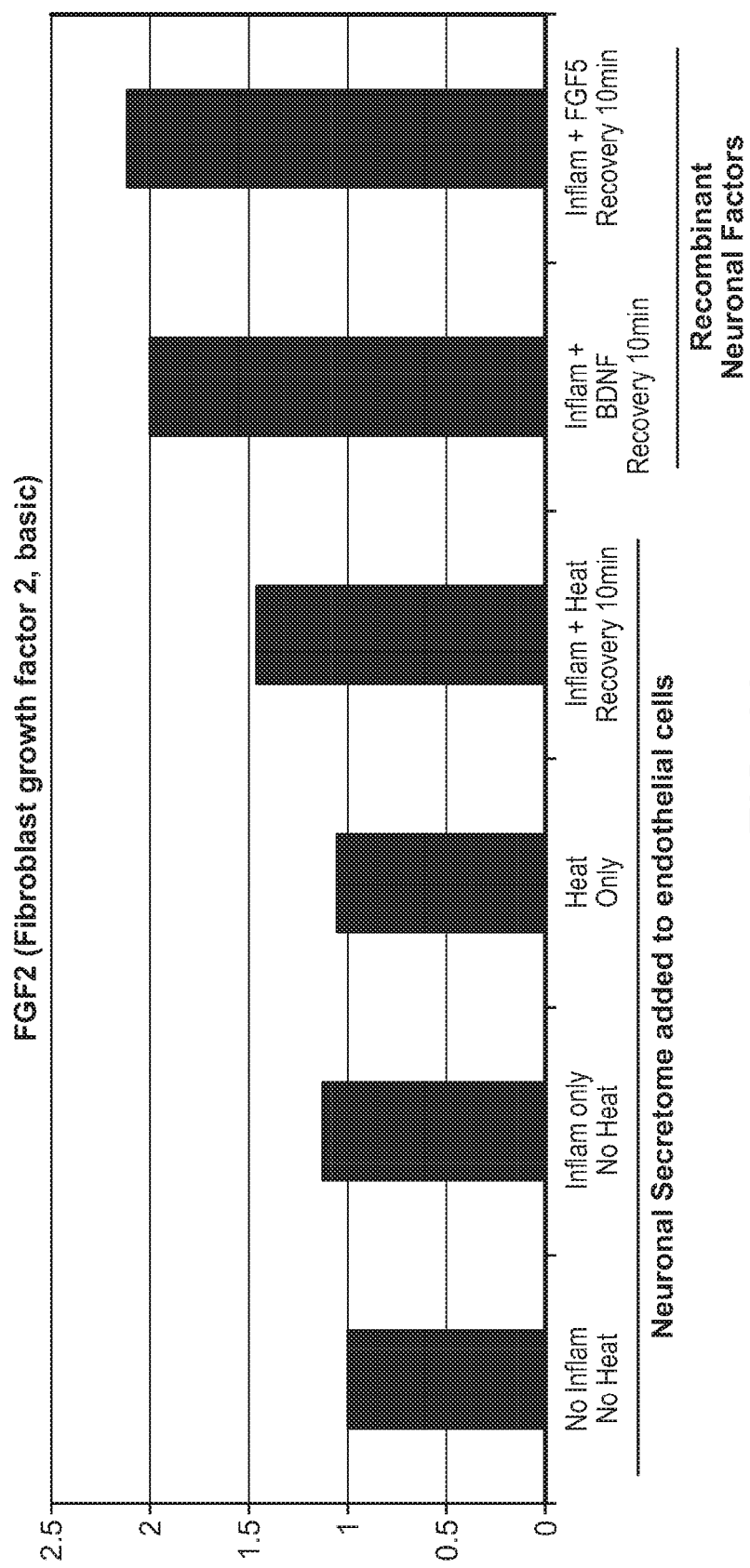
FIG. 33: Upregulation of FGF2 expression in response to heat and/or inflammation and with added neuronal (recombinant) factors BDNF or FGF5.
Figure 34:
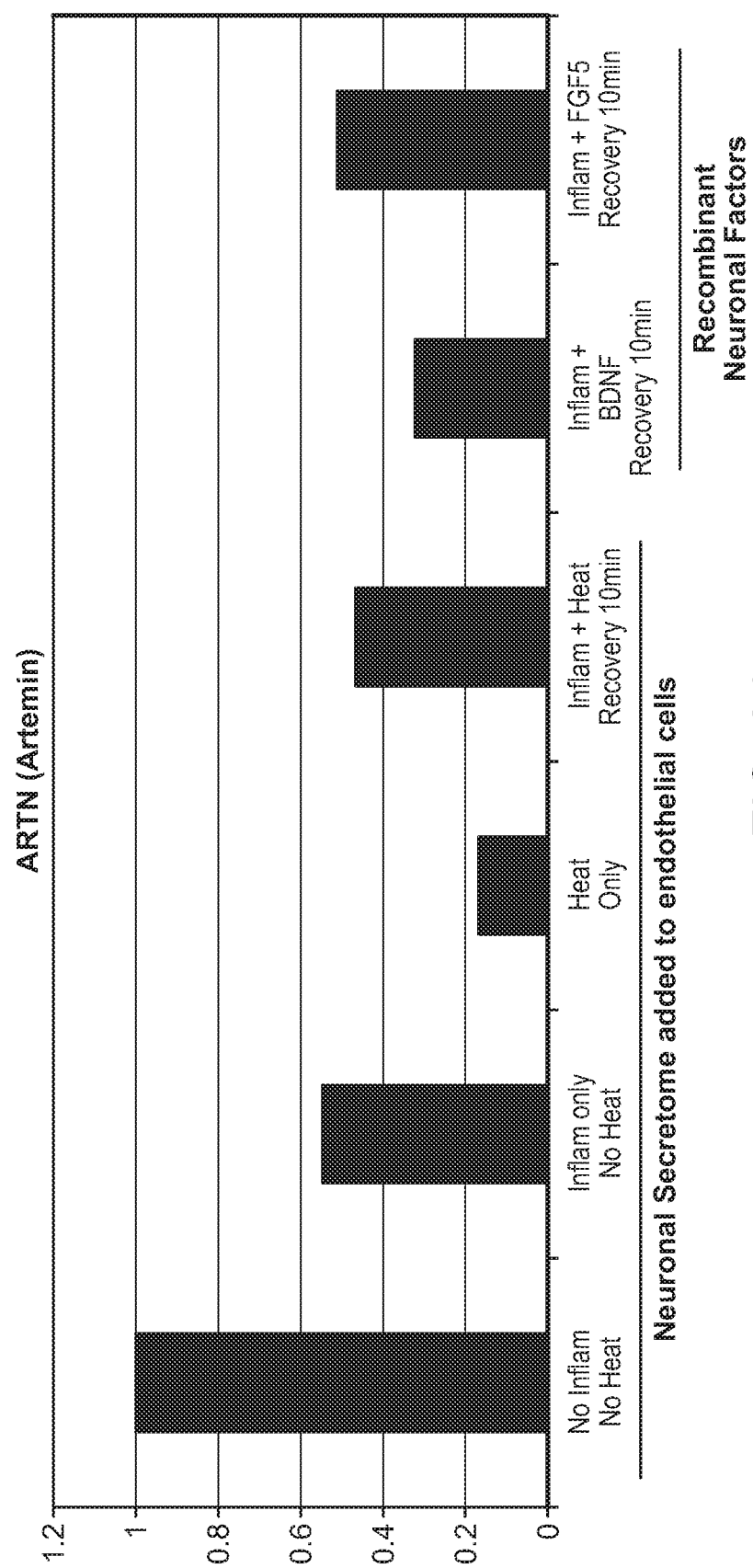
FIG. 34: Upregulation of ARTN expression in response to heat and/or inflammation and with added neuronal (recombinant) factors BDNF or FGF5.
Figure 35:
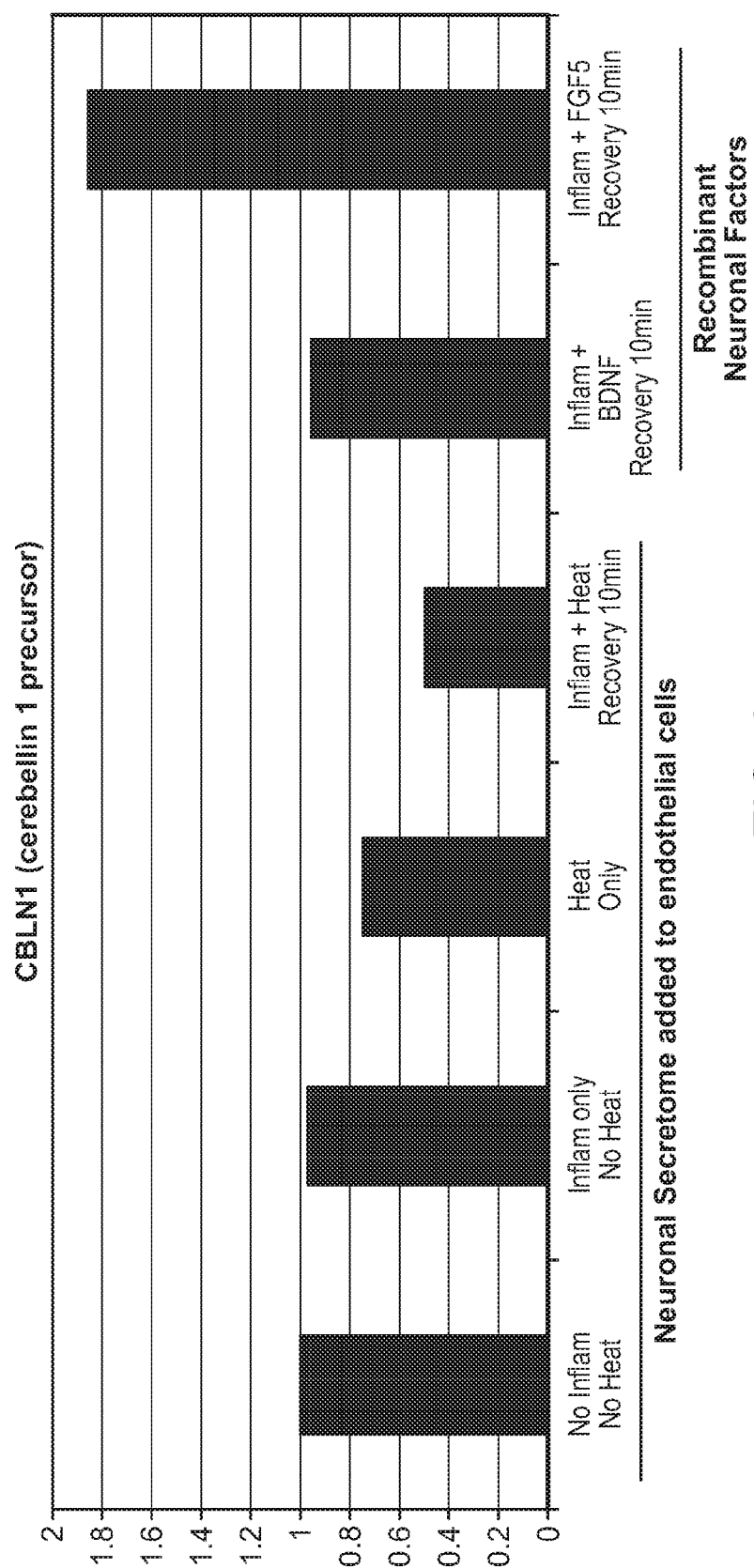
FIG. 35: Upregulation of CBLN1 expression in response to heat and/or inflammation and with added neuronal (recombinant) factors BDNF or FGF5.
Figure 36:
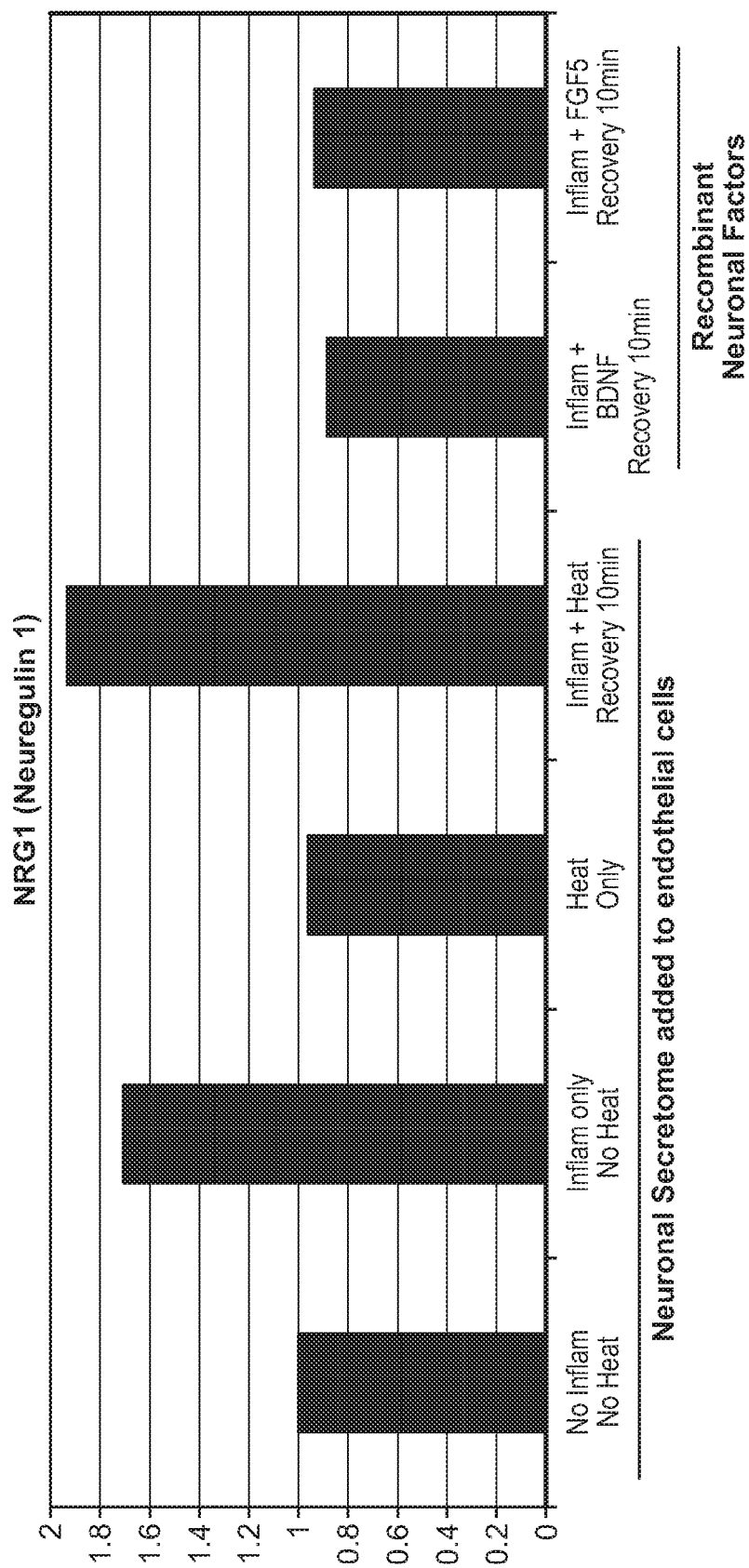
FIG. 36: Upregulation of NRG1 expression in response to heat and/or inflammation and with added neuronal (recombinant) factors BDNF or FGF5.
Figure 37:
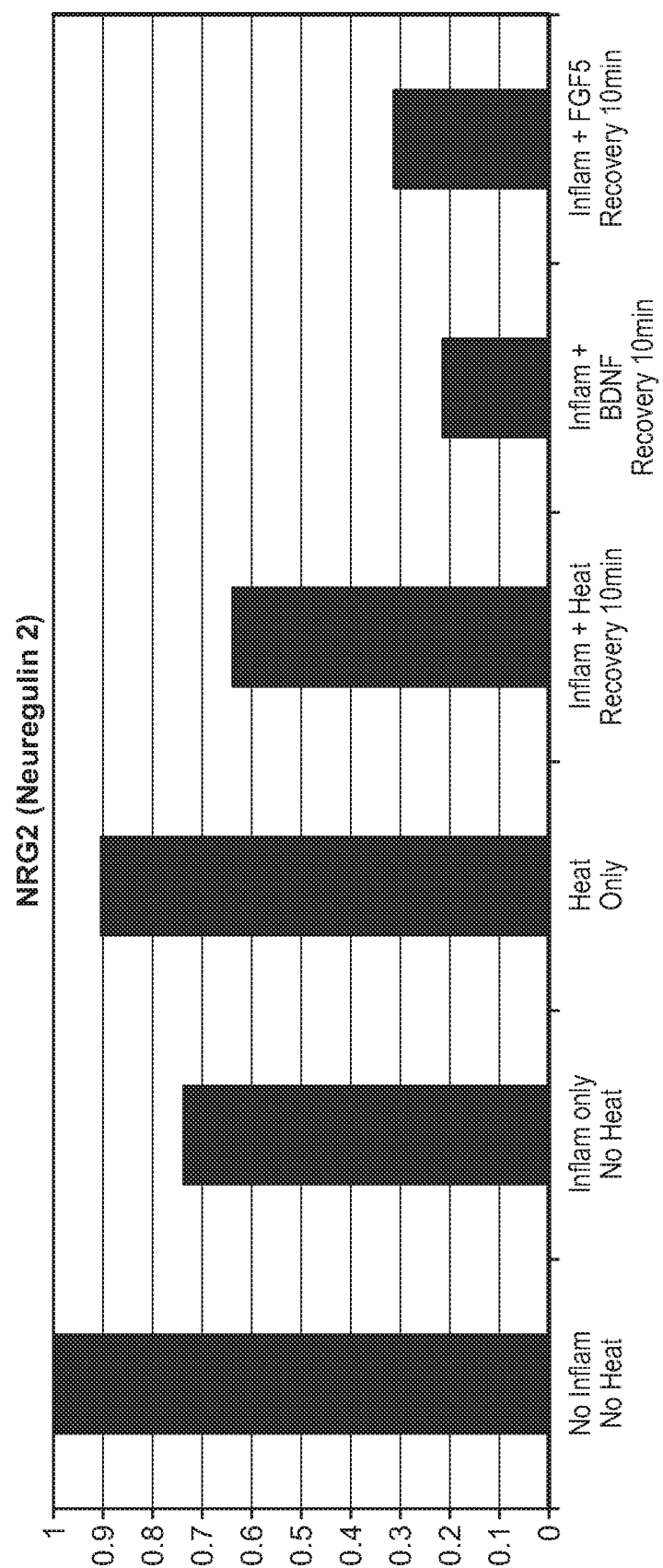
FIG. 37: Upregulation of NRG2 expression in response to heat and/or inflammation and with added neuronal (recombinant) factors BDNF or FGF5.
Figure 38:
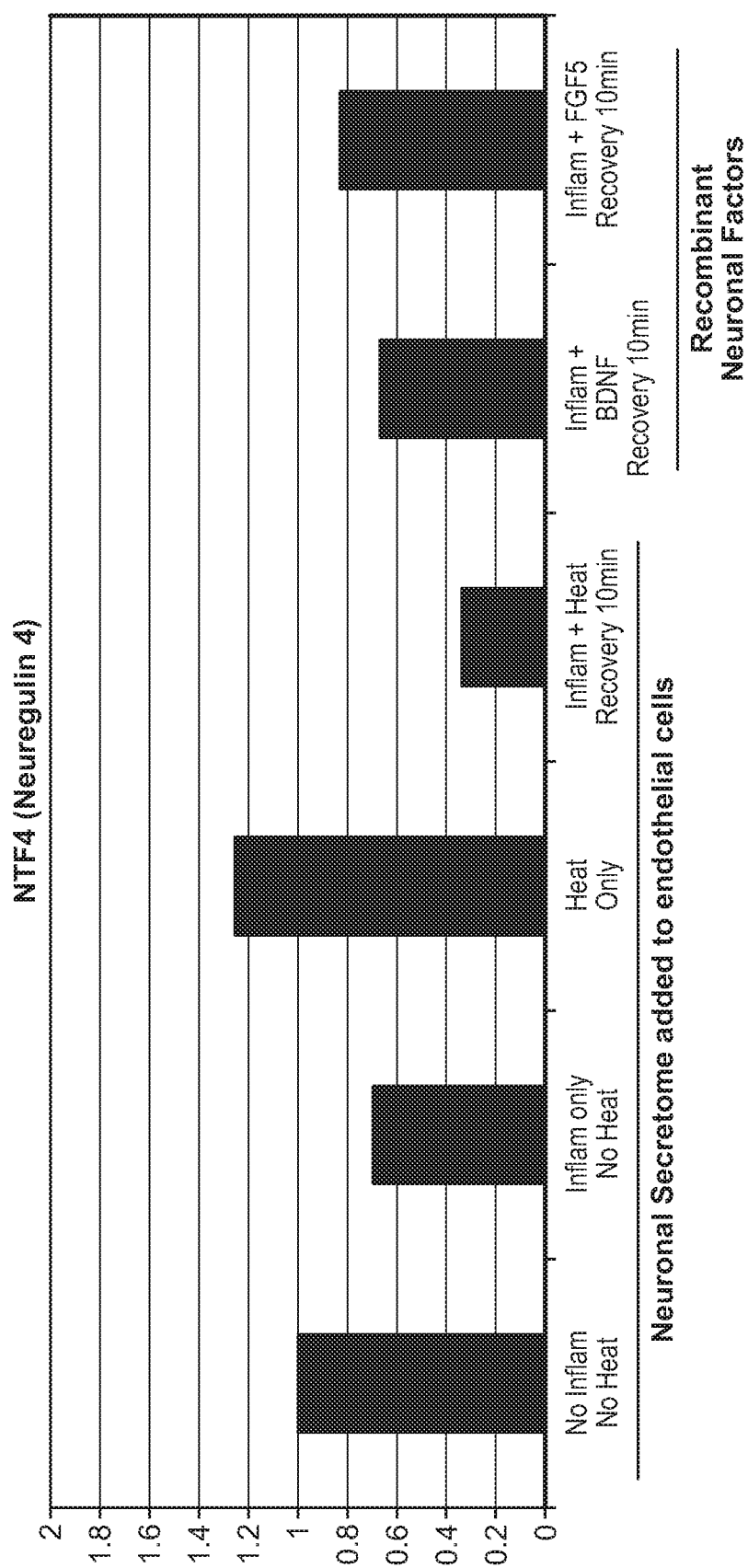
FIG. 38: Upregulation of NRG4 expression in response to heat and/or inflammation and with added neuronal (recombinant) factors BDNF or FGF5.
Figure 39:
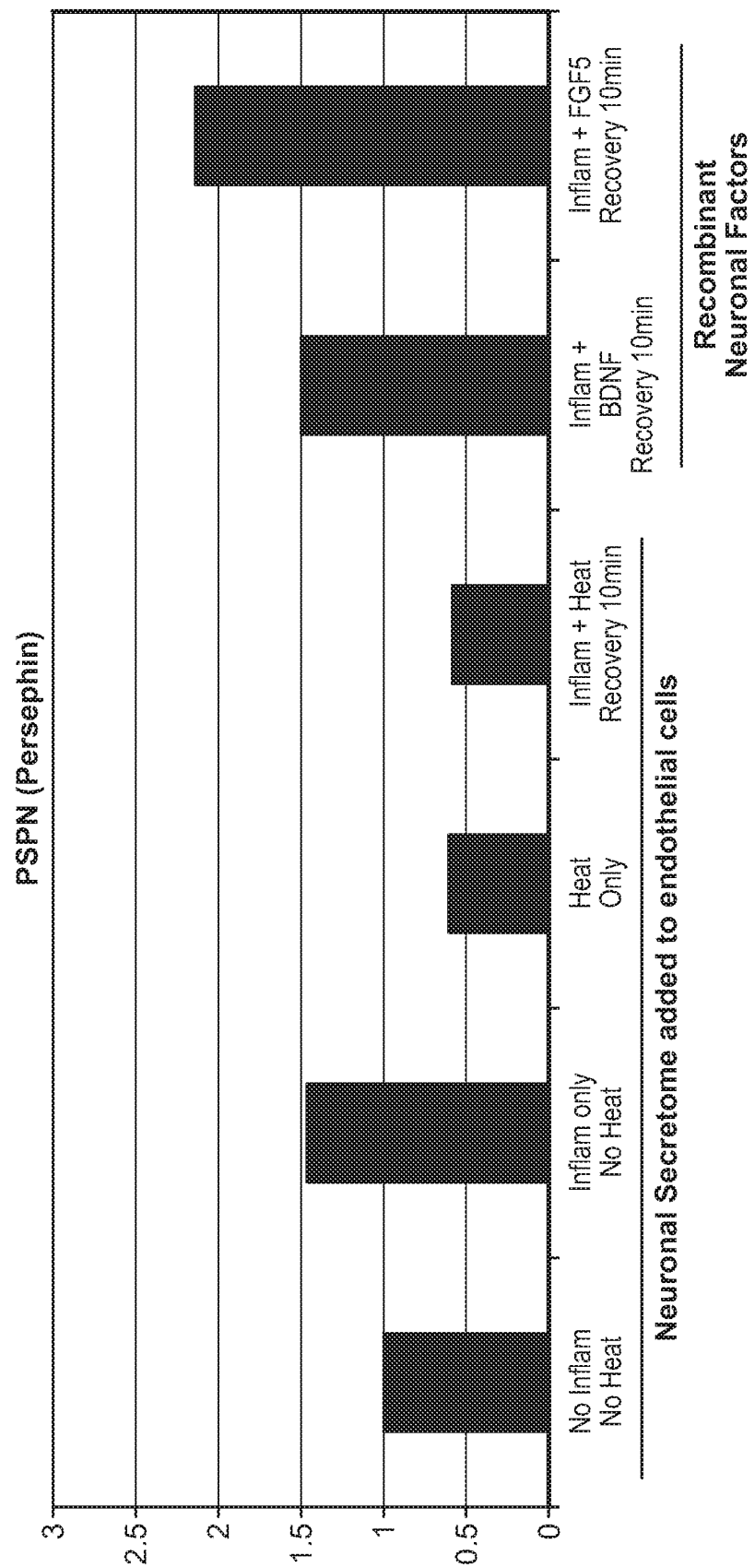
FIG. 39: Upregulation of PSPN expression in response to heat and/or inflammation and with added neuronal (recombinant) factors BDNF or FGF5.
Figure 40:
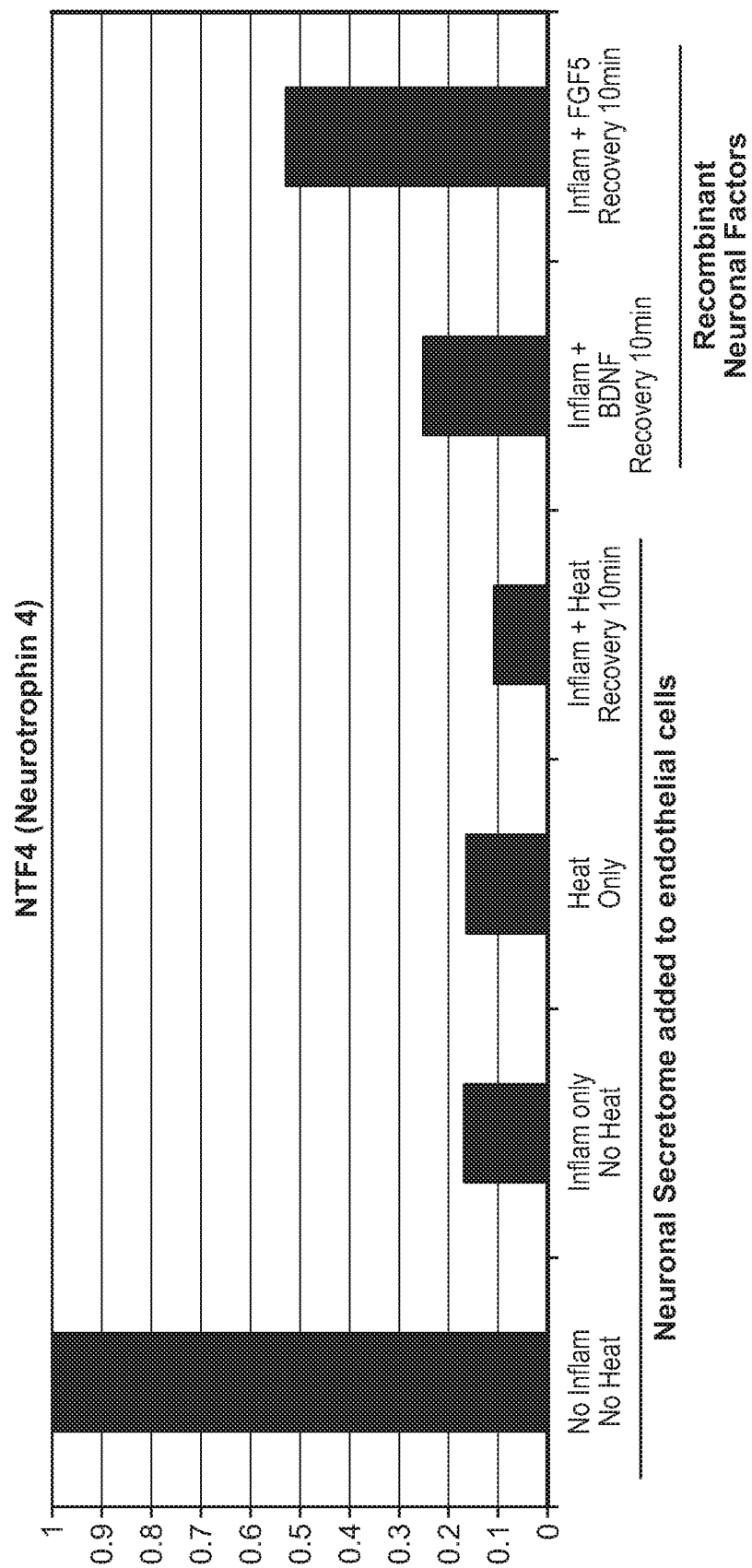
FIG. 40: Upregulation of NTF4 expression in response to heat and/or inflammation and with added neuronal (recombinant) factors BDNF or FGF5.
Figure 41:
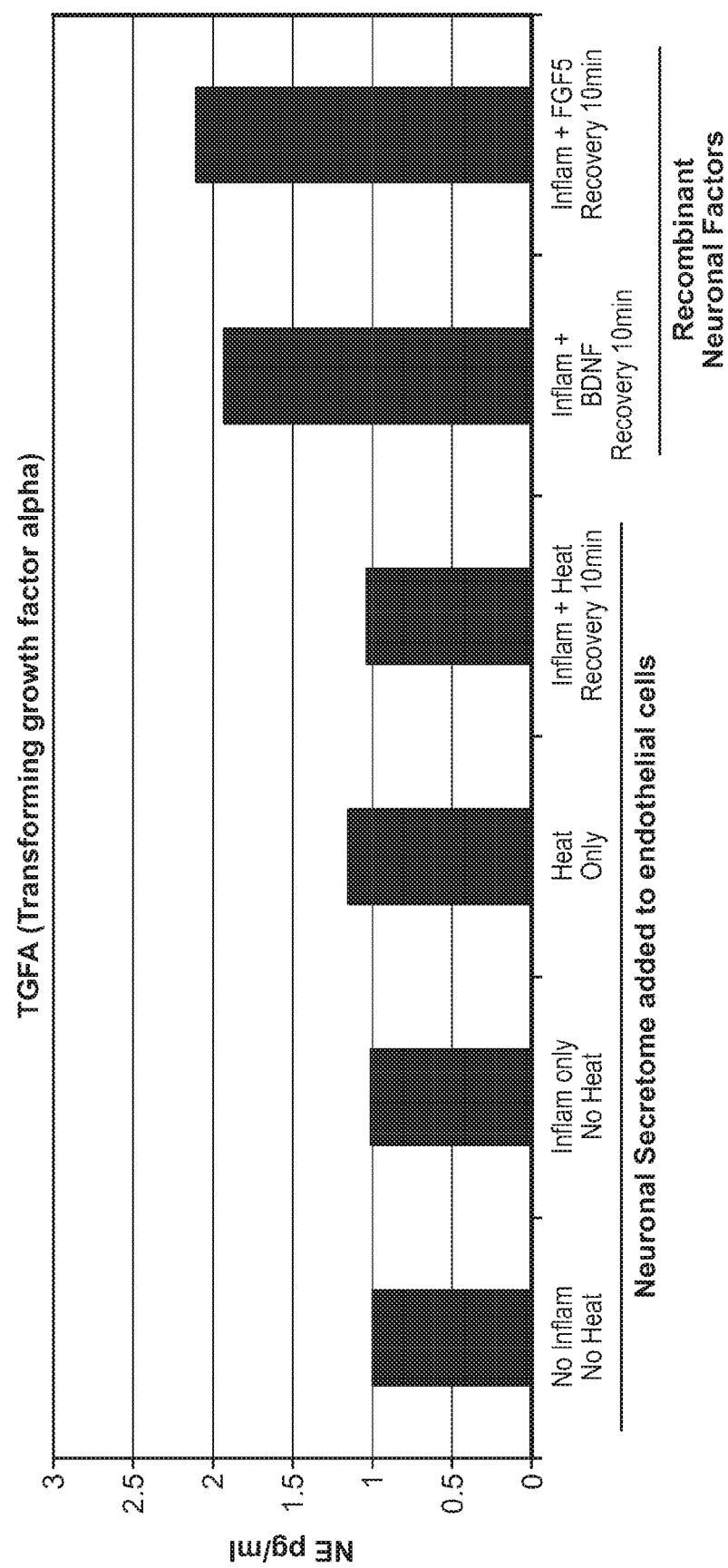
FIG. 41: Upregulation of TGFA expression in response to heat and/or inflammation and with added neuronal (recombinant) factors BDNF or FGF5.

A second set of gene profiling and secretomics experiments were performed according to the protocol set forth in FIG. 30. In the second set of experiments, neuronal LUHMES cells were treated with either heat and inflammatory conditions or recombinant stress factors such as BDNF or FGF5, then lysed and subjected to gene profiling. Conditions media was collected from LUHMES cells treated with heat and inflammatory conditions, and endothelial HCAEC were treated with either this conditioned media or recombinant neuronal stress factors such as BDNF or FGF5 for ten minutes. The endothelial cells were then lysed and subjected to gene profiling. Gene profiling of the treated LUHMES and HCAEC cells resulted in the identification of the 20 target biomarkers listed in Table 7. Results for specific proteins in this list are set forth at FIGS. 31-41.

TABLE 7

| Protein | Gene | Function/Description |
|---|---|---|
| Synuclein, alpha (FIG. 31) | SNCA | May be involved in regulation of dopamine release and transport, induces fibrillization of microtubule-associated protein tau, reduces neuronal responsiveness to various apoptotic stimuli |
| BDNF (FIG. 32) | BDNF | Promotes survival and differentiation of selected neuronal populations of the peripheral and central nervous system, participates in axonal growth and pathfinding and in modulation of dendritic growth and morphology |
| Ciliary neurotrophic factor | CNTF | Survival factor for various neuronal cell types, seems to prevent degeneration of motor axons |
| Fibroblast growth factor 2 (basic) (FIG. 33) | FGF2 | Plays important role in regulation of cell survival, cell division, angiogenesis, cell differentiation, and cell migration, functions as potent mitogen in vitro |
| Glial cell-derived neurotrophic factor 1 | GDNF | Neurotrophic factor that enhances survival and morphological differentiation of dopaminergic neurons and increases their high-affinity dopamine uptake |
| Beta-nerve growth factor 2 | NGF | Important for development and maintenance of sympathetic and sensory nervous systems, involved in differentiation and survival of neurons and in the control of gene expression for enzymes involved in neurotransmitter synthesis |
| Neurotrophin-3 | NTF3 | Neurotrophic growth factor, controls neuron survival and differentiation, seems to promote survival of visceral and proprioceptive sensory neurons |
| PF4 | Secreted | Released during platelet aggregation, neutralizes anticoagulant effect of heparin by binding more strongly to heparin than to the chondroitin-4-sulfate chains of the carrier molecule, chemotactic for neutrophils and monocytes, inhibits endothelial cell proliferation, short form is a more potent inhibitor than longer form |
| EDN2 | Secreted | Highly potent vasoconstrictive peptides, localized to non-vascular structures including epithelial cells, glia and neurons, principle physiological role is maintenance of vascular tone, have co-mitogenic activity and potentiate effects of other growth factors |
| ACE2 | Secreted | Carboxypeptidase that converts angiotensin II to angiotensin 1-7, vasodilator |
| Interferon gamma (IFN-γ) | | Member of type II interferon family, soluble cytokine with antiviral, immunoregulatory, and anti-tumor properties, potent activator of macrophages |
| Artemin (ARTN) (FIG. 34) | Secreted | Ligand for GFR-alpha-3-RET receptor complex, can also activate GFR-alpha-1-RET receptor complex, supports survival of sensory and sympathetic peripheral neurons in culture, supports survival of dopaminergic neurons of the ventral mid-brain |
| LIF | Secreted | Pleiotropic cytokine involved in nephrogenesis & ECM repair |
| Cerebellin 1 precursor (CBLN1) (FIG. 35) | Secreted | Neuromodulator, directly stimulates NE release via adenylate cyclase/PKA-dependent signaling pathway, indirectly enhances adrenocortical secretion in vivo via paracrine mechanism involving medullary catecholamine release |
| Neuregulin 1 (NRG1) (FIG. 36) | Secreted | Originally identified as 44-kD glycoprotein that interacts with NEU/ERBB2 receptor tyrosine kinase to increase phosphorylation on tyrosine residues, acts as signaling protein that mediates cell-cell interactions, plays critical roles in growth and development of multiple organ systems |
| Neuregulin 2 (NRG2) (FIG. 37) | Secreted | Member of neuregulin family |
| Neuregulin 4 (NRG4) (FIG. 38) | Secreted | Member of neuregulin family |
| Persephin (PSPN) (FIG. 39) | Secreted | Exhibits neurotrophic activity on mesencephalic dopaminergic and motor neurons |
| NTF4 (FIG. 40) | Secreted | Target-derived survival factor for peripheral sensory sympathetic neurons |
| Transforming growth factor alpha (TGFA) (FIG. 41) | Secreted | Mitogenic polypeptide able to bind EGF receptor/EGFR and act synergistically with TGF beta to promote anchorage-independent cell proliferation |

Example 3

In Vivo Target Biomarker Screening (Porcine Renal Arterial, Renal Venous, and Systemic Blood)

Proteomics detection studies are conducted using porcine blood collected from the renal artery to screen for protein and non-protein candidate target biomarkers that exhibit a change in secretion level at various time points after renal denervation/ablation.

Animals are broken into three groups of three animals each: naïve (no treatment), sham (catheterized but not ablated), and treated (subject to ablation at 65° C. and 90 seconds using a spiral ablation catheter device). Blood is collected using a multi-lumen OTW catheter designed to collect localized blood samples in the left or right renal artery (see U.S. Provisional Appl. No. 61/608,626 (C00002431.USP2)). Denervation is carried out using either a Symplicity™ catheter or an alternate catheter as described in U.S. patent application Ser. No. 13/281,361.

For renal artery blood collection, percutaneous vascular access is obtained through the right or left femoral artery and an introducer sheath is placed. Using fluoroscopic guidance, an appropriately sized angiographic catheter is inserted through the introducer sheath and advanced to each renal artery. One or more angiograms are performed for measurements of treated vessels.

Figure 42:
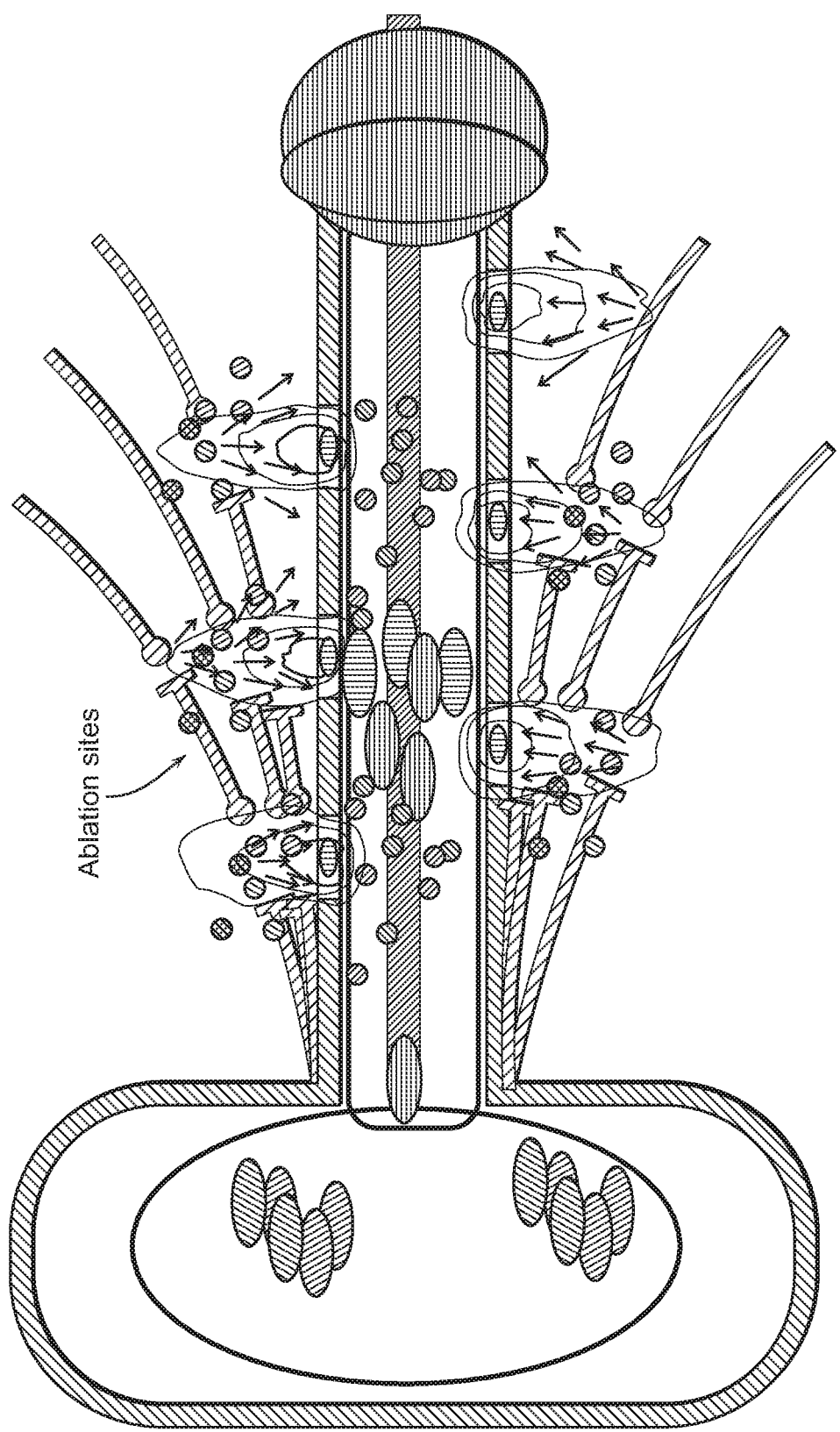
FIG. 42: Blood collection catheter for real-time assessment of post-procedural biomarkers.
Figure 43A:
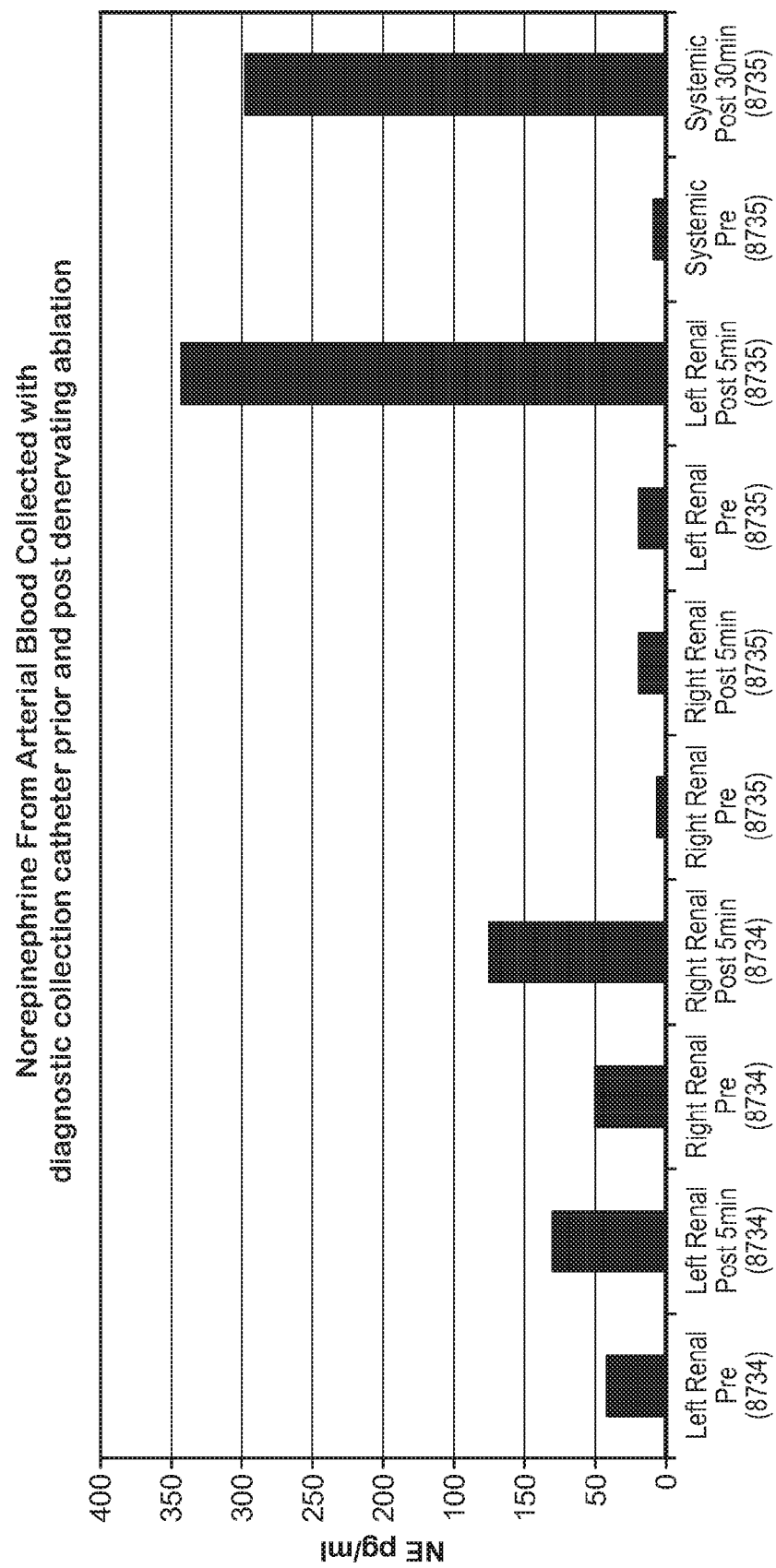
FIG. 43: A. NE levels in renal arterial blood prior to and after denervating ablation. B. Increase in NE levels in renal arterial blood versus control prior to and after denervating ablation.
Figure 43B:
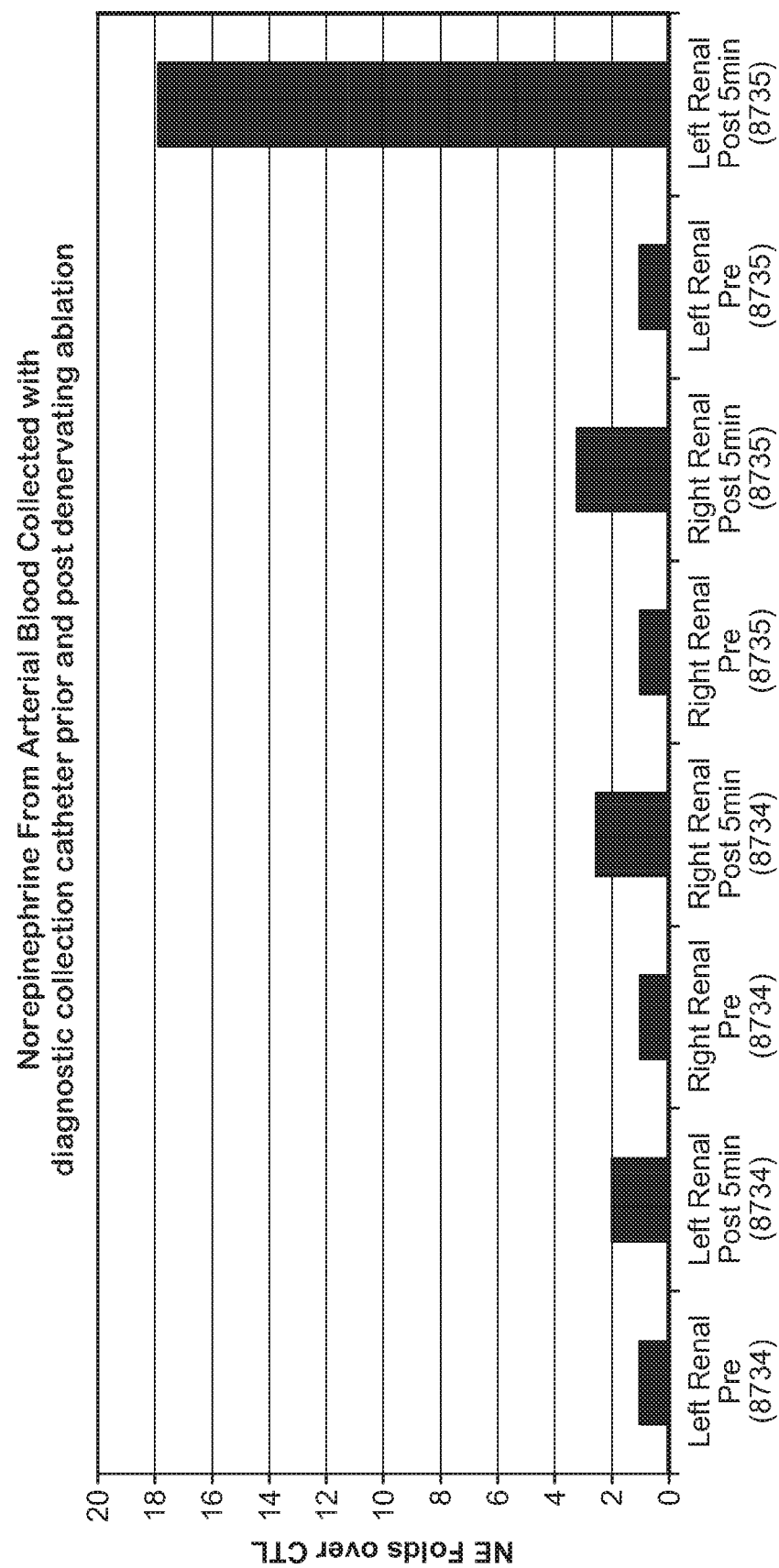
Figure 44:
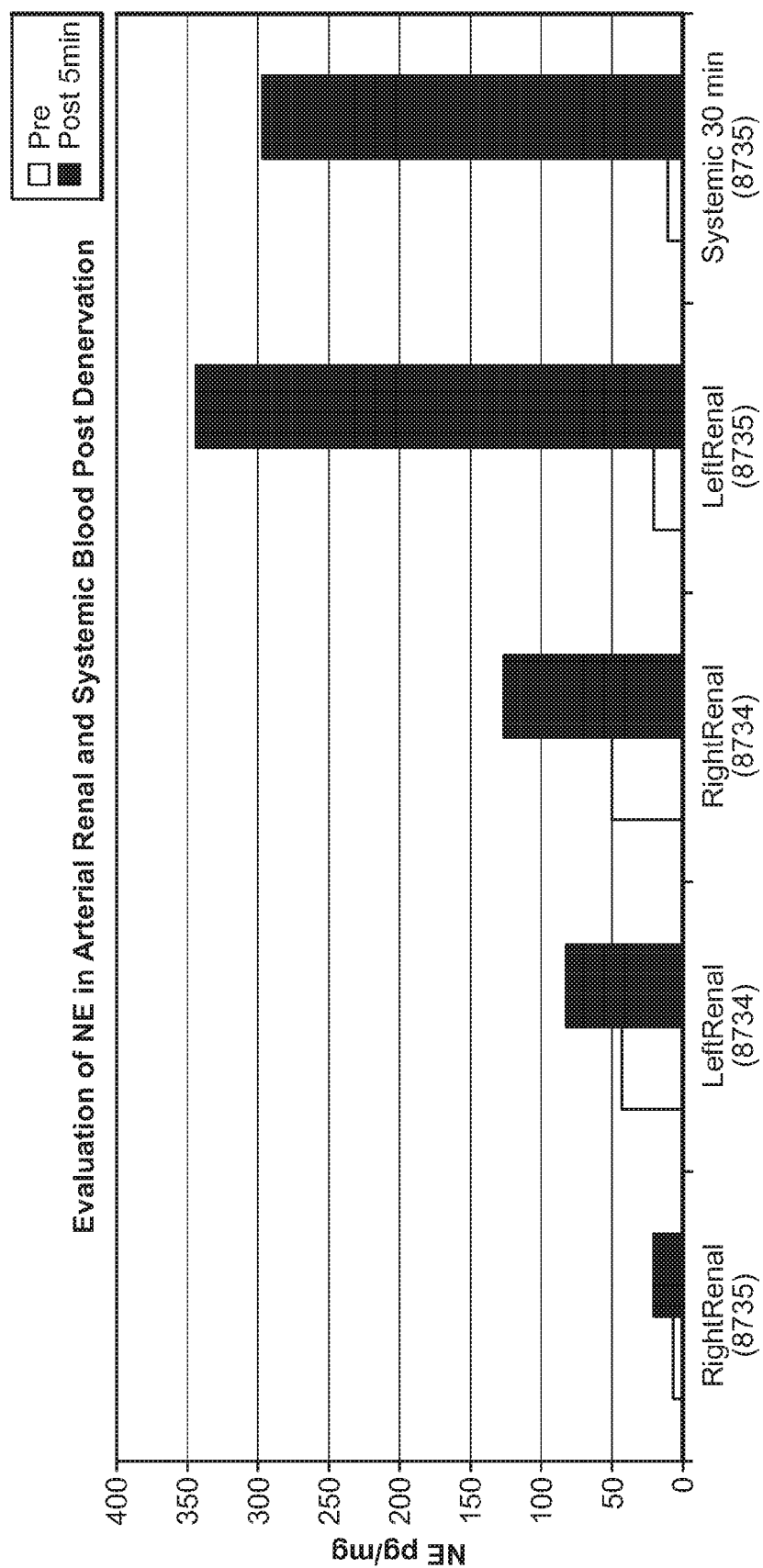
FIG. 44: NE levels in porcine renal arterial and systemic blood prior to and after denervating ablation.
Figure 45:
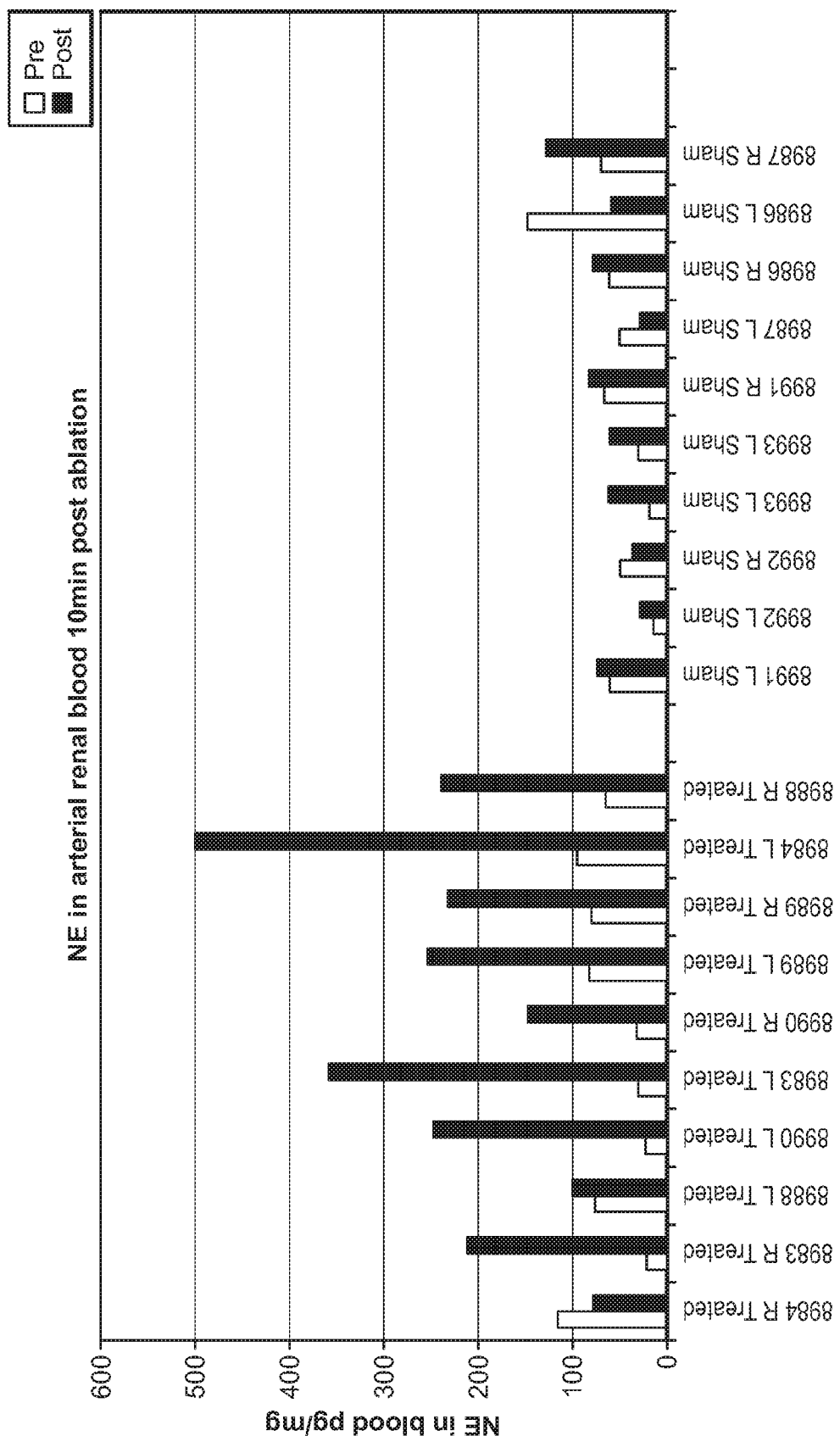
FIG. 45: NE levels in porcine renal arterial blood prior to and 10 minutes after denervating ablation.
Figure 46A:
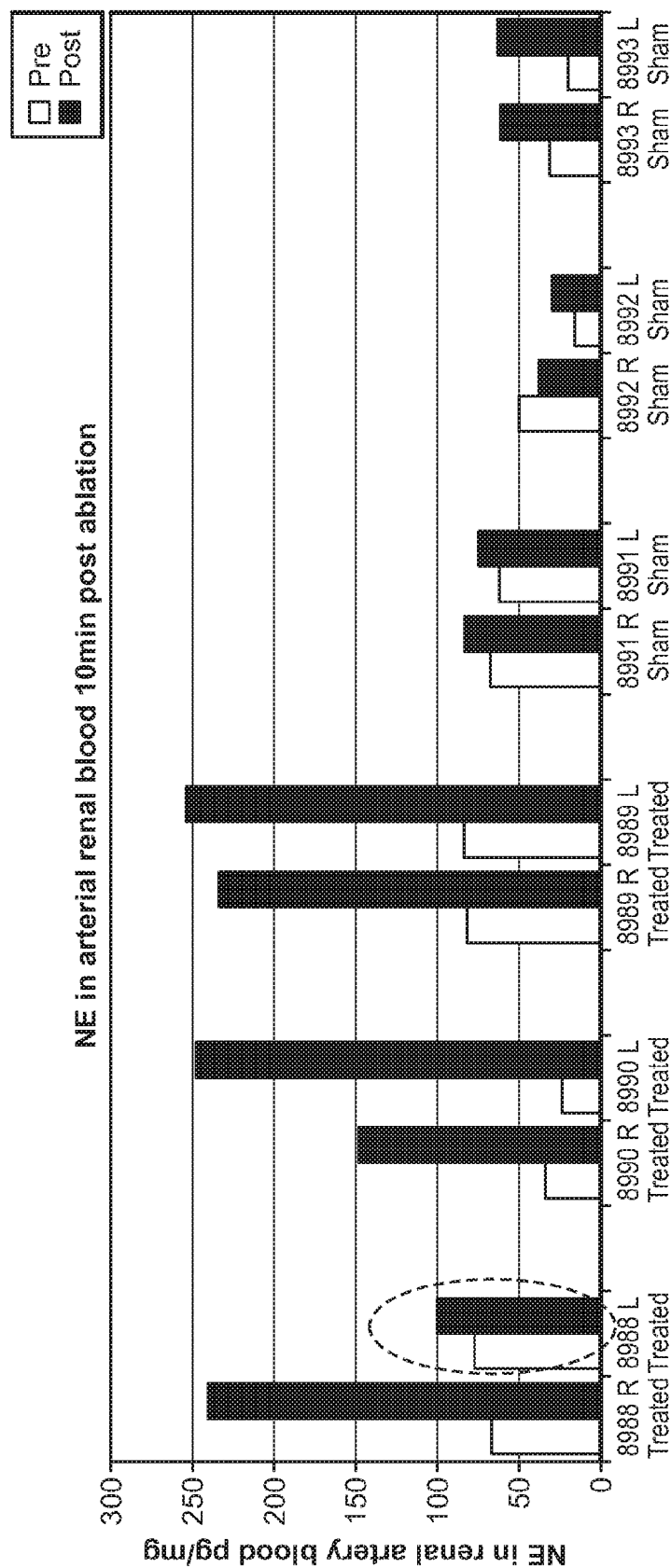
FIG. 46: A. NE levels in porcine renal arterial blood prior to and 10 minutes after denervating ablation. B. Kidney NE levels 14 days after denervating ablation.
Figure 46B:
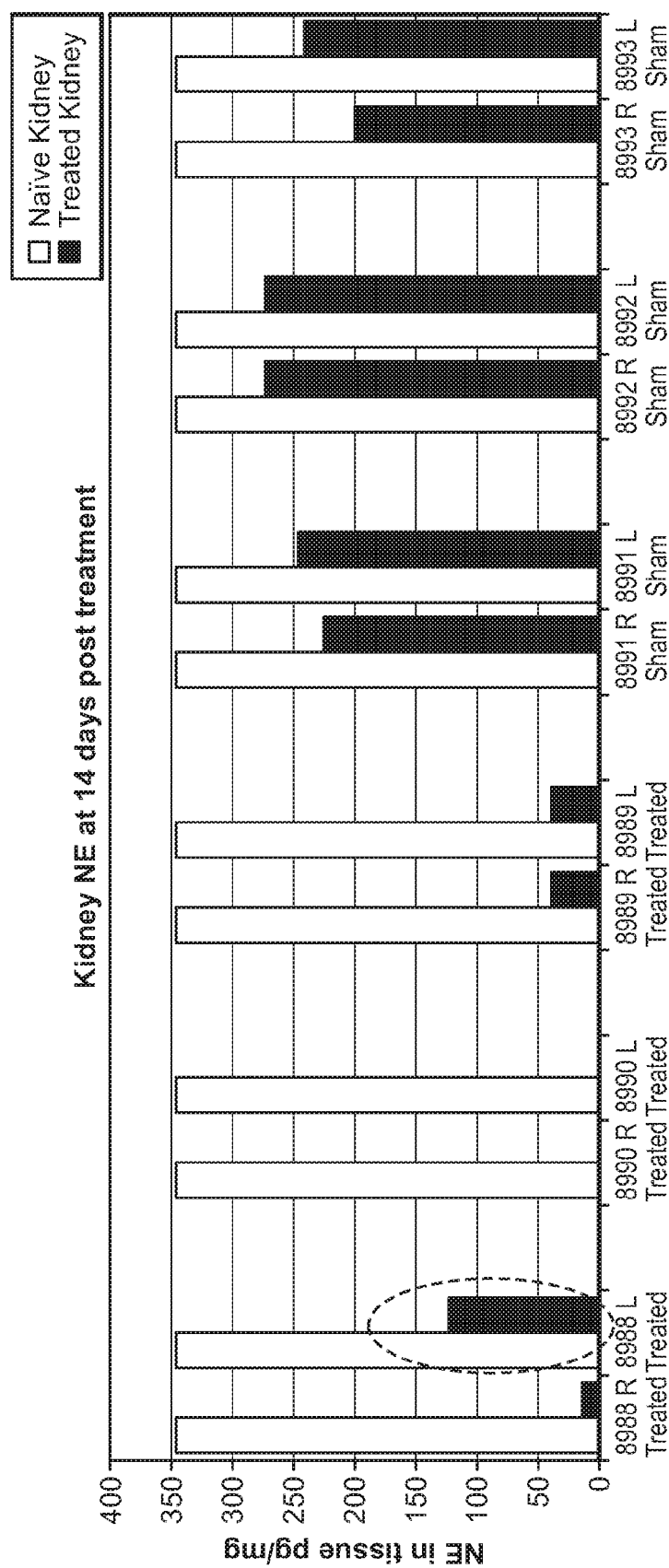
Figures 47A, 47B, 47C:
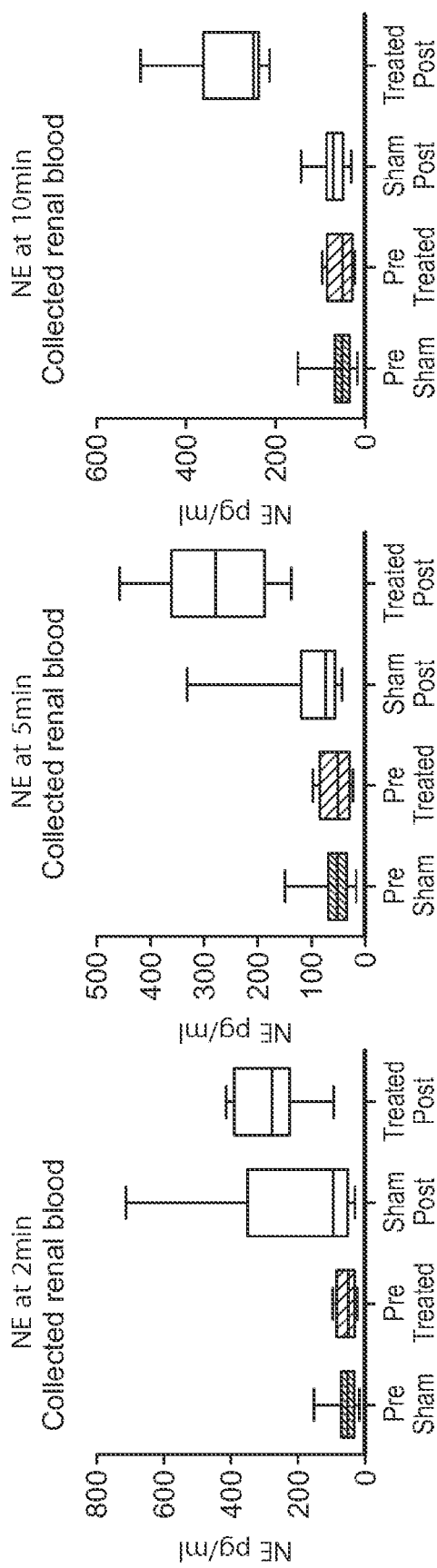
FIG. 47: A. NE levels in porcine renal blood at 2 minutes after denervating ablation. B. NE levels in porcine renal blood at 5 minutes after denervating ablation. C. NE levels in porcine renal blood at 10 minutes after denervating ablation
Figure 48A:
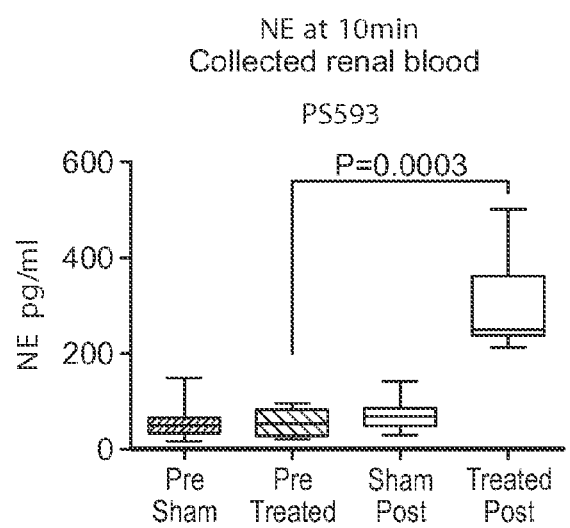
FIG. 48: A. NE levels in porcine arterial renal blood at 10 minutes. B. Corresponding kidney NE levels 14 days after denervating ablation.
Figure 48B:
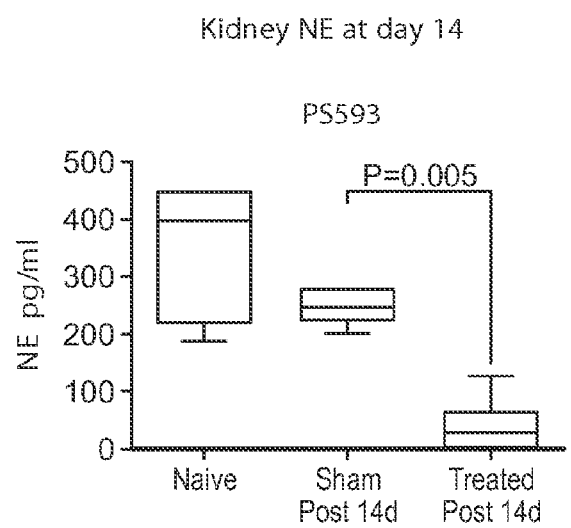
Figure 49:
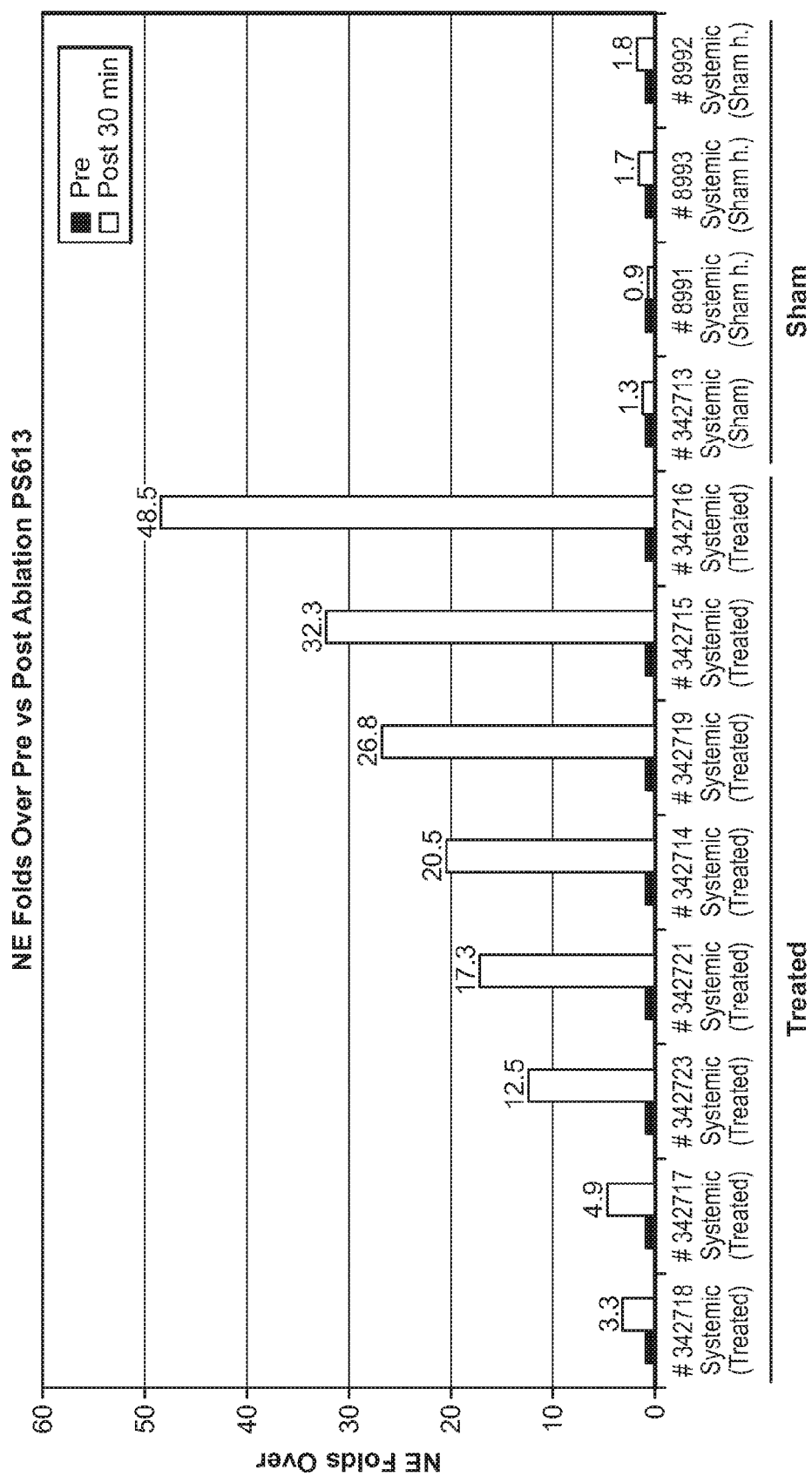
FIG. 49: Increase in NE levels after denervating ablation.

Renal arterial blood samples are collected immediately following treatment with the RF catheter and at approximately 2, 5, and 10 minutes post-ablation using a specialized collection catheter that allows for concentration of secreted factors and collection of back flow (FIG. 42). In addition, systemic arterial blood samples are collected pre-ablation and at approximately 30±5 and 60±5 minutes post-ablation. Treatment arms are summarized in Table 8.

TABLE 8

| Survival cohort | Arm | Catheter type | Minimum vessels required | Minimum number of animals |
|---|---|---|---|---|
| 0 days (acute) | 1 | Symplicity treatment (4-6 ablations) | 6 | 3 |
| | 2 | Sham (0 ablations) | 6 | 3 |
| 14 days | 3 | Symplicity treatment (4-6 ablations) | 6 | 3 |
| | 4 | Sham (0 ablations) | 6 | 3 |
| | 5 (Naïve) | N/A | 6 | 3 |
| Totals | | | 30 | 15 |

Figure 50:
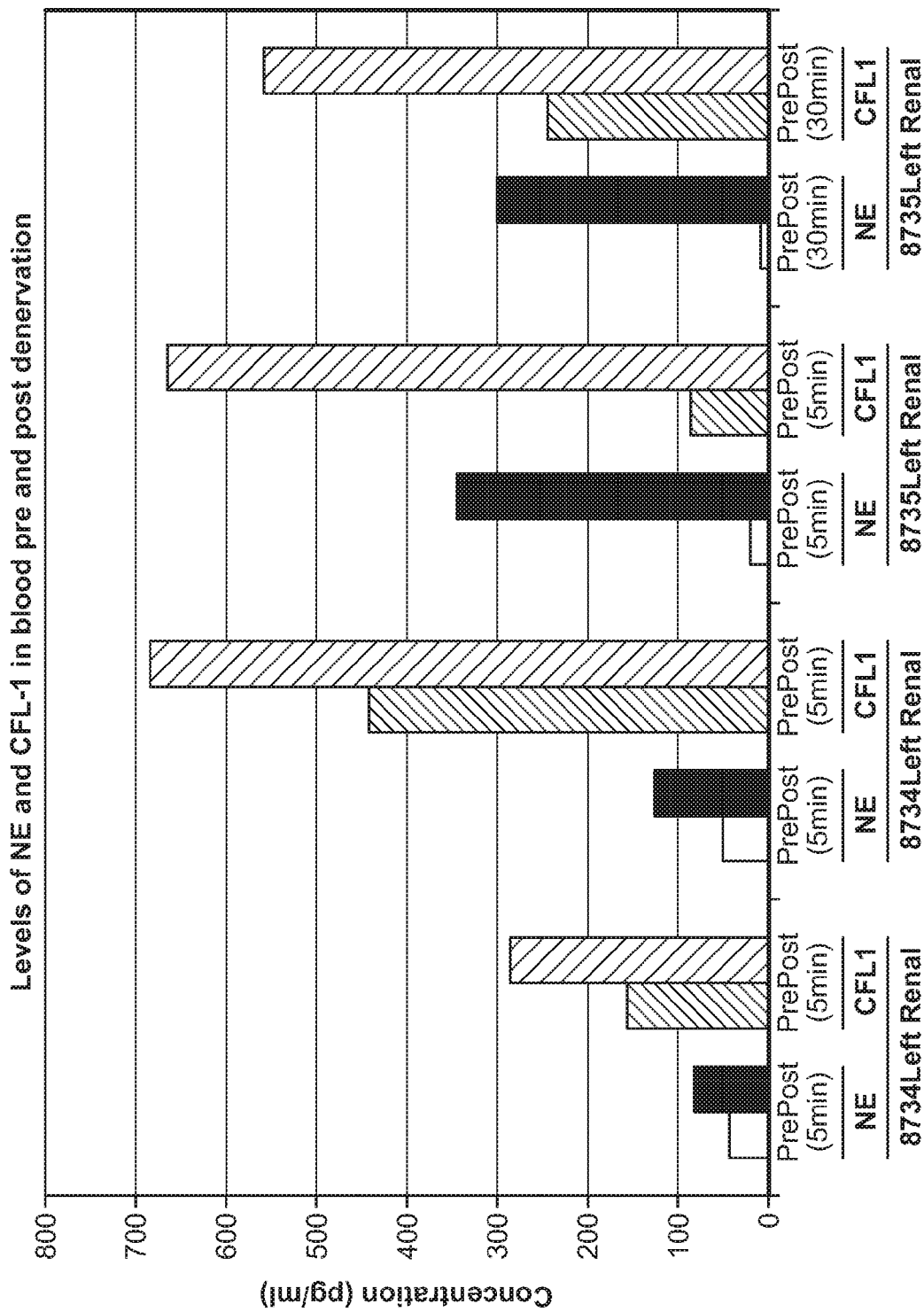
FIG. 50: Changes in NE and CFL-1 levels after denervating ablation.

An initial evaluation was carried out using NE and CFL1, with protein levels being assessed by ELISA. Results for NE are set forth in FIGS. 43-49. Results for CFL1 are set forth in FIG. 50.

This screening method may be used to evaluate one or more of the candidate target biomarkers set forth in Tables 1-7. Additional candidate biomarkers that may be evaluated include factors released in the kidney from stressed/denervated nerve ends such as neurotransmitters stored at the nerve ends (e.g., NPY), enzymes stored in nerve ends (e.g., DBH), ions released upon denervation (e.g., $Ca^{2+}$), and factors released from renal artery endothelial cells and the kidney that may play a physiological role in response to stress or modulation of renal sympathetic system (e.g., Endothelin 1, 2, and 3). Examples of these additional potential candidate target biomarkers are set forth in Table 9. Additional screens may be carried out using other porcine biological samples such as urine.

TABLE 9

| Factors released in the kidney as a result of denervation | Function |
|---|---|
| Norepinephrine/ noradrenaline (NE) | Catecholamine with multiple roles including as a hormone and a neurotransmitter. NE is converted into epinephrine by the enzyme phenylethanolamine N-methyltransferase (PNMT), with S-adenosyl-L-methionine (SAMe) as the cofactor. Areas of the body that produce or are affected by norepinephrine are described as noradrenergic. One of the most important functions of norepinephrine is its role as the neurotransmitter released from the sympathetic neurons. 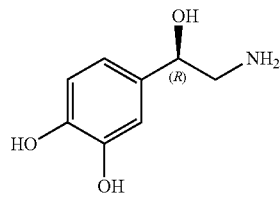 |
| Neuropeptide Y (NPY) | 36-amino acid peptide neurotransmitter found in the brain and autonomic nervous system, augments the vasocontrictor effects of noradrenergic neurons. |
| Dopamine (DBN) | Converted into NE by dopamine β-hydroxylase (DBH), with $O^2$ and L-ascorbic acid as cofactors. |
| $Ca^{2+}$ | Mediates nerve signaling and regeneration and could be released upon denervation |
| Renin | Highly specific endopeptidase, functions to generate angiotensin I from angiotensinogen in plasma, initiating a cascade of reactions that produce an elevation of blood pressure and increased sodium retention by the kidney. |
| Dopamine beta-hydroxylase (DBH) | Oxidoreductase belonging to the copper type II ascorbate-dependent monooxygenase family, present in synaptic vesicles of postganglionic sympathetic neurons, converts dopamine to norepinephrine. Protein exists in both soluble and membrane-bound forms. |
| Angiotensin (AGT) | Acts directly on vascular smooth muscle as a potent vasoconstrictor, affects cardiac contracility and heart rate through its action on the sympathetic nervous system, alters renal sodium and water absorption through its ability to stimulate the zona glomerulosa cells of the adrenal cortex to synthesize and secrete aldosterone. |
| Endothelin 1, Endothelin 2, Endothelin 3 | Endothelium-derived vasoactive peptides involved in a variety of biological functions. Active form is a 21 amino acid peptide processed from the precursor protein. Active peptide is a ligand for EDNRB, and this interaction is essential for development of neural crest-derived cell ineages, such as melanocytes and enteric neurons. Endothelin receptors are widely expressed in all tissues, consistent with their physiological role as vasoactive peptides. Also localized to non-vascular structures including epithelial cells, glia and neurons. Principle physiological role of endothelin receptors is maintenance of vascular tone. |
| Neurotensin (NTS) | 170 AA protein, may play endocrine or paracrine role in regulation of fat metabolism, causes contraction of smooth muscle. |
| Amyloid beta (A4) precursor protein (APP) | 770 AA protein, N-APP binds TNFRSF21, triggering caspase activation degeneration of both neuronal cell bodies (via caspase-3) and axons (via caspase-6). |

Selected Embodiments of Renal Neuromodulation Systems and Devices

Figure 51:
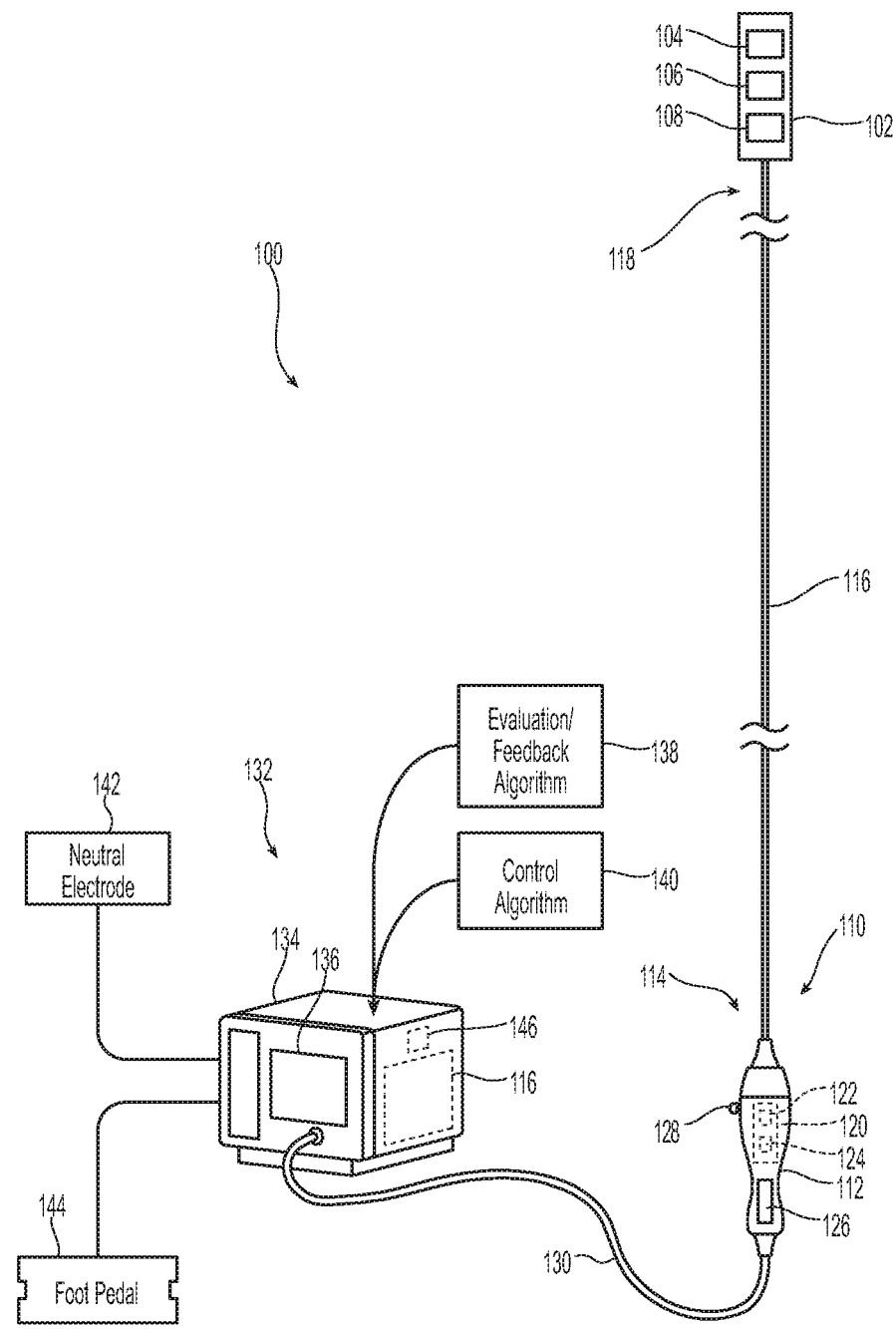
FIG. 51: Partially-schematic perspective view illustrating a renal neuromodulation system including a treatment device configured in accordance with an embodiment of the present technology.

FIG. 51 is a partially-schematic diagram illustrating a system 100 configured in accordance with an embodiment of the present technology. The system 100 can include a treatment device 110 (e.g., a catheter) operably coupled to a console (e.g., an energy generator) 132 via a connector 130 (e.g., a cable). As shown in FIG. 51, the treatment device 110 can include an elongated shaft 116 having a proximal portion 114, a handle assembly 112 at a proximal region of the proximal portion 114, and a distal portion 118 extending distally relative to the proximal portion 114. The elongated shaft 116 can be configured to locate the distal portion 118 intravascularly (e.g., within a renal artery) or within another suitable body lumen (e.g., within a ureter) at a treatment location. The treatment device 110 can further include a neuromodulation and sampling assembly 102 carried by or affixed to the distal portion 118 of the elongated shaft 116. The neuromodulation and sampling assembly 102 can include one or more energy delivery elements 104 (shown schematically in FIG. 51) (e.g., electrodes) configured to modulate nerves at or near the treatment location as well as one or more sampling ports 108 (also shown schematically in FIG. 51) configured to collect biological samples from the treatment location or another suitable location near the treatment location.

The system 100 can further include an analyzer 120 (e.g., a biosensor) configured to receive and analyze the biological sample collected by the neuromodulation and sampling assembly 102 for the level or activity of one or more target biomarkers. In certain embodiments, the analyzer may be configured to further analyze one or more additional biological parameters related to neuromodulation.

Upon receipt of the sample by the analyzer 120, detection and/or capture agents within the analyzer 120 can interact with target biomarkers of the collected sample, if present. In at least some cases, binding of a target biomarker to a capture agent and/or interaction of the target biomarker with a detection agent can result in a biomarker response (e.g., a change in color, formation of a reaction product, or another suitable response). The physicochemical transducer 122 can transform the biomarker response into a more easily measureable and quantifiable signal (e.g., a colorimetric, fluorescent, heat, energy, or electric signal) that can be sensed by or communicated to the processing device 124 for storage and/or analysis. The processing device 124 can be operably coupled to an indicator 126 carried by the handle 112. The indicator 126 can be configured to indicate suitable information related to processing the target biomarker (e.g., a sample date, a status of the target biomarker, and/or a status of nerve modulation based on a detected level or activity of the target biomarker). The indication can be auditory and/or visual. In some embodiments, the indicator 126 includes a suitable display component, such as a light emitting diode, an imaging display, and/or a graphical user interface.

In some embodiments, the analyzer 120 is integrated into the console 132 instead of the handle 112. In these embodiments, for example, the analyzer 120 can be configured to receive a biological sample directly from the treatment device 110 (e.g., via a fluid conduit (not shown) (e.g., polymer tubing) within or separate from the connector 130). The fluid conduit can extend between the treatment device 110 and the console 132 where an air or fluid pump (not shown) integrated with the analyzer 120 can draw a biological sample into a portion of the analyzer 120. Alternatively, the air or fluid pump can be housed in the handle 112 to transfer a biological sample to the analyzer 120 contained within the console. In these and other embodiments, the handle 112 can include a removable container (not shown) configured to receive a biological sample collected via the sampling port 108 and conveyed to the container via the shaft 116. For detection and/or analysis of a target biomarker within the sample, the removable container can be removed from the handle 112 and transferred to the analyzer 120 (e.g., when the analyzer 120 is a remote a standalone device or when the analyzer 120 integrated into the console 132, and/or in other embodiments in which the analyzer 120 is remote relative to the treatment device 110). The removable container may be reusable or disposable.

The console 132 can be configured to generate a selected form and/or magnitude of energy for delivery to the treatment site via the energy delivery element 104 of the neuromodulation and sampling assembly 102. For example, the console 132 can include an energy generator (not shown) configured to generate RF energy (monopolar or bipolar), pulsed RF energy, microwave energy, optical energy, ultrasound energy (e.g., intravascularly delivered ultrasound, extracorporeal ultrasound, high-intensity focused ultrasound (HIFU)), cryotherapeutic energy, direct heat energy, chemicals (e.g., drugs or other agents), radiation (e.g., infrared, visible, gamma), or another suitable type of energy. In some embodiments, neuromodulation may be achieved by chemical-based treatment including delivering one or more chemicals (e.g., guanethidine, ethanol, phenol, a neurotoxin (e.g., vincristine)), or another suitable agent selected to alter, damage, or disrupt nerves. In a particular embodiment, the console 132 includes a RF generator operably coupled to one or more energy delivery elements 104 of the neuromodulation and sampling assembly 102. Furthermore, the console 132 can be configured to control, monitor, supply, or otherwise support operation of the treatment device 110. For example, a control mechanism, such as foot pedal 144, may be connected (e.g., pneumatically connected or electrically connected) to the console 132 to allow an operator to initiate, terminate and/or adjust various operational characteristics of the energy generator, such as power delivery. In some embodiments, the console 132 may be configured to provide delivery of a monopolar electric field via the energy delivery element 104. In such embodiments, a neutral or dispersive electrode 142 may be electrically connected to the console 132 and attached to the exterior of the patient (not shown).

In some embodiments, the system 100 includes a remote control device (not shown) that can be configured to be sterilized to facilitate its use within a sterile field. The remote control device can be configured to control operation of the neuromodulation and sampling assembly 102, the console 132, and/or other suitable components of the system 100. For example, the remote control device can be configured to allow for selective activation of the neuromodulation and sampling assembly 102. In other embodiments, the remote control device may be omitted and its functionality may be incorporated into the handle 112 or console 132.

As shown in FIG. 51, the console 132 can include a primary housing 134 having a display 136. In some embodiments, the console 132 includes a processing device 146 having processing circuitry (e.g., a microprocessor). The console 132 can be configured to execute an automated control algorithm 140 and/or to receive control instructions from an operator. Furthermore, the console 132 can be configured to provide feedback to an operator before, during, and/or after a treatment procedure via the display 136 and/or via an evaluation/feedback algorithm 138. For example, the feedback can be based on output from the analyzer 120. The processing device 146 can be configured to execute stored instructions relating to the control algorithm 140 and/or the evaluation/feedback algorithm 138.

The console 132 can be configured to communicate with the treatment device 110 (e.g., via the connector 130). For example, the neuromodulation and sampling assembly 102 and/or the shaft 116 can include a sensor 106 (e.g., a chemical sensor, a temperature sensor, a pressure sensor, or a flow rate sensor) and a sensor lead (not shown) (e.g., an electrical lead or a pressure lead) configured to carry a signal from the sensor 106 to the handle 112. The connector 130 can be configured to carry the signal from the handle 112 to the console 132. The processing device 146 of the console 132 can be configured to communicate with the processing device 124 of the analyzer 120 (e.g., via the connector 130, Bluetooth, wireless, or in another suitable manner when the analyzer 120 is within the handle 112 or otherwise remote relative to the console 132).

In some embodiments, the console 132 includes a vacuum 148 or other suitable negative pressure source (e.g., a syringe) operably coupled to the sampling port 108 of the neuromodulation and sampling assembly 102. In other embodiments, the vacuum 148 can be a standalone device separate from the console 132. The vacuum 148 can be in fluid connection with the sampling port 108 via the shaft 116. Negative pressure generated by the vacuum 148 can be used, for example, to draw a biological sample into the sampling port 108. In yet other embodiments, the treatment device 110 can include an adapter (not shown) (e.g., a luer lock) configured to be operably coupled to a syringe (not shown) and the syringe can be used to apply negative pressure to the shaft 116.

FIG. 52A is a side view illustrating the neuromodulation and sampling assembly 102 in a low-profile or delivery state in accordance with an embodiment of the present technology. The neuromodulation and sampling assembly 102 can include a neuromodulation element 200, a sampling element 202, and an occlusion element 204. In some embodiments, the neuromodulation element 200 and the sampling element 202 are distal to the occlusion element 204 and the neuromodulation element 200 is distal to the sampling element 202. In other embodiments, the neuromodulation element 200 and the sampling element 202 are distal to the occlusion element 204 and the sampling element 202 is distal to the neuromodulation element 200. In still other embodiments, the neuromodulation element 200, the sampling element 202, and the occlusion element 204 can have another suitable arrangement. A proximal region 208 of the neuromodulation and sampling assembly 102 can be carried by or affixed to the distal portion 118 of the elongated shaft 116. For example, all or a portion (e.g., a proximal portion) of the neuromodulation and sampling assembly 102 can be an integral extension of the shaft 116. In some embodiments, the profile of the neuromodulation and sampling assembly can increase between the neuromodulation element 200 and the sampling element 202. A distal region 206 of the neuromodulation and sampling assembly 102 may terminate distally with, for example, an atraumatic, flexible curved tip 214 having an opening 212 at its distal end. In some embodiments, the distal region 206 of the neuromodulation and sampling assembly 102 may also be configured to engage another element of the system 100 or treatment device 110.

FIG. 52B is an enlarged view of a portion of the neuromodulation and sampling assembly 102 of FIG. 52A. FIG. 53 is a cross-sectional end view taken along line 3-3 in FIG. 52A. Referring to FIGS. 52A-53 together, the neuromodulation and sampling assembly 102 can include the one or more energy delivery elements 104 (e.g., RF electrodes, ultrasound transducers, cryotherapeutic cooling assemblies, etc.) carried by a support structure 210 as part of the neuromodulation element 200. The energy delivery elements 104, for example, can be separate band electrodes axially spaced apart along the support structure 210 (e.g., adhesively bonded to the support structure 210 at different positions along the length of the support structure 210). In other embodiments, the neuromodulation and sampling assembly 102 may have a single energy delivery element 104 at or near the distal portion 118 of the shaft 116.

In some embodiments, the energy delivery elements 104 are formed from a suitable electrically conductive material (e.g., a metal, such as gold, platinum, alloys of platinum and iridium, etc.). The number, arrangement, shape (e.g., spiral and/or coil electrodes) and/or composition of the energy delivery elements 104 may vary. The individual energy delivery elements 104 can be electrically connected to the console 132 by a conductor or bifilar wire 300 extending through a lumen 302 of the shaft 116 and/or support structure 210. For example, the individual energy delivery elements 104 may be welded or otherwise electrically coupled to corresponding energy supply wires 300, and the wires 300 can extend through the elongated shaft 116 for the entire length of the shaft 116 such that proximal ends of the wires 300 are coupled to the handle 112 and/or to the console 132.

As shown in the enlarged cut-away view of FIG. 52B, the support structure 210 can be a tube (e.g., a flexible tube) and the neuromodulation and sampling assembly 102 can include a pre-shaped control member 220 positioned within the tube. Upon deployment, the control member 220 can bias at least a portion of the neuromodulation and sampling assembly 102 (e.g., the neuromodulation element 200) into a deployed state (FIG. 56C or 56D). For example, the control member 220 can have a pre-set configuration that gives at least a portion of the neuromodulation and sampling assembly 102 a helical or spiral configuration in the deployed state (FIG. 56C or 56D). In some embodiments, the control member 220 includes a tubular structure comprising a nitinol multifilar stranded wire with a lumen 222 therethrough and sold under the trademark HELICAL HOLLOW STRAND (HHS), and commercially available from Fort Wayne Metals of Fort Wayne, Ind. The lumen 222 can define a passageway for receiving a guide wire 600 that extends proximally from the opening 212 at the tip 214 of the neuromodulation and sampling assembly 102.

FIGS. 54 and 55 are cross-sectional end views taken, respectively, along lines 4-4 and 5-5 of FIG. 52A. With reference to FIGS. 52A-55 together, the neuromodulation and sampling assembly 102 can include the sampling port 108 as part of the sampling element 202. The sampling port 108 can be in fluid connection with a sampling lumen 400 that extends proximally along the shaft 116 from sampling port 108 to the handle 112. In some embodiments, the sampling lumen 400 can be coupled to the vacuum 148 or a syringe (not shown) to facilitate retrieval of a sample through the sampling port 108 and conveyance of the sample along the sampling lumen 400. To prevent the sample from contaminating the vacuum 148 or syringe, the sampling lumen 400 can include a one-way valve or seal (not shown) at a location along the length of the sampling lumen 400 distal to the negative pressure source inlet. In some embodiments, an inner cross-sectional area of the sampling lumen 400 and/or an area of the sampling port can be selected to achieve an adequate pressure drop across the sampling port 108.

The sampling element 202 can further include an occlusion member 218 (e.g., a compliant, semi-compliant, or non-compliant balloon, an expandable basket, a stent-like structure, etc.) as part of the occlusion element 204. The occlusion member 218 can be configured to at least partially occlude a vessel (e.g., a renal artery) or lumen in which the neuromodulation and sampling assembly 102 is positioned. In some embodiments, the occlusion member 218 extends around a segment of the shaft 116 that includes an inflation opening 216. For example, the occlusion member 218 can be laser-bonded or adhered by other suitable methods to an outer surface of the shaft 116 at axially spaced apart locations distal and proximal, respectively, relative to the inflation opening 216.

The inflation opening 216 can connect to an inflation lumen 500 that extends proximally along the shaft 116 from the inflation opening 216 to the handle 112. Control of the occlusion element 204 and/or occlusion member 218 (e.g., control over inflation/expansion volume, inflation/expansion timing and/or deflation/collapse timing) can be manual or automatic (e.g., based on a pre-set schedule or algorithm). As shown in FIG. 55, the sampling lumen 400 and the inflation lumen 500 can be positioned within the shaft 116 at least proximate to opposite sides of the lumen 222. In other embodiments, the sampling lumen 400 and the inflation lumen 500 can be positioned within the support structure 210. In yet other embodiments, the sampling lumen 400, the inflation lumen 500 and the lumen 222 can have other suitable shapes, sizes and/or arrangements.

Several embodiments of methods for utilizing the system 100 to provide real-time or relatively contemporaneous (e.g., less than 30 minutes) renal neuromodulation efficacy feedback in accordance with the present technology are described herein. In a particular embodiment, a method includes: (a) collecting a pre-neuromodulation biological sample at a treatment site via a sampling element 202 of a neuromodulation and sampling assembly 102; (b) determining a baseline or pre-neuromodulation level or activity of one or more target biomarkers within the pre-neuromodulation biological sample; (c) performing a neuromodulation procedure using a neuromodulation element 200 of the neuromodulation and sampling assembly 102; (d) expanding an occlusion member 218 to at least partially occlude a vessel or lumen in which the treatment site is located; (e) collecting a post-neuromodulation biological sample at the treatment site via the sampling element 202; (f) determining a post-neuromodulation level or activity for the target biomarker(s); and (g) comparing the post-neuromodulation level or activity to the baseline level or activity to provide neuromodulation efficacy feedback.

Figure 56A:
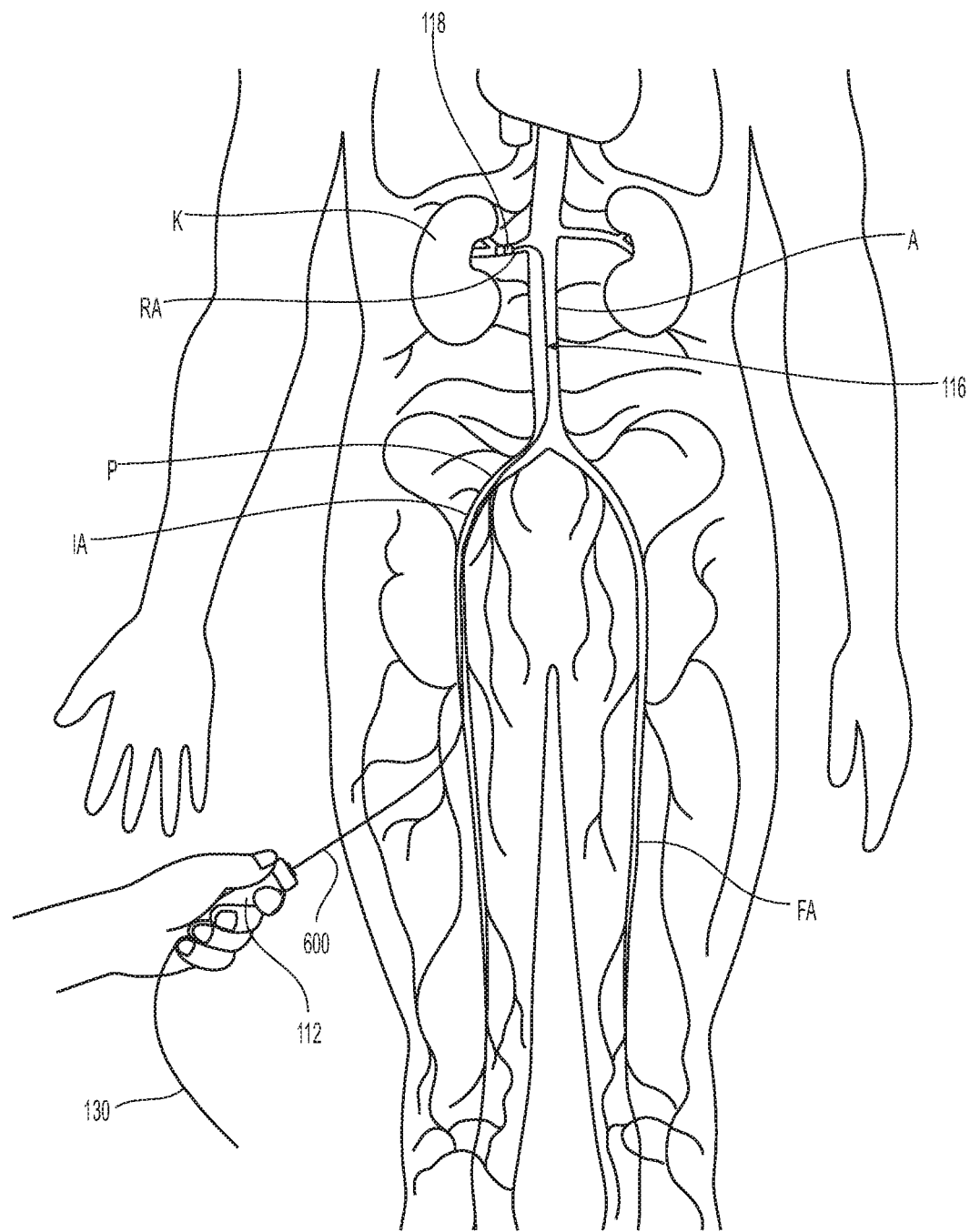
FIG. 56: A. Partially cross-sectional anatomical front view illustrating advancing the treatment device shown in FIG. 51 along an intravascular path in accordance with an embodiment of the present technology. B. Cross-sectional view of the neuromodulation and sampling assembly shown in FIG. 52A within a renal artery in accordance with an embodiment of the present technology. C. Cross-sectional view of the neuromodulation and sampling assembly shown in FIG. 52A illustrating deploying a portion of the neuromodulation and sampling assembly at a treatment location within the renal artery in accordance with an embodiment of the present technology. D. Cross-sectional view of the neuromodulation and sampling assembly of FIG. 52A illustrating occluding a portion of the renal artery at a treatment location in accordance with an embodiment of the present technology.
Figure 56B:
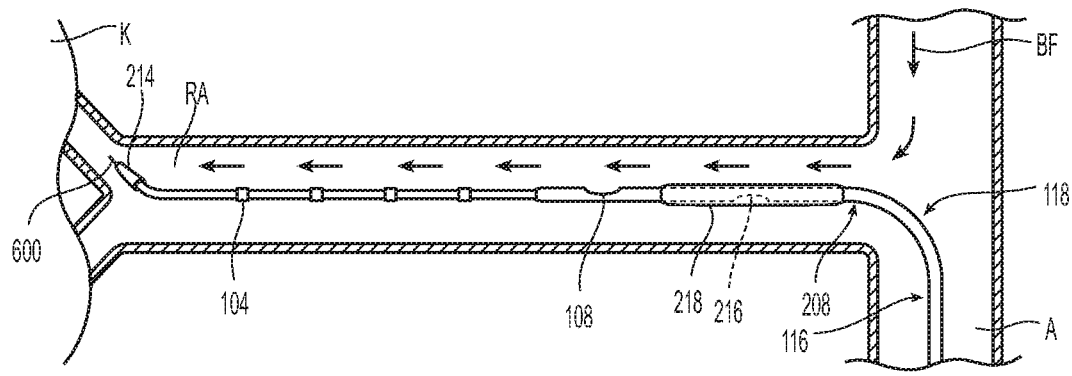
Figure 56C:
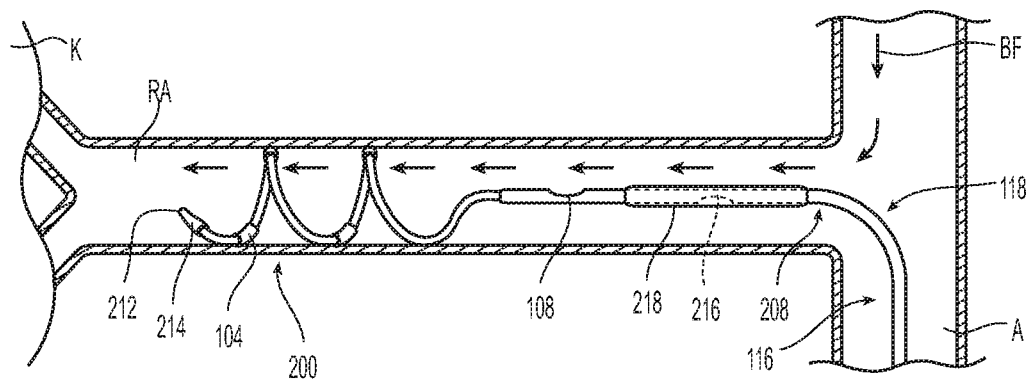
Figure 56D:
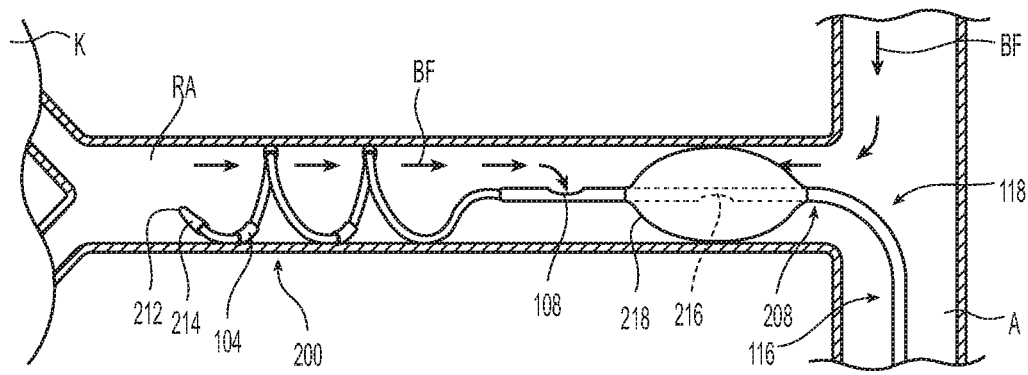

Referring to FIG. 56A, intravascular delivery of the neuromodulation and sampling assembly 102 can include percutaneously inserting a guide wire 600 within the vasculature at an access site (e.g., femoral, brachial, radial, or axillary artery) and moving the shaft 116 and the neuromodulation and sampling assembly 102 (in the delivery state) along the guide wire until at least a portion of the neuromodulation and sampling assembly 102 reaches the treatment location (as shown in FIG. 56B). In some embodiments, the shaft 116 and the neuromodulation and sampling assembly 102 can include the lumen 222 (FIGS. 53-55) configured to receive a guide wire 600 in an over-the-wire or rapid exchange configuration. As illustrated, a section of the proximal portion 114 of the shaft 116 can be extracorporeally positioned and manipulated by the operator (e.g., via the actuator 128) to advance the shaft 116 through the sometimes tortuous intravascular path (P) and remotely manipulate the distal portion 118 of the shaft 116.

Image guidance, e.g., computed tomography (CT), fluoroscopy, intravascular ultrasound (IVUS), optical coherence tomography (OCT), intracardiac echocardiography (ICE), or another suitable guidance modality, or combinations thereof, may be used to aid the clinician's positioning and manipulation of the neuromodulation and sampling assembly 102. For example, a fluoroscopy system (e.g., including a flat-panel detector, x-ray, or c-arm) can be rotated to accurately visualize and identify the target treatment site. In other embodiments, the treatment site can be located using IVUS, OCT, and/or other suitable image mapping modalities that can correlate the target treatment site with an identifiable anatomical structure (e.g., a spinal feature) and/or a radiopaque ruler (e.g., positioned under or on the patient) before delivering the treatment device 110. Further, in some embodiments, image guidance components (e.g., IVUS, OCT) may be integrated with the treatment device 110 and/or run in parallel with the treatment device 110 to provide image guidance during positioning of the neuromodulation and sampling assembly 102. For example, image guidance components (e.g., IVUS or OCT) can be coupled to a distal portion of the treatment device 110 to provide three-dimensional images of the vasculature proximate the target site to facilitate positioning or deploying the neuromodulation and sampling assembly 102 within the target renal blood vessel.

Once the neuromodulation and sampling assembly 102 is positioned at a treatment location, the guide wire 600 can be at least partially introduced (e.g., inserted) into or removed (e.g., withdrawn) from the neuromodulation and sampling assembly 102 to transform or otherwise move the neuromodulation and sampling assembly 102 to a deployed state. In the deployed state, for example, the energy delivery elements 104 of the neuromodulation and sampling assembly 102 can be positioned in stable contact with a wall of the vessel or lumen for delivering energy, as illustrated by FIG. 56C. Though the embodiment shown in FIG. 56C shows a deployed neuromodulation and sampling assembly 102 in which only the neuromodulation element 200 is spiral or helically-shaped, in other embodiments, all or a greater portion of the neuromodulation and sampling assembly 102 can be spiral or helically-shaped. Furthermore, the neuromodulation element 200, the sampling element 202, and/or other portions of the neuromodulation and sampling assembly 102 can have other suitable shapes, sizes, and/or configurations (e.g., bent, deflected, helical, spiral, zig-zag, Malecot, etc.).

In some embodiments, the neuromodulation and sampling assembly 102 may be delivered to a treatment site within a guide sheath (not shown) with or without using the guidewire 600. When the neuromodulation and sampling assembly 102 is at the target site, the guide sheath may be at least partially withdrawn or retracted and the neuromodulation and sampling assembly 102 can be transformed into the deployed state. For example, at least a portion of the neuromodulation and sampling assembly 102 can have a shape memory corresponding to a deployed state and the sheath can prevent the neuromodulation and sampling assembly 102 from deploying in response to the shape memory before reaching the treatment location. In still other embodiments, the shaft 116 may be steerable itself such that the neuromodulation and sampling assembly 102 may be delivered to the treatment site without the aid of the guide wire 600 and/or guide sheath.

Examples of other suitable neuromodulation delivery configurations, deployment configurations and/or deployment mechanisms can be found in U.S. application Ser. No. 12/910,631, filed Oct. 22, 2010, entitled "APPARATUS, SYSTEMS, AND METHODS FOR ACHIEVING INTRAVASCULAR, THERMALLY-INDUCED RENAL NEUROMODULATION," U.S. application Ser. No. 13/281,361, filed Oct. 25, 2011, entitled "CATHETER APPARATUSES HAVING MULTI-ELECTRODE ARRAYS FOR RENAL NEUROMODULATION AND ASSOCIATED SYSTEMS AND METHODS," and U.S. Provisional Application No. 61/646,218, filed May 5, 2012, entitled "MULTI-ELECTRODE CATHETER ASSEMBLIES FOR RENAL NEUROMODULATION AND ASSOCIATED SYSTEMS AND METHODS," which are all incorporated herein by reference in their entireties.

In the deployed state, at least a portion of the neuromodulation and sampling assembly 102 can be configured to contact an inner wall of the renal artery and to cause a fully-circumferential lesion without the need for repositioning. For example, the neuromodulation element 200 can be configured to form a lesion or series of lesions (e.g., a helical/spiral lesion or a discontinuous lesion) that is fully-circumferential overall, but generally non-circumferential at longitudinal segments of the treatment location. This can facilitate precise and efficient treatment with a low possibility of vessel stenosis. In other embodiments, the neuromodulation element 200 can be configured to form a partially-circumferential lesion or a fully-circumferential lesion at a single longitudinal segment of the treatment location. In some embodiments, the therapeutic element 502 can be configured to cause therapeutically-effective neuromodulation (e.g., using ultrasound energy) without contacting a vessel wall.

At one or more timepoints prior to neuromodulation, the sampling element 202 of the assembly 102 can collect a pre-neuromodulation biological sample at or near the treatment site to determine an initial, pre-neuromodulation level or activity of one or more target biomarkers. In some embodiments, the collected baseline sample can be conveyed directly from the sampling port 108 through the sampling lumen 400 to the analyzer 120 (e.g., when the analyzer 120 is incorporated into the handle 112). The analyzer 120 can be configured to analyze the pre-neuromodulation sample to detect a baseline level of one or more target biomarkers. In other embodiments, the collected baseline sample can be conveyed directly from the sampling port 108 through the sampling lumen 400 to the console 132 via the connector 130 and/or a separate collection connector (not shown) between the handle 112 and the console 132. As discussed below, the baseline level or value can be compared to a post-neuromodulation level to evaluate the efficacy of the neuromodulation. When the analysis is complete, the baseline data obtained by the analyzer 120 from the baseline analysis may be stored by memory of the analyzer 120, or in some embodiments, the baseline data can be communicated (e.g., via the connector 130 and/or wirelessly) to memory of the console 132 for storage and/or processing. In addition, the baseline data may be displayed by an analyzer display (not shown) on the handle 112 and/or the console display 136 (FIG. 51). After the baseline data has been obtained, the baseline sample can be removed from the analyzer 120 in the handle 112 to prevent contamination of incoming samples. Furthermore, in some embodiments, the analyzer 120 can be configured to separate and store more than one sample (e.g., reducing or eliminating the need to service the analyzer 120 in between collections).

After the neuromodulation and sampling assembly 102 is adequately positioned in the vessel or lumen, the neuromodulation element 200 can be used to purposefully apply or withdraw energy to or from the tissue to induce one or more desired neuromodulating effects on localized regions of the renal artery and adjacent regions of the renal plexus (RP), which lay intimately within, adjacent to, or in close proximity to the adventitia of the renal artery (RA). During and/or after the application of energy, the system 100 can detect changes in the level or activity of one or more target biomarkers associated with neuromodulation and provide real-time or relatively contemporaneous feedback of neuromodulation efficacy.

Before, during, and/or after the energy delivery or withdrawal, the occlusion member 218 carried by the occlusion element 204 of the neuromodulation and sampling assembly 102 can be inflated and/or expanded to at least partially occlude the vessel or lumen proximal to the treatment site, as shown in FIG. 56D (the direction of blood flow is indicated by arrows "BF"). After the occlusion member 218 is inflated and/or expanded, a negative pressure source can be activated to draw a post-neuromodulation sample proximally through the sampling port 108 and sampling lumen 400 to a proximal portion 114 of the treatment device 110 (e.g., the handle 112). Occlusion of the vessel or lumen upstream of the treatment site is expected to isolate and/or preserve target biomarkers released into the vessel or lumen as a result of the neuromodulation. Additionally, full or partial occlusion can cause pooling of the blood in the vessel or lumen distal to the occlusion member 218 that facilitates collection of a sufficient sample size (e.g., 1-5 cc) for subsequent analysis. In some embodiments, a sufficient sample size volume can be significantly smaller (e.g., less than about 1 cc). For example, the sampling lumen 400 may include an in vivo sensor (described below) and/or test element (described below) that can detect biomarker levels in sample volumes less than about 1 cc. Because the average renal artery contains about 1 cc of collectable biological sample, the occlusion member 218 may remain in a fully or partially inflated and/or expanded state for about 1 to 5 minutes before collection to allow sufficient pooling of the biological sample in the renal artery. Alternatively, in some embodiments, collection of a sample can occur during or after neuromodulation without use of an occlusion member 218. In these cases, the sampling element 202 can be distal to the neuromodulation element 200 so as to be downstream of the treatment site with respect to blood flow and more likely to collect target biomarkers resulting from the neuromodulation.

In some embodiments, collection of the post-neuromodulation sample can include an iterative process of inflating and/or expanding the occlusion member 218, collecting a first quantity of the sample, partially deflating the occlusion member 218 to allow perfusion of the renal artery, then re-inflating and/or re-expanding the occlusion member 218 to collect a second quantity of the sample. Such an iterative process can be used to collect any desired number of sample quantities until a sufficient sample volume has been reached. As discussed above, inflation and deflation of the occlusion member 218 can be automatically or manually controlled to achieve a desired occlusion to perfusion ratio. In some embodiments, the therapeutic element 502 can be configured to radially expand into a deployed state 504 at the treatment location.

The devices, systems and methods for conveying the post-neuromodulation sample from the sampling port 108 to an analyzer 120 and for analyzing the post-neuromodulation sample can be the same as that described above with respect to the baseline or pre-neuromodulation sample. Once determining the post-neuromodulation target biomarker level or activity, the processing circuitry associated with the analyzer 120, handle 112, and/or console 132 can compare the post-neuromodulation biomarker level or activity to the baseline level or activity and provide real-time or relatively contemporaneous feedback (e.g., auditory or visual) to the practitioner as to the efficacy of the neuromodulation. For example, target biomarkers for use in the methods disclosed herein may exhibit a change (e.g., a two-fold or greater, a three-fold or greater, a five-fold or greater, or a ten-fold or greater change) in level or activity in response to neuromodulation. If the feedback indicates that a neuromodulation treatment has not been effective, the neuromodulation element 200 can be re-activated (e.g., shifted and then reactivated) to perform a second neuromodulation. Once the second neuromodulation treatment is complete, an additional post-neuromodulation sample can be collected and analyzed to determine whether or not to continue treatment. This process can be repeated until sufficient neuromodulation has been effectuated at the treatment site.

Further Examples

The following examples are illustrative of several embodiments of the present technology:

1. A method of monitoring the efficacy of a renal neuromodulation procedure in a human subject, the method comprising:
   determining a baseline level or activity of one or more target biomarkers;
   at least partially inhibiting sympathetic neural activity in a renal nerve of the subject via a neuromodulation assembly;
   determining a post-neuromodulation level or activity for the target biomarker(s); and
   comparing the post-neuromodulation level or activity to the baseline level or activity, wherein the neuromodulation procedure is classified as successful if the post-neuromodulation level or activity differs significantly from the baseline level or activity.

2. The method of example 1 wherein at least partially inhibiting sympathetic neural activity in a renal nerve of the subject comprises delivering energy to the renal nerve via the neuromodulation assembly to modulate the renal nerve.

3. The method of example 2 wherein the energy is radio frequency (RF) energy.

4. The method of example 2 wherein the energy is selected from the group consisting of pulsed RF energy, microwave energy, laser light energy, optical energy, ultrasound energy, high-intensity focused ultrasound energy, magnetic energy, direct heat energy, and cryotherapeutic energy.

5. The method of any one of examples 1 to 4 wherein at least partially inhibiting sympathetic neural activity in a renal nerve of the subject comprises delivering a chemical to the renal nerve via the neuromodulation assembly to modulate the renal nerve.

6. The method of any one of examples 1 to 5 wherein the neuromodulation assembly comprises an intravascularly positioned catheter carrying an energy delivery element positioned at least proximate to the renal nerve.

7. The method of any one of examples 1 to 6 wherein at least partially inhibiting sympathetic neural activity in a renal nerve of the subject comprises thermally modulating the renal nerve via the neuromodulation assembly from within a renal blood vessel of the subject.

8. The method of example 1 wherein at least partially inhibiting sympathetic neural activity in a renal nerve of the subject comprises delivering a chemical agent to tissue at a treatment location in the renal blood vessel in a manner that modulates sympathetic neural activity.

9. The method of any one of examples 1 to 8 wherein the one or more target biomarkers are selected from the group consisting of ADRA2b, ATP1A1, BDNF, BMP7, BNP, BTG2, CALCB, CD40L, CDKN1B, CDKN2B/p15, CLU, DNAJA4, DNAJB1, EDN3, ETB, FASLG, FOS, HMOX-1, HSPA5, HSPA14, HSPB1, HSPD1, HSPH1, IL-10, ITGAM, KLKB1, LIF, MC2R, NTF3, P2RY12, SELE, SLC2A5/GLUT5, SOD2, TLR3, TLR4, TLR7, and TNFRSF1B.

10. The method of any one of examples 1 to 8 wherein the one or more target biomarkers are selected from the group consisting of CASP10, CCL13, CCND1, CD70, CRYAB, CPS1, DNAJB1, DNAJB11, HSPA1A, HSPA1B, HSPB6, IL-10, KIT, LTA, MYLK3, NODAL, NPY1R, POU1F1, and TCP1.

11. The method of any one of examples 1 to 8 wherein the one or more target biomarkers are selected from the group consisting of ACTA2, CACY/2A9, CFL1, CTAG1A1/CTAG21, LDHA, MGC141/TMEM141, NAA20/NAT5, NM23B, PAHX/PHYH1, PFDN1, PLK-2, TUBA1B, and VIM.

12. The method of any one of examples 1 to 8 wherein the one or more target biomarkers are selected from the group consisting of SNCA, BDNF, CNTF, FGF2, GDNF, NGF2, NTF3, PF4, EDN2, ACE2, IFN-γ, ARTN, LIF, CBLN1, NRG1, NRG2, NRG4, PSPN, NTF4, and TGFA.

13. The method of any one of examples 1 to 8 wherein the one or more target biomarkers are selected from the group consisting of NE, CFL1, NPY, DBN, $Ca^{2+}$, renin, DBH, AGT, endothelin 1, 2, and 3, NTS, and APP.

14. The method of any one of examples 1 to 13 wherein the post-neuromodulation level or activity of the target biomarker(s) is determined at 10 minutes, 24 hours, or 7 days post-denervation.

15. A method of performing a renal neuromodulation procedure in a human patient, the method comprising:
   intravascularly positioning a neuromodulation assembly proximate to a renal nerve of the patient;
   determining a baseline level or activity of one or more target biomarkers prior to or after positioning the neuromodulation assembly;
   partially disrupting function of the renal nerve by applying energy to the renal nerve via the neuromodulation assembly;
   determining a post-neuromodulation level or activity for the target biomarker(s); and
   comparing the post-neuromodulation level or activity to the baseline level or activity,
   wherein the neuromodulation procedure is classified as successful if the post-neuromodulation level or activity differs significantly from the baseline level or activity.

16. The method of example 15 wherein partially disrupting function of the renal nerve comprises reducing renal nerve hyperplasia in the patient.

17. The method of example 15 or example 16 wherein partially disrupting function of the renal nerve comprises reducing the total number of functioning renal nerves of the patient to levels at or near levels observed in normotensive patients.

18. The method of any one of examples 15 to 17 wherein the one or more target biomarkers are selected from the group consisting of ADRA2b, ATP1A1, BDNF, BMP7, BNP, BTG2, CALCB, CD40L, CDKN1B, CDKN2B/p15, CLU, DNAJA4, DNAJB1, EDN3, ETB, FASLG, FOS, HMOX-1, HSPA5, HSPA14, HSPB1, HSPD1, HSPH1, IL-10, ITGAM, KLKB1, LIF, MC2R, NTF3, P2RY12, SELE, SLC2A5/GLUT5, SOD2, TLR3, TLR4, TLR7, and TNFRSF1B.

19. The method of any one of examples 15 to 17 wherein the one or more target biomarkers are selected from the group consisting of CASP10, CCL13, CCND1, CD70, CRYAB, CPS1, DNAJB1, DNAJB11, HSPA1A, HSPA1B, HSPB6, IL-10, KIT, LTA, MYLK3, NODAL, NPY1R, POU1F1, and TCP1.

20. The method of any one of examples 15 to 17 wherein the one or more target biomarkers are selected from the group consisting of ACTA2, CACY/2A9, CFL1, CTAG1A1/CTAG21, LDHA, MGC141/TMEM141, NAA20/NAT5, NM23B, PAHX/PHYH1, PFDN1, PLK-2, TUBA1B, and VIM.

21. The method of any one of examples 15 to 17 wherein the one or more target biomarkers are selected from the group consisting of SNCA, BDNF, CNTF, FGF2, GDNF, NGF2, NTF3, PF4, EDN2, ACE2, IFN-γ, ARTN, LIF, CBLN1, NRG1, NRG2, NRG4, PSPN, NTF4, and TGFA.

22. The method of any one of examples 15 to 17 wherein the one or more target biomarkers are selected from the group consisting of NE, CFL1, NPY, DBN, $Ca^{2+}$, renin, DBH, AGT, endothelin 1, 2, and 3, NTS, and APP.

23. A method of determining biomarker activity in a human patient, the method comprising:
    transluminally positioning an energy delivery element of a catheter within a target blood vessel of the patient and adjacent to target neural fibers;
    at least partially ablating the target neural fibers via the energy delivery element;
    capturing a plurality of at least one type of biomarker in a capture compartment of the catheter, wherein the biomarker(s) are secreted as a result of the ablation procedure;
    sequestering the plurality of the at least one type of biomarker in the capture compartment to concentrate the biomarker(s);
    binding the biomarker(s) to at least one immobilized capture agent disposed on an inner surface of the capture compartment; and
    detecting a concentration of the biomarker(s), wherein the concentration corresponds, at least in part, to a degree of ablation of the target neural fibers.

24. The method of example 23 wherein the catheter further comprises a distal filter at a distal end of the capture compartment, and wherein capturing a plurality of at least one type of biomarker in a capture compartment of the catheter comprises allowing passage of the biomarker(s) through the distal filter into the capture compartment, while preventing passage of other biomolecules through the distal filter into the capture compartment.

25. The method of example 23 or example 24 wherein the catheter further comprises a proximal filter at a proximal end of the capture compartment, and wherein capturing a plurality of at least one type of biomarker in a capture compartment of the catheter comprises preventing passage of the biomarker(s) out of the capture compartment through the proximal filter, while allowing blood to flow through the proximal filter and out of the capture compartment.

26. The method of any one of examples 23 to 25 wherein the capture compartment of the catheter is located within the patient while capturing the biomarker(s).

27. The method of any one of examples 23 to 25 wherein the capture compartment of the catheter is located external to the patient while capturing the biomarker(s).

28. A method of monitoring the efficacy of a renal neuromodulation procedure in a human subject, the method comprising:
    determining a baseline level or activity of one or more target biomarkers;
    at least partially inhibiting sympathetic neural activity in a renal nerve of the subject via a neuromodulation assembly;
    determining a post-neuromodulation level or activity for one or more target biomarker; and
    comparing the post-neuromodulation level or activity for the one or more target biomarkers to a pre-determined threshold level or activity, wherein the neuromodulation procedure is classified as successful if the post-neuromodulation level or activity is greater than the pre-determined threshold level or activity.

29. A device for carrying out the method of any one of examples 1 to 28.

CONCLUSION

The above detailed descriptions of embodiments of the technology are not intended to be exhaustive or to limit the technology to the precise form disclosed above. Although specific embodiments of, and examples for, the technology are described above for illustrative purposes, various equivalent modifications are possible within the scope of the technology, as those skilled in the relevant art will recognize. For example, while steps are presented in a given order, alternative embodiments may perform steps in a different order. The various embodiments described herein may also be combined to provide further embodiments. All references cited herein are incorporated by reference as if fully set forth herein.

From the foregoing, it will be appreciated that specific embodiments of the technology have been described herein for purposes of illustration, but well-known structures and functions have not been shown or described in detail to avoid unnecessarily obscuring the description of the embodiments of the technology. Where the context permits, singular or plural terms may also include the plural or singular term, respectively.

Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications may be made without deviating from the technology. Further, while advantages associated with certain embodiments of the technology have been described in the context of those embodiments, other embodiments may also exhibit such advantages, and not all embodiments need necessarily exhibit such advantages to fall within the scope of the technology. Accordingly, the

We claim:

1. A method of determining biomarker activity in a human patient, the method comprising:
    transluminally positioning a first energy delivery element of a catheter within a target blood vessel of the patient and adjacent to target neural fibers;
    at least partially ablating the target neural fibers via the first energy delivery element;
    capturing a plurality of at least one type of biomarker in a capture compartment of the catheter, wherein the biomarker(s) are secreted as a result of the ablation procedure;
    sequestering the plurality of the at least one type of biomarker in the capture compartment to concentrate the biomarker(s);
    binding the biomarker(s) to at least one immobilized capture agent disposed on an inner surface of the capture compartment; and
    detecting a concentration of the biomarker(s), wherein the concentration corresponds, at least in part, to a degree of ablation of the target neural fibers.

2. The method of claim 1 wherein the at least one type of biomarker is selected from the group consisting of ADRA2b, ATP1A1, BDNF, BMP7, BNP, BTG2, CALCB, CD40L, CDKN1B, CDKN2B/p15, CLU, DNAJA4, DNAJB1, EDN3, ETB, FASLG, FOS, HMOX-1, HSPA5, HSPA14, HSPB1, HSPD1, HSPH1, IL-10, ITGAM, KLKB1, LIF, MC2R, NTF3, P2RY12, SELE, SLC2A5/GLUT5, SOD2, TLR3, TLR4, TLR7, and TNFRSF1B.

3. The method of claim 1 wherein the at least one type of biomarker is selected from the group consisting of CASP10, CCL13, CCND1, CD70, CRYAB, CPS1, DNAJB1, DNAJB11, HSPA1A, HSPA1B, HSPB6, IL-10, KIT, LTA, MYLK3, NODAL, NPY1R, POU1F1, and TCP1.

4. The method of claim 1 wherein the at least one type of biomarker is selected from the group consisting of ACTA2, CACY/2A9, CFL1, CTAG1A1/CTAG21, LDHA, MGC141/TMEM141, NAA20/NAT5, NM23B, PAHX/PHYH1, PFDN1, PLK-2, TUBA1B, and VIM.

5. The method of claim 1 wherein the at least one type of biomarker is selected from the group consisting of SNCA, BDNF, CNTF, FGF2, GDNF, NGF2, NTF3, PF4, EDN2, ACE2, IFN-γ, ARTN, LIF, CBLN1, NRG1, NRG2, NRG4, PSPN, NTF4, and TGFA.

6. The method of claim 1 wherein the at least one type of biomarker is selected from the group consisting of NE, CFL1, NPY, DBN, $Ca^{2+}$, renin, DBH, AGT, endothelin 1, 2, and 3, NTS, and APP.

7. The method of claim 1 wherein the concentration of the biomarker(s) is determined at 10 minutes, 24 hours, or 7 days post-ablation.

8. The method of claim 1 wherein at least partially ablating the target neural fibers via the energy delivery element comprises reducing renal nerve hyperplasia in the patient.

9. The method of claim 1 wherein at least partially ablating the target neural fibers via the energy delivery element comprises reducing the total number of functioning renal nerves of the patient to levels at or near levels observed in normotensive patients.

10. The method of claim 1 wherein the catheter further comprises a distal filter at a distal end of the capture compartment, and wherein capturing a plurality of at least one type of biomarker in a capture compartment of the catheter comprises allowing passage of the biomarker(s) through the distal filter into the capture compartment, while preventing passage of other biomolecules through the distal filter into the capture compartment.

11. The method of claim 1 wherein the catheter further comprises a proximal filter at a proximal end of the capture compartment, and wherein capturing a plurality of at least one type of biomarker in a capture compartment of the catheter comprises preventing passage of the biomarker(s) out of the capture compartment through the proximal filter, while allowing blood to flow through the proximal filter and out of the capture compartment.

12. The method of claim 1 wherein the capture compartment of the catheter is located within the patient while capturing the biomarker(s).

13. The method of claim 1 wherein the capture compartment of the catheter is located external to the patient while capturing the biomarker(s).

14. The method of claim 1 wherein the at least one type of biomarker comprises BDNF.

15. The method of claim 1 wherein detecting a concentration of the biomarker(s) comprises detecting the concentration while at least partially ablating the target neural fibers.

16. The method of claim 15 wherein the at least one type of biomarker comprises BDNF.

17. The method of claim 1 wherein detecting a concentration of the biomarker(s) comprises detecting the concentration within 1 minute of at least partially ablating the target neural fibers.

18. The method of claim 17 wherein the at least one type of biomarker comprises BDNF.

19. The method of claim 1 wherein detecting a concentration of the biomarker(s) comprises detecting the concentration within 5 minutes of at least partially ablating the target neural fibers.

20. The method of claim 19 wherein the at least one type of biomarker comprises BDNF.

21. The method of claim 1 wherein detecting a concentration of the biomarker(s) comprises detecting the concentration within 15 minutes of at least partially ablating the target neural.

22. The method of claim 21 wherein the at least one type of biomarker comprises BDNF.

23. The method of claim 1 wherein detecting a concentration of the biomarker(s) comprises detecting the concentration within 30 minutes of at least partially ablating the target neural fiber.

24. The method of claim 23 wherein the at least one type of biomarker comprises BDNF.

25. The method of claim 1 wherein the first energy delivery element comprises an electrode.

26. The method of claim 1 wherein the first energy delivery element comprises an RF electrode.

27. The method of claim 1 wherein the first energy delivery element comprises an RF transducer.

28. The method of claim 1 wherein the first energy delivery element comprises a cryotherapeutic cooling assembly.

29. The method of claim 1 wherein the catheter comprises a plurality of energy delivery elements including the first energy delivery element.

* * * * *

UNITED STATES PATENT AND TRADEMARK OFFICE
CERTIFICATE OF CORRECTION

PATENT NO. : 9,510,777 B2  
APPLICATION NO. : 13/791681  
DATED : December 6, 2016  
INVENTOR(S) : Hezi-Yamit et al.

Page 1 of 1

It is certified that error appears in the above-identified patent and that said Letters Patent is hereby corrected as shown below:

In the Claims

In Claim 21, "The method of claim 1 wherein detecting a concentration of the biomarker(s) comprises detecting the concentration within 15 minutes of at least partially ablating the target neural." should read -- The method of claim 1 wherein detecting a concentration of the biomarker(s) comprises detecting the concentration within 15 minutes of at least partially ablating the target neural fibers. --

In Claim 23, "The method of claim 1 wherein detecting a concentration of the biomarker(s) comprises detecting the concentration within 30 minutes of at least partially ablating the target neural fiber." should read -- The method of claim 1 wherein detecting a concentration of the biomarker(s) comprises detecting the concentration within 30 minutes of at least partially ablating the target neural fibers. --

Signed and Sealed this
Twentieth Day of June, 2017

Joseph Matal
*Performing the Functions and Duties of the
Under Secretary of Commerce for Intellectual Property and
Director of the United States Patent and Trademark Office*